United States Patent
Liu et al.

(10) Patent No.: US 11,806,706 B2
(45) Date of Patent: Nov. 7, 2023

(54) DIRECT NON-OXIDATIVE METHANE CONVERSION IN A CATALYTIC WALL REACTOR

(71) Applicant: University of Maryland, College Park, College Park, MD (US)

(72) Inventors: Dongxia Liu, College Park, MD (US); Su Cheun Oh, College Park, MD (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 157 days.

(21) Appl. No.: 17/288,333

(22) PCT Filed: Oct. 25, 2019

(86) PCT No.: PCT/US2019/058040
§ 371 (c)(1),
(2) Date: Apr. 23, 2021

(87) PCT Pub. No.: WO2020/086952
PCT Pub. Date: Apr. 30, 2020

(65) Prior Publication Data
US 2021/0379549 A1    Dec. 9, 2021

Related U.S. Application Data

(60) Provisional application No. 62/751,362, filed on Oct. 26, 2018.

(51) Int. Cl.
*B01J 8/06*    (2006.01)
*B01J 8/00*    (2006.01)
(Continued)

(52) U.S. Cl.
CPC ............... *B01J 8/065* (2013.01); *B01J 8/001* (2013.01); *B01J 8/008* (2013.01); *B01J 21/08* (2013.01);
(Continued)

(58) Field of Classification Search
CPC .... C07C 2/00; C07C 2/76; C07C 2/82; C07C 2/84; C07C 2521/00; C07C 2521/06;
(Continued)

(56) References Cited

U.S. PATENT DOCUMENTS 5,599,510 A    2/1997    Kaminsky et al.
7,019,184 B2    3/2006    Allison et al.
(Continued)

FOREIGN PATENT DOCUMENTS

EP    3137441 B1    7/2017
WO    2005063615 A1    7/2005
(Continued)

OTHER PUBLICATIONS

Alvarez-Galvan et al., Direct Methane Conversion Routes to Chemicals and Fuels, Catalysis Today, 2011, 171(1): 15-23.
(Continued)

*Primary Examiner* — Natasha E Young
(74) *Attorney, Agent, or Firm* — QUARLES & BRADY LLP

(57) ABSTRACT

Disclosed herein are methane conversion devices that achieve autothermal conditions and related methods using the methane conversion devices.

20 Claims, 51 Drawing Sheets

(51) Int. Cl.
B01J 21/08 (2006.01)
B01J 23/745 (2006.01)
B01J 35/10 (2006.01)
C07C 2/84 (2006.01)

(52) U.S. Cl.
CPC ......... B01J 23/745 (2013.01); B01J 35/1009 (2013.01); C07C 2/84 (2013.01); *B01J 2208/00017* (2013.01); *B01J 2208/024* (2013.01); *B01J 2208/065* (2013.01); *C07C 2521/08* (2013.01); *C07C 2523/745* (2013.01)

(58) Field of Classification Search
CPC ............ C07C 2521/08; C07C 2523/00; C07C 2523/70; C07C 2523/74; C07C 2523/745
See application file for complete search history.

(56) References Cited

U.S. PATENT DOCUMENTS

| | | | |
|---|---|---|---|
| 7,160,344 B2 * | 1/2007 | Choudhary | C01B 3/26 |
| | | | 423/652 |
| 9,776,860 B2 | 10/2017 | Erlebacher et al. | |
| 10,076,739 B1 | 9/2018 | Weissman | |
| 2014/0336432 A1 | 11/2014 | Bao et al. | |

FOREIGN PATENT DOCUMENTS

| | | | | |
|---|---|---|---|---|
| WO | WO-2017062663 A1 * | 4/2017 | ............ | B01D 53/32 |
| WO | 2018146591 A1 | 8/2018 | | |

OTHER PUBLICATIONS

Borry et al., Non-oxidative Catalytic Conversion of Methane with Continuous Hydrogen Removal, Studies in Surface Science and Catalysis, 1998, 119:403-410.
Cao et al., Natural Gas to Fuels and Chemicals: Improved Methane Aromatization in an Oxygen-Permeable Membrane Reactor, Angewandte Chemie International Edition, 2013, 52(51):13794-13797.
Dean, Detailed Kinetic Modeling of Autocatalysis in Methane Pyrolysis, Journal of Physical Chemistry, 1990, 94(4):1432-1439.
DeAngelis et al., Sol-gel Synthesis of Nanocrystalline Fayalite (Fe2SiO4), American Mineralogist, 2012, 97(4):653-656.
Ding et al., Methane Conversion to Aromatics on Mo/H-ZSM5: Structure of Molybdenum Species in Working Catalysts, Journal of Physical Chemistry B, 2001, 105(2):506-513.
Ferrari et al., Interpretation of Raman Spectra of Disordered and Amorphous Carbon, Physical Review B, 2000, 61(20):14095-14107.
Ferrari et al., Raman Spectroscopy as a Versatile Tool for Studying the Properties of Graphene, Nature Nanotechnology, 2013, 8(4):235-246.
Gueret et al., Methane Pyrolysis: Thermodynamics, Chemical Engineering Science, 1997, 52(5):815-827.
Guo et al., Direct, Nonoxidative Conversion of Methane to Ethylene, Aromatics, and Hydrogen, Science, 2014, 344:616-619.
Han et al., Nonoxidative Direct Conversion of Methane on Silica-Based Iron Catalysts: Effect of Catalytic Surface, ACS Catalysis, 2019, 9:7984-7997.
Hao et al., Enhanced Methane Conversion to Olefins and Aromatics by H-Donor Molecules Under Nonoxidative Condition, ACS Catalysis, 2019, 9:9045-9050.
Heller et al., Theory of Graphene Raman Scattering, Acs Nano, 2016, 10(2):2803-2818.
Holmen et al., Pyrolysis of Natural Gas: Chemistry and Process Concepts, Fuel Processing Technology, 1995, 42(2-3):249-267.
Huang et al., A General Framework for the Evaluation of Direct Nonoxidative Methane Conversion Strategies, Joule, 2018, 2(2):349-365.
Karakaya et al., Progress in the Direct Catalytic Conversion of Methane to Fuels and Chemicals, Progress in Energy and Combustion Science, 2016, 55:60-97.
Keramiotis et al., Experimental and Computational Study of Methane Mixtures Pyrolysis in a Flow Reactor Under Atmospheric Pressure, Energy, 2012, 43(1):103-110.
Kolios et al., Efficient Reactor Concepts for Coupling of Endothermic and Exothermic Reactions, Chemical Engineering Science, 2002, 57(9):1505-1510.
Kosinov et al., Selective Coke Combustion by Oxygen Pulsing During Mo/ZSM-5-catalyzed Methane Dehydroaromatization, Angewandte Chemie International Edition, 2016, 55(48):15086-15090.
Kosinov et al., Methane Dehydroaromatization by Mo/HZSM-5: Mono- or Bifunctional Catalysis?, ACS Catalysis, 2017, 7(1):520-529.
Matheu et al., Mechanism Generation with Integrated Pressure Dependence: A New Model for Methane Pyrolysis, Journal of Physical Chemistry A, 2003, 107(41):8552-8565.
Mesters, A Selection of Recent Advances in C1 Chemistry, Annual Review of Chemical and Biomolecular Engineering, 2016, 7:223-238.
Mirzaei et al., Fischer-Tropsch Synthesis over Iron Manganese Catalysts: Effect of Preparation and Operating Conditions on Catalyst Performance, Advances in Physical Chemistry, vol. 2009, Article IDS 151489, 12 pages.
Morejudo et al., Direct Conversion of Methane to Aromatics in a Catalytic co-ionic Membrane Reactor, Science, 2016, 353(6299):563-566.
Oh et al., Direct Non-Oxidative Methane Conversion in a Millisecond Catalytic Wall Reactor, Angew. Chem. Int. Ed., 2019, 58:7083-7086.
Olivos-Suarez et al., Strategies for the Direct Catalytic Valorization of Methane Using Heterogeneous Catalysis: Challenges and Opportunities, ACS Catalysis, 2016, 6(5):2965-2981.
Park et al., Characterization of Phases Formed in the Iron Carbide Process by X-ray Diffraction, Mossbauer, X-ray Photoelectron Spectroscopy, and Raman Spectroscopy Analyses, Metallurgical and Materials Transactions B, 2001, 32:839-845.
Peplow, The Great Gas Gold Rush, Nature, 2017, 550:26-28.
Rao et al., Diameter-Selective Raman Scattering from Vibrational Modes in Carbon Nanotubes, Science, 1997, 275(5297):187-191.
Redenius et al., Millisecond Catalytic Wall Reactors: I. Radiant Burner. AIChE Journal, 2001, 47(5):1177-1184.
Rodrigues et al., CO2 Addition on the Non-Oxidative Dehydro-Aromatization of Methane over MoMCM-22, Catalysis Letters, 2007, 117:166-170.
Sakbodin et al., Hydrogen-Permeable Tubular Membrane Reactor: Promoting Conversion and Product Selectivity for Non-Oxidative Activation of Methane over an Fe © SiO2 Catalyst, Angew. Chem. Int. Ed., 2016, 55(52):16149-16152.
Schwach et al., Direct Conversion of Methane to Value-Added Chemicals Over Heterogeneous Catalysts: Challenges and Prospects, Chemical Reviews, 2017, 117(13):8497-8520.
Spivey et al., Catalytic Aromatization of Methane, Chemical Society Reviews, 2014, 43(3):792-803.
Taifan et al., CH4 Conversion to Value Added Products: Potential, Limitations and Extensions of a Single Step Heterogeneous Catalysis, Applied Catalysis B: Environmental, 2016, 198:525-547.
Tan et al., Methane Aromatization over 2 wt% Mo/HZSM-5 in the Presence of O2 and NO, Catalysis Letters, 2002, 78:251-258.
Tang et al., Methane Activation: The Past and Future, Energy & Environmental Science, 2014, 7(8):2580-2591.
The Quartz Page: The Silica Group, www.quartzpage.de/gen_mod.html, Jan. 12, 2014, 18 pages.
Tonkovich et al., From Seconds to Milliseconds to Microseconds through Tailored Microchannel Reactor Design of a Steam Methane Reformer, Catalysis Today, 2007, 120(1):21-29.
Upham et al., Catalytic Molten Metals for the Direct Conversion of Methane to Hydrogen and Separable Carbon, Science, 2017, 358(6365):917-921.
Venkataraman et al., Millisecond Catalytic Wall Reactors: Dehydrogenation of Ethane, Chemical Engineering Science, 2002, 57(13):2335-2343.

(56) References Cited

OTHER PUBLICATIONS

Venkataraman et al., Steam Reforming of Methane and Water-Gas Shift in Catalytic Wall Reactors, AIChE Journal, 2003, 49(5):1277-1284.
Wanat et al., Steam Reforming and Water-Gas Shift of Ethanol on Rh and Rh—Ce Catalysts in a Catalytic Wall Reactor, Applied Catalysis A: General, 2004, 276(1-2):155-162.
Wang, Y. et al., Raman Spectroscopy of Carbon Materials: Structural Basis of Observed Spectra, Chemistry of Materials, 1990, 2(5):557-563.
Wang, D. et al., Characterization of a Mo/ZSM-5 Catalyst for the Conversion of Methane to Benzene, Journal of Catalysis, 1997, 169(1):347-358.
Wood et al., Gas-to-liquids (GTL): A Review of an Industry Offering Several Routes for Monetizing Natural Gas, Journal of Natural Gas Science and Engineering, 2012, 9:196-208.
Zanfir et al., Catalytic Combustion Assisted Methane Steam Reforming in a Catalytic Plate Reactor, Chemical Engineering Science, 2003, 58(17):3947-3960.
PCT International Search Report and Written Opinion, PCT/US2019/058040, dated Feb. 20, 2020, 17 pages.

\* cited by examiner

DIRECT NON-OXIDATIVE METHANE CONVERSION IN A CATALYTIC WALL REACTOR

CROSS-REFERENCES TO RELATED APPLICATIONS

This is a national stage filing under 35 U.S.C. § 371 of International Application No. PCT/US2019/058040, now WO 2020/086952, filed Oct. 25, 2019, which claims the benefit of U.S. Provisional Application No. 62/751,362 filed Oct. 26, 2018, each of which are incorporated herein by reference for all purposes.

STATEMENT REGARDING FEDERALLY SPONSORED RESEARCH OR DEVELOPMENT

This invention was made with government support under CHET 1351384 and CBET 1642405 awarded by the National Science Foundation. The government has certain rights in the invention.

BACKGROUND OF THE INVENTION

1. Field of the Invention

This invention relates to a methane conversion device and methods for using the methane conversion device.

2. Description of the Related Art

Methane ($CH_4$), the main constituent of natural gas, is deemed to be an alternative source to replace crude oil for the production of chemicals and fuel[1]. $CH_4$ conversion has been explored by indirect processes of $CH_4$ to synthesis gas followed by Fischer-Trøpsch synthesis of higher hydrocarbons[2] or oxidative coupling reactions. Even with low efficiency, high capital cost and high carbon dioxide emissions, the synthesis gas route is the dominant industrial practice. Direct non-oxidative methane conversion (DNMC) is a promising route to convert natural gas into value-added petrochemicals such as ethylene and benzene, when combined are referred to as $C_{2+}$ hydrocarbons, in one step. The reaction, however, is challenged by high-temperature endothermic nature, low $C_{2+}$ yields and coke formation[3].

Past research efforts have studied non-catalytic[4] and catalytic DNMC[5] for $CH_4$ conversion. The non-catalytic route focuses on $CH_4$ pyrolysis to achieve high acetylene yield, but a temperature above 1973 K is required[4a, 6]. In catalytic DNMC, the metal loaded zeolite catalysts are used at temperature below 1073 K, but $CH_4$ conversion is low accompanied with fast catalyst deactivation[7]. The recently reported iron/silica ($Fe/SiO_2$) catalyst is effective for DNMC, which has high $CH_4$ conversion and $C_2+$ yields.[5b] High reaction temperatures exceeding 1200 K and high heat supply for $CH_4$ activation on $Fe/SiO_2$ catalyst are required, and these challenge the fixed-bed reactor design and operation. The $Fe/SiO_2$ catalyst was synthesized by a melt-fusing method and $SiO_2$ was the α-cristobalite phase.[5e] An induction period was needed to activate the catalyst for DNMC. Technoeconomic and environmental aspects require efficient chemical reactor systems that are low-cost, simple manufacturing and capable of supplying heat for the highly endothermic DNMC reaction.

As such, there is a need in the DNMC technology to design a wall reactor that manipulates $CH_4$ conversion, product selectivity and coke formation to realize its technoeconomic viability.

SUMMARY OF THE INVENTION

To accelerate the application of the DNMC technology, we have developed a millisecond catalytic wall reactor that enables stable methane conversion, $C_2+$ selectivity, coke yield and is durable long-term. These effects originate from initiation of DNMC on reactor wall, and maintenance of the reaction by gas phase chemistry in a reactor compartment. Various temperatures and gas flow rates form a basis for optimizing lighter $C_2$ or heavier aromatic products. High carbon and thermal efficiencies and low cost in reactor materials are realized for the technoeconomic process viability of the DNMC technology.

The catalytic wall reactor is either made of the DNMC catalyst materials or is comprised of the DNMC catalyst material coated onto the quartz support. The DNMC catalyst is a metal atom containing quartz that has the α-quartz crystalline phase, which is made by the hydrogen/oxygen ($H_2/O_2$) flame-fusion method. Iron containing quartz catalyst made by this method is defined as $Fe/SiO_2(Q)$, where "Q" stands for α-quartz crystalline phase of $SiO_2$.

In one aspect, the invention provides a methane conversion device comprising a source of methane; a source of gas including oxygen or oxygen containing compound; a reactor having a first reaction zone and a second reaction zone; a first catalyst, and a second catalyst. In the methane conversion device, a first valve is in fluid communication with the source of methane, the first reaction zone, and the second reaction zone. The first valve has a first position in which the first reaction zone is placed in fluid communication with the source of methane, and the first valve has a second position in which the second reaction zone is placed in fluid communication with the source of methane. The first valve can also be fluid communication with an oxygen source.

In the methane conversion device, a second valve is in fluid communication with the source of gas, the first reaction zone, and the second reaction zone. The second valve has a first position in which the second reaction zone is placed in fluid communication with the source of gas, and the second valve has a second position in which the first reaction zone is placed in fluid communication with the source of gas. The first catalyst has a surface exposed to the first reaction zone; and the second catalyst has a surface exposed to the second reaction zone.

In the methane conversion device, the first catalyst can be fused to a first side of a wall and the second catalyst can be fused to an opposite second side of the wall. The wall can be tube-shaped. The wall can comprise quartz. The first catalyst and the second catalyst can have the same or different compositions. In one version of the methane conversion device, the first catalyst and the second catalyst both comprise $Fe/SiO_2(Q)$. In one version of the methane conversion device, the first catalyst at least partially defines the first reaction zone and the second catalyst at least partially defines the second reaction zone.

The methane conversion device can further comprise a controller, wherein the controller can be configured to execute a program stored in the controller to: (i) move the first valve from the first position to the second position and move the second valve from the first position to the second position, when the first catalyst has a pre-determined level of surface deposits including coke. The controller can also be configured to execute the program stored in the controller to: (ii) move the first valve from the second position to the first position and move the second valve from the second position to the first position, when the second catalyst has a pre-determined level of surface deposits including coke.

The methane conversion device can further comprise a first flow controller positioned upstream or downstream of the first valve for controlling a flow rate of methane, and a second flow controller positioned upstream or downstream of the second valve for controlling a flow rate of the gas. The controller can be configured to execute the program stored in the controller to: (iii) control the flow rate of methane and control the flow rate of the gas such that the methane conversion device operates autothermally. The controller can be configured to execute the program stored in the controller to: (iv) control the flow rate of methane such that residence time of methane in the first reaction zone or the second reaction zone is in a range of 1-200 milliseconds.

In another aspect, the invention provides a methane conversion device comprising a source of methane; a source of oxygen or oxygen containing compound; a reactor having a reaction zone; a catalyst having a surface exposed to the reaction zone; a controller; a first flow controller for controlling a flow rate of methane into the reaction zone; and a second flow controller for controlling a flow rate of oxygen into the reaction zone. The controller can be configured to execute a program stored in the controller to: (i) control the flow rate of methane and control the flow rate of oxygen such that the methane conversion device operates autothermally. The catalyst can be fused to a first side of a wall and the catalyst is fused to an opposite second side of the wall, which can be tube-shaped. The wall can comprise quartz. The wall can comprise high temperature stable ceramics such as, but not limited to, quartz, alumina, boron nitride, or silicon nitride. The catalyst can comprise $Fe/SiO_2(Q)$. The catalyst can have a BET surface area of 0.1 to 0.5 $m^2/g$. The catalyst can at least partially defines the reaction zone. The controller can be configured to execute the program stored in the controller to: (ii) control the flow rate of methane such that residence time of methane in the reaction zone is in a range of 1-200 milliseconds. The controller can be configured to execute the program stored in the controller to: (iii) control the flow rate of oxygen such that an oxygen level is 1-10 v/v % in the reaction zone.

In yet another aspect, the invention provides a method for autothermal operation of a direct non-oxidative methane conversion (DNMC) device. The method can include the steps of (a) providing a catalytic reactor, wherein the reactor comprises a catalyst fused to a first side of a wall and fused to an opposite second side of the wall; (b) converting methane (MC) by flowing methane into the first side of the wall; (c) obtaining products resulting from the methane conversion (MC) reaction; (d) swapping the MC reaction to the second side of the wall; (e) supplying to the first side of the wall a gas including oxygen resulting in a combustion reaction with one of the products; (f) swapping the combustion reaction from the first side of the wall to the second side of the wall; and (g) swapping the MC reaction from the side of the second wall to the first side of the wall. The products of step (b) can comprise coke, $C_2+$ hydrocarbons, $H_2$, or a combination thereof. The $C_2+$ hydrocarbons can comprise acetylene, ethylene, ethane, benzene, toluene, naphthalene, or a combination thereof. In one version of the method, one of the products of step (e) is coke. The method can further comprise heating the catalytic reactor. The catalytic reactor can be heated to about 1170K to about 1370K. In one version of the method, a flow rate of methane in step (b) is about 10 ml/min to about 50 mL/min. The method can further comprise heating the catalytic reactor, wherein the catalytic reactor is heated to about 1170K to about 1370K, and wherein the flow rate of methane in step (b) is about 10 ml/min to about 50 mL/min. The method can further comprise adjusting the flow rate of methane and the gas to regulate a percentage of methane converted and/or a selectivity of the methane conversion to one or more of the products. The method can further comprise, adjusting the temperature of the catalytic reactor to regulate a percentage of methane converted and/or a selectivity of the methane conversion to one or more of the products. In the method, the percentage of methane converted can be greater than 10%, and a yield $C_2+$ hydrocarbons can be greater than 10%.

In still another aspect, the invention provides a method for producing a millisecond catalytic wall reactor. The method can include the steps of: (a) loading $Fe/SiO_2(Q)$ into a tube; (b) heating the $Fe/SiO_2(Q)$ and the tube; and (c) discharging the $Fe/SiO_2(Q)$ residue. The tube can have an inner and an outer wall. In the method, step (b) is can be repeated multiple times. In the method, the heating can be done by a $H_2/O_2$ flame. The $Fe/SiO_2(Q)$ can be uniformly dispersed and fully embedded in the tube wall, resulting in a catalyst embedded in the tube wall. In the method, the inner and outer wall can comprise a quartz phase. In the method, the $Fe/SiO_2(Q)$ can have a BET surface area of 0.1 to 0.5 $m^2/g$.

In yet another aspect, the invention provides a method of converting methane. The method can include the steps of: flowing methane in a reaction zone of a catalytic reactor; flowing an oxidative co-feed in the reaction zone of the catalytic reactor; and removing products from the catalytic reactor, wherein the products comprise $C_2+$ hydrocarbons and/or aromatics. The catalytic reactor can comprise a $Fe/SiO_2(Q)$ catalyst embedded in a quartz reactor. In the method, the methane flow can be at a rate of 5 to 500 mL/min. In the method, the volume of the oxidative co-feed can be up to 15 v/v %, the volume % being associated to the volume of methane. In the method, the volume of the oxidative co-feed can be from 0 to 15 v/v %, the volume % being associated to the volume of methane. In the method, the volume of the oxidative co-feed can be from 1 to 15 v/v %, the volume % being associated to the volume of methane. In the method, the volume of the oxidative co-feed can be from 0 to 10 v/v %, the volume % being associated to the volume of methane. The oxidative co-feed can comprise $O_2$, $CO_2$, CO, or a combination thereof. The oxidative co-feed can comprise 0 to 15 v/v % of $O_2$. The oxidative co-feed can also comprise 1 to 15 v/v % of $O_2$. The method can further comprise adjusting the v/v % of the oxidative co-feed to regulate a percentage of methane converted and/or a selectivity of the methane conversion to one or more of the products. The method can further comprise adjusting the type of the oxidative co-feed to regulate a percentage of methane converted and/or a selectivity of the methane conversion to one or more of the products. The method can further comprise at a same time as the flowing methane, flowing a carrier gas into the reaction zone. The carrier gas can comprise He, Ar, $N_2$, or a combination thereof. In the method, the flow rate of the carrier gas can be 0.5 to 50 mL/min.

These and other features, aspects, and advantages of the present invention will become better understood upon consideration of the following detailed description, drawings, and appended claims.

BRIEF DESCRIPTION OF THE DRAWINGS

Like reference numerals will be used to refer to like parts from FIG. 5A to FIG. 5B in the following description of the drawings.

DETAILED DESCRIPTION OF THE INVENTION

Figure 5A:
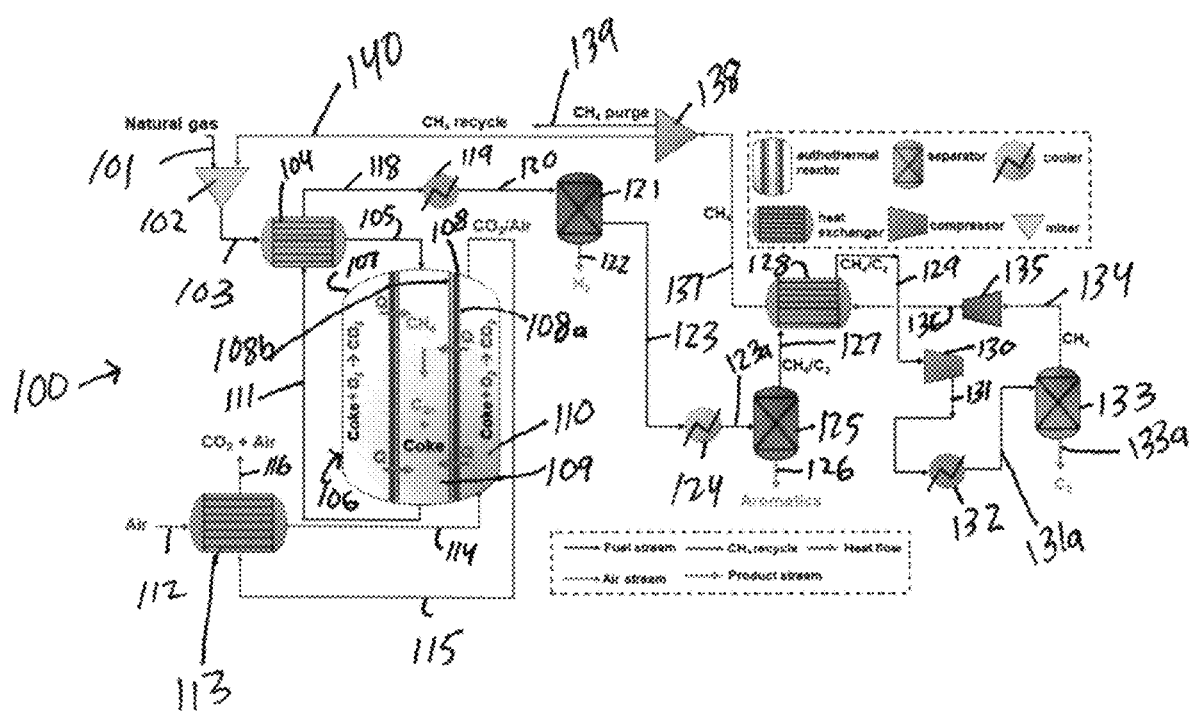
FIG. 5A shows a process flowsheet of autothermal DNMC in millisecond catalytic wall reactor coupling both endothermic DNMC and exothermic coke combustion on opposite sides of the reactor.

Referring to FIG. 5A, there is shown a non-limiting example embodiment of a methane conversion device 100 according to the present invention. As used herein, the term "communication" means that material flow is operatively permitted between enumerated components. A methane feedstock enters the methane conversion device 100 through a line 101 in communication with a mixer 102. The feedstock exits the mixer 102 via line 103, which is in communication with a heat exchanger 104. The feedstock exits the heat exchanger 104 via line 105.

The methane conversion device 100 includes a reactor 106 having a generally cylindrical external housing 107 and an internal tubular wall 108. The wall 108 has a catalyst 108a fused to an outer side of the wall 108, and the wall 108 has a catalyst 108b fused to an inner side of the wall 108. The catalyst 108b defines a generally cylindrical first reaction zone 109, and the catalyst 108a and an inner surface of the housing 108 define a generally tubular second reaction zone 110. The catalyst 108a and the catalyst 108b may be the same catalytic material or different catalytic materials. In one embodiment, the catalysts 108a, 108b are the same, and both comprise a quartz-supported Fe-species ($Fe/SiO_2(Q)$) wherein the support is in the quartz phase. The catalyst can have a BET surface area of 0.1 to 0.5 $m^2/g$.

Line 105 is in communication with an inlet of the first reaction zone 109 for supplying a methane containing feedstock to the first reaction zone 109. In certain embodiments, the gas provided to the first reaction zone 109 of the reactor 106 consists essentially of methane, i.e., minor concentrations (e.g., <20%) of other gases (such as, but not limited to, a tracer or inert gas, $O_2$, CO, $CO_2$, $H_2O$, $H_2S$) may be included but do not otherwise affect the reaction. The methane containing feedstock entering the first reaction zone 109 interacts with catalyst 108b and undergoes a reaction at elevated temperatures (e.g., about 1170K to about 1370K) that results in the production of a product stream of $C_2$+ hydrocarbons and aromatics. The product stream is conveyed from an outlet of the first reaction zone 109 through line 111 to the heat exchanger 104 where heat that is recovered from the product stream can be used to preheat the methane containing feedstock from line 103. During the methane conversion reaction in the first reaction zone 109, coke is deposited on the catalyst 108b.

When the catalytic activity in the first reaction zone 109 decreases to a predetermined level, the methane containing feedstock can be fed to the second reaction zone 110 to interact with catalyst 108a and undergo a reaction at elevated temperatures that results in the production of a product stream of $C_2$+ hydrocarbons and aromatics. The product stream is conveyed from an outlet of the second reaction zone 110 to the heat exchanger 104 where heat that is recovered from the product stream can be used to preheat the methane containing feedstock from line 103. During the methane conversion reaction in the second reaction zone 110, coke is deposited on the catalyst 108a. During the methane conversion reaction in the second reaction zone 110, a gas including oxygen (e.g., air) can be supplied to the first reaction zone 109 for combusting the coke on the catalyst 108b to reactive the catalyst 108b.

The methane conversion device 100 can then be operated using the material flows shown in FIG. 5A. The methane containing feedstock is fed to the first reaction zone 109 where the methane containing feedstock undergoes a reaction at elevated temperatures that results in the production of a product stream including $C_2+$ hydrocarbons and aromatics. The product stream is conveyed from the outlet of the first reaction zone 109 through line 111 to the heat exchanger 104. At the same time, air enters the methane conversion device 100 through a line 112 in communication with a heat exchanger 113. The air exits the heat exchanger 113 via line 114 to be supplied to an inlet of the second reaction zone 110 for combusting the coke on the catalyst 108a to reactive the catalyst 108a. An energy balance between the energy required by the methane conversion reaction in the first reaction zone 109 and the energy released from oxidation of the coke on catalyst 108a in the second reaction zone 110 can be reached to maintain autothermality of the methane conversion reaction.

Still referring to FIG. 5A, the product stream including $C_2+$ hydrocarbons and aromatics exits heat exchanger 104 via line 118 which is in communication with a cooler 119. Line 120 is in communication with a separator 121. A hydrogen fraction is recovered from the separator 121 in a line 122. Line 123 is in communication with the separator 121 and a cooler 124. Line 123a is in communication with a separator 125. An aromatics fraction is recovered from the separator 125 in a line 126. A stream including $CH_4$ and $C_2+$ hydrocarbons is fed via line 127 to a heat exchanger 128. The stream including $CH_4$ and $C_2+$ hydrocarbons is fed via line 129 to a compressor 130, and the stream including $CH_4$ and $C_2+$ hydrocarbons is fed via line 131 to a cooler 132 and exits the cooler 132 via line 131a which feeds the stream including $CH_4$ and $C_2+$ hydrocarbons to a separator 133. A $C_2+$ hydrocarbon fraction is recovered from the separator 133 in a line 133a. Methane exits the separator 133 in a line 134 that feeds a compressor 135. The methane-containing stream is conveyed from an outlet of the compressor 135 to the heat exchanger 128 where heat that is recovered from the methane-containing stream can be used to preheat the stream including $CH_4$ and $C_2+$ hydrocarbons from line 127. The methane-containing stream is conveyed from an outlet of the heat exchanger 128 via line 137 to a mixer 138. At the mixer 138, $CH_4$ purge is shown as line 139, and $CH_4$ is recycled via line 140 back to mixer 102.

Figure 5B:
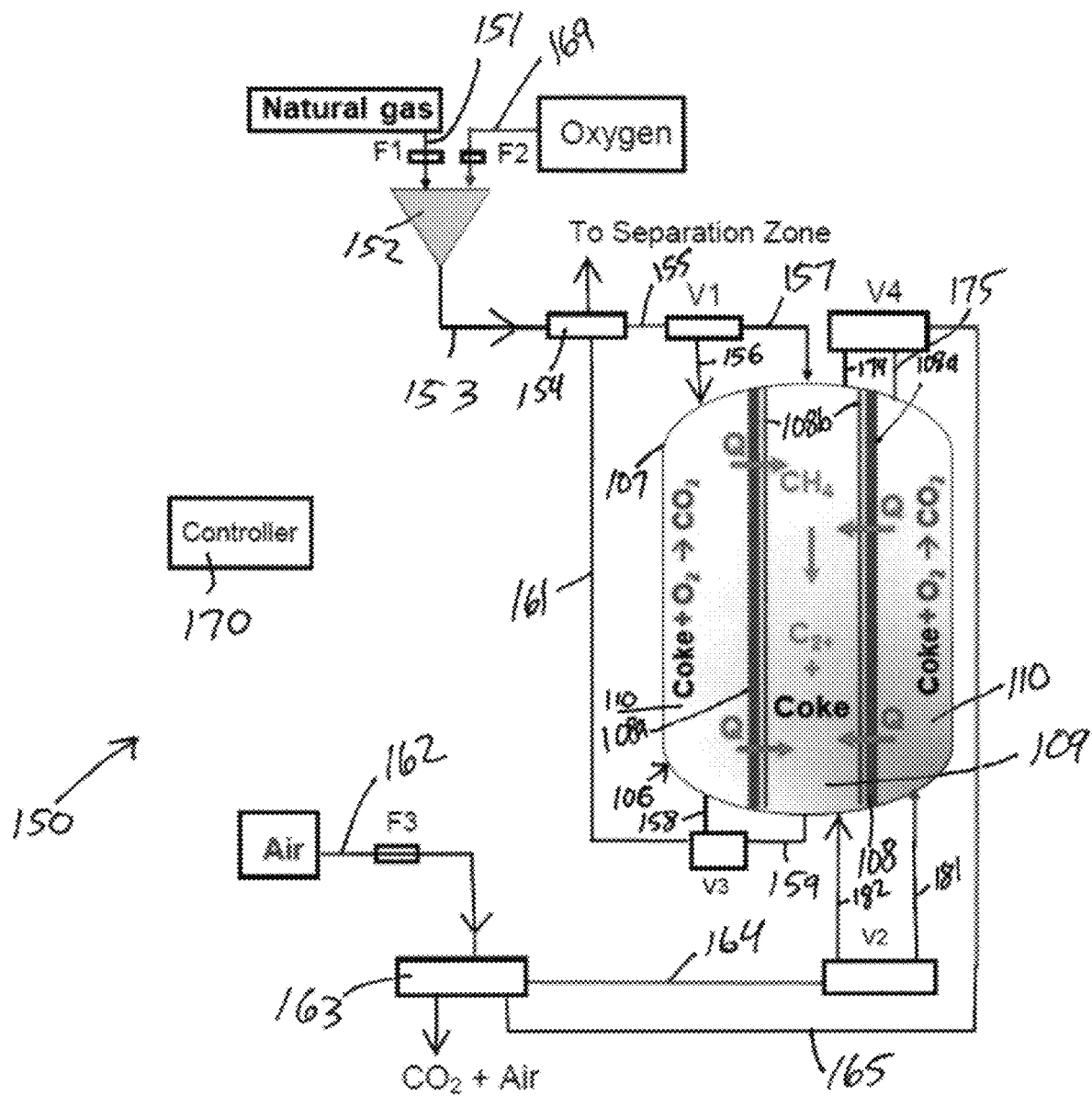
FIG. 5B shows a process flowsheet of autothermal DNMC in millisecond catalytic wall reactor coupling both endothermic DNMC and exothermic coke combustion on opposite sides of the reactor.

Turning now to FIG. 5B, there is shown a non-limiting example embodiment of another methane conversion device 150 according to the present invention for maintaining autothermality of the methane conversion reaction with the use of a valve system, flow controllers, a controller, and/or oxidative co-feed. A methane feedstock enters the methane conversion device 150 through a line 151 in communication with a mixer 152. A flow controller F1 is positioned in line 151 to control the flow rate of methane. Optionally, an oxygen co-feed enters the methane conversion device 150 through a line 169 in communication with the mixer 152. A flow controller F2 is positioned in line 169 to control the flow rate of oxygen. The feedstock of methane and optionally oxygen exits the mixer 152 via line 153, which is in communication with a heat exchanger 154. The feedstock exits the heat exchanger 154 via line 155 and enters a valve V1. The methane conversion device 150 includes a reactor 106 as in the methane conversion device 100 and therefore, the components of the reactor 106 will not be described again.

The valve V1 has a first position in which the first reaction zone 109 is placed in fluid communication with line 155, and a second position in which the second reaction zone 110 is placed in fluid communication with line 155. A valve V3 has a first position in which the first reaction zone 109 is placed in communication with line 161 via line 159, and a second position in which the second reaction zone 110 is placed in fluid communication with line 161 via line 158. Line 161 conveys a product stream to the heat exchanger 154 where heat that is recovered from the product stream can be used to preheat the methane containing feedstock from line 153. The product stream including $C_2+$ hydrocarbons and aromatics exits heat exchanger 154 to a separation zone including components 118 to 140 as in the methane conversion device 100 and therefore, the components of the separation zone will not be described again.

A gas including oxygen (e.g., air) enters the methane conversion device 150 through a line 162 in communication with a heat exchanger 163. A flow controller F3 is positioned in line 162 to control the flow rate of air. The air exits the heat exchanger 163 via line 164 and enters a valve V2. The valve V2 has a first position in which the second reaction zone 110 is placed in fluid communication with line 164 via line 181, and the valve V2 has a second position in which the first reaction zone 109 is placed in fluid communication with the line 164 via line 182. A valve V4 has a first position in which the first reaction zone 109 is placed in communication with line 165 via line 174, and a second position in which the second reaction zone 110 is placed in communication with line 165 via line 175. Line 165 conveys a stream including $CO_2$ and air to the heat exchanger 163 where heat that is recovered from the stream including $CO_2$ and air can be used to preheat the air from line 162.

Figure 4:
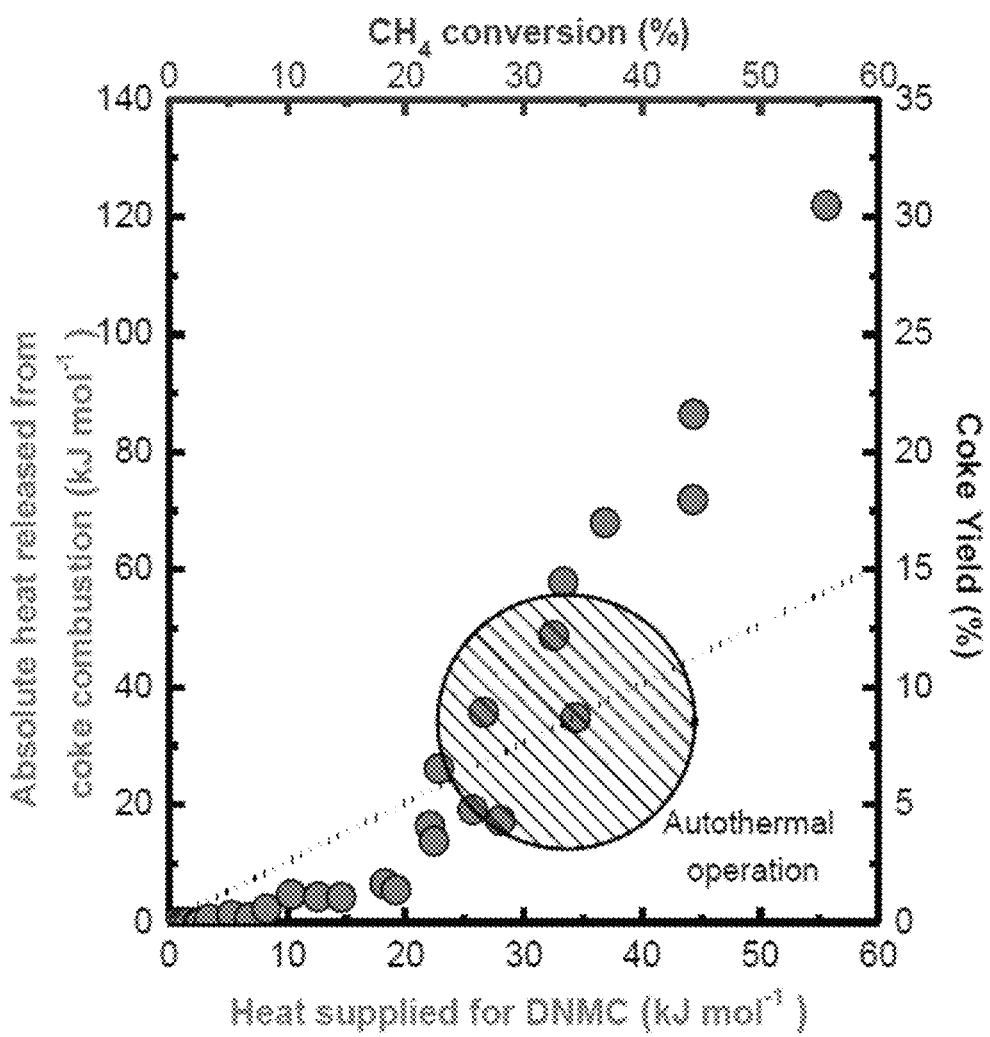
FIG. 4 shows energy input for DNMC and output by coke combustion at corresponding $CH_4$ conversion and coke yield. The dashed line represents the energy input and output balanced from both reactions. The shaded circle indicates the feasible operation window of DNMC autothermally in the reactor.

The methane conversion device 150 includes a programmable logic controller 170 in electrical communication with the valves V1, V2, V3, V4 and the flow controllers F1, F2, F3. FIG. 4B has been simplified by the deletion of the electrical connections between the controller 170 and the valves V1, V2, V3, V4 and flow controllers F1, F2, F3. The valves V1, V2, V3, V4 and flow controllers F1, F2, F3 may be actuated and controlled using control signals provided by the programmable logic controller 170. Such programmable logic controllers are commercially available.

Having described the components and flow paths of the methane conversion device 150, operation of the methane conversion device 150 can be further explained. In one method of operating the methane conversion device 150, the controller 170 and the flow controller F1 control a flow rate of methane into the reaction zone 109, and the controller 170 and the flow controller F2 control a flow rate of oxygen into the reaction zone 109 such that the methane conversion device 150 operates autothermally. A flow rate of methane may be about 10 ml/min to about 500 mL/min. The flow rate of oxygen may be controlled such that an oxygen level is 1-20 v/v % in the first reaction zone 109. Air is not introduced into the reactor 106 via line 162.

In another method of operating the methane conversion device 150, the program in controller 170 is executed to set the valves V1, V2, V3, V4 in positions where a methane containing feedstock enters the first reaction zone 109 interacts with catalyst 108b and undergoes a reaction at elevated temperatures that results in the production of a product stream of $C_2+$ hydrocarbons and aromatics. When the catalyst 108b has a pre-determined level of surface deposits including coke, the program in controller 170 is executed to set the valves V1, V2, V3, V4 in positions where: (i) a methane containing feedstock enters the second reaction zone 110 to interact with catalyst 108a and undergo a reaction at elevated temperatures that results in the production of a product stream of $C_2+$ hydrocarbons and aromatics, and (ii) air is supplied to an inlet of the first reaction zone 109 for combusting the coke on the catalyst 108b to reactive the catalyst 108b. An energy balance between the energy required by the methane conversion reaction in the second reaction zone 110 and the energy released from oxidation of the coke on catalyst 108b in the first reaction zone 108 can be reached to maintain autothermality of the methane conversion reaction. The controller 170 and the flow controller F1 can also control a flow rate of methane, and the controller 170 and the flow controller F3 control a flow rate of air to maintain autothermality of the methane conversion reaction.

When the catalyst 108a has a pre-determined level of surface deposits including coke, the program in controller 170 is executed to set the valves V1, V2, V3, V4 in positions where: (i) a methane containing feedstock enters the first reaction zone 109 to interact with catalyst 108b and undergo a reaction at elevated temperatures that results in the production of a product stream of $C_2+$ hydrocarbons and aromatics, and (ii) air is supplied to an inlet of the second reaction zone 110 for combusting the coke on the catalyst 108a to reactive the catalyst 108a. An energy balance between the energy required by the methane conversion reaction in the first reaction zone 109 and the energy released from oxidation of the coke on catalyst 108a in the second reaction zone 110 can be reached to maintain autothermality of the methane conversion reaction. The controller 170 and the flow controller F1 can also control a flow rate of methane, and the controller 170 and the flow controller F3 control a flow rate of air to maintain autothermality of the methane conversion reaction. Also, the controller 170 and the flow controller F1 can control a flow rate of methane such that residence time of methane in the first reaction zone or the second reaction zone is in a range of 1-200 milliseconds.

The invention also provides a method for autothermal operation of a direct non-oxidative methane conversion (DNMC) device. The method includes the steps of: (a) providing a catalytic reactor, wherein the reactor comprises a catalyst flame-fused to a first side of a wall and fused to an opposite second side of the wall; (b) converting methane (MC) by flowing methane into the first side of the wall; (c) obtaining products resulting from the methane conversion (MC) reaction; (d) swapping the MC reaction to the second side of the wall; (e) supplying to the first side of the wall a gas including oxygen resulting in a combustion reaction with one of the products; (f) swapping the combustion reaction from the first side of the wall to the second side of the wall; and (g) swapping the MC reaction from the side of the second wall to the first side of the wall. The method steps can further include heating the catalytic reactor. The products resulting from the methane conversion reaction may be coke, $C_2+$ hydrocarbons, $H_2$, or a combination thereof. The $C_2+$ hydrocarbons may be acetylene, ethylene, ethane, benzene, toluene, naphthalene, or a combination thereof. Where the method includes the additional step of heating the catalytic reactor, the reactor can be heated from about 1000K to about 2000K. Preferably, the reactor is heated from about 1200K to about 1500K, more preferably from about 1220K to about 1370K. In one embodiment, the heating temperature is about 1323 K. The method can vary the flow rate at which methane is flowed in step (b). The methane flow rate can be from about 5 ml/min to about 500 mL/min, preferably from about 10 ml/min to about 100 mL/min, more preferably from about 10 ml/min to about 50 mL/min. In one embodiment, the methane flow rate is about 20 mL/min. The method results in greater than 10% methane conversion and a yield of $C_2+$ hydrocarbons is greater than 10%. In one embodiment, the method results in about 50% methane conversion. In one embodiment, the yield of $C_2+$ hydrocarbons is from about 10% to about 30%.

The invention also provides a method for producing a millisecond catalytic wall reactor. The method includes the steps of: (a) loading $Fe/SiO_2(Q)$ into a tube; (b) heating the $Fe/SiO_2(Q)$ and the tube; and (c) discharging the $Fe/SiO_2(Q)$ residue. The method may comprise a heating temperature of about 1850K to about 2200K. The method may comprise having the $Fe/SiO_2(Q)$ uniformly dispersed and fully embedded in the tube wall, which results in a catalyst embedded in the tube wall. The reactor may also comprise an inner and outer wall. The inner and outer wall may comprise quartz phase. The reactor may be completely made of $Fe/SiO_2(Q)$ material, which can be achieved via extrusion method. The $Fe/SiO_2(Q)$ catalyst may have a BET surface area of 0.1 to 0.5 $m^2/g$.

The invention also provides a method of converting methane. The method includes the steps of: flowing methane in a reaction zone of a catalytic reactor; flowing an oxidative co-feed in the reaction zone of the catalytic reactor; and removing products from the catalytic reactor, wherein the products comprise $C_2+$ hydrocarbons and/or aromatics. The methane flow rate may be from about 5 mL/min to about 500 mL/min. The oxidative co-feed may comprise $O_2$, $CO_2$, CO, or a combination thereof. The volume of oxidative co-feed may be from 0 to 30 v/v %, the volume % being associated to the volume of methane. The volume of oxidative co-feed may be from 1 to 30 v/v %, the volume % being associated to the volume of methane. Preferably, the volume of the oxidative co-feed may be from 0 to 20 v/v %, the volume % being associated to the volume of methane. More preferably, the volume of the oxidative co-feed may be from 1 to 20 v/v %, the volume % being associated to the volume of methane. Even more preferably, the oxidative co-feed may be 1 to 15 v/v % of $O_2$. The method steps can further include, at a same time as the flowing methane, flowing a carrier gas into the reaction zone. The carrier gas may be He, Ar, $N_2$, or a combination thereof. The flow rate of the carrier gas may be from 0.5 to 50 mL/min.

The invention is further illustrated in the following Examples which are presented for purposes of illustration and not of limitation.

EXAMPLES

Example 1

Direct Non-Oxidative Methane Conversion in a Millisecond Catalytic Wall Reactor

Direct non-oxidative methane conversion (DNMC) has been recognized as a key technology for application of natural gas in the chemical and energy industries. High reaction temperature and low catalyst durability, due to endothermic reaction nature and coke deposition, are two main challenges. We show that a millisecond catalytic wall reactor enables stable methane conversion, $C_2+$ selectivity, coke yield and long-term durability. These effects originate from initiation of DNMC on a reactor wall, and maintenance of the reaction by gas phase chemistry in the reactor compartment. The performance results obtained under various temperatures and gas flow rates form a basis for optimizing lighter $C_2$ or heavier aromatic products. A process simulation done by Aspen Plus explored the practical implications of the catalytic wall reactor. High carbon and thermal efficiencies and low cost in reactor materials are realized for the technoeconomic process viability of the DNMC technology.

Introduction

Methane ($CH_4$), the main constituent of natural gas, is deemed to be an alternative source to replace crude oil for the production of chemicals and fuel[1]. $CH_4$ conversion has been explored by indirect processes of $CH_4$ to synthesis gas followed by Fischer-Trøpsch synthesis of higher hydrocarbons[2] or oxidative coupling reactions. Even with low efficiency, high capital cost and high carbon dioxide emissions, the synthesis gas route is the dominant industrial practice. Direct non-oxidative methane conversion (DNMC) is a promising route to convert natural gas into value-added petrochemicals such as ethylene and benzene, when combined are referred to as $C_2$+ hydrocarbons, in one step. The reaction, however, is challenged by high-temperature endothermic nature, low $C_2$+ yields and coke formation[3].

Past research efforts have studied non-catalytic[4] and catalytic DNMC[5] for $CH_4$ conversion. The non-catalytic route focuses on $CH_4$ pyrolysis to achieve high acetylene yield, but temperature above 1973 K is required[4a, 6]. In catalytic DNMC, the metal loaded zeolite catalysts are used at temperature below 1073 K, but $CH_4$ conversion is low accompanied with fast catalyst deactivation[7]. The recently reported iron/silica (Fe/$SiO_2$) catalyst is effective for DNMC, which has high $CH_4$ conversion and $C_2$+ yields.[5b] The Fe/$SiO_2$ catalyst was synthesized by a melt-fusing method and $SiO_2$ was the α-cristobalite phase.[5e] An induction period was needed to activate the catalyst for DNMC. High reaction temperatures exceeding 1200 K and high heat supply for $CH_4$ activation on Fe/$SiO_2$ catalyst are required, and these challenge the fixed-bed reactor design and operation. Technoeconomic and environmental aspects require efficient chemical reactor systems that are low-cost, simple manufacturing and capable of supplying heat for the highly endothermic DNMC reaction.

Results

Figure 1:
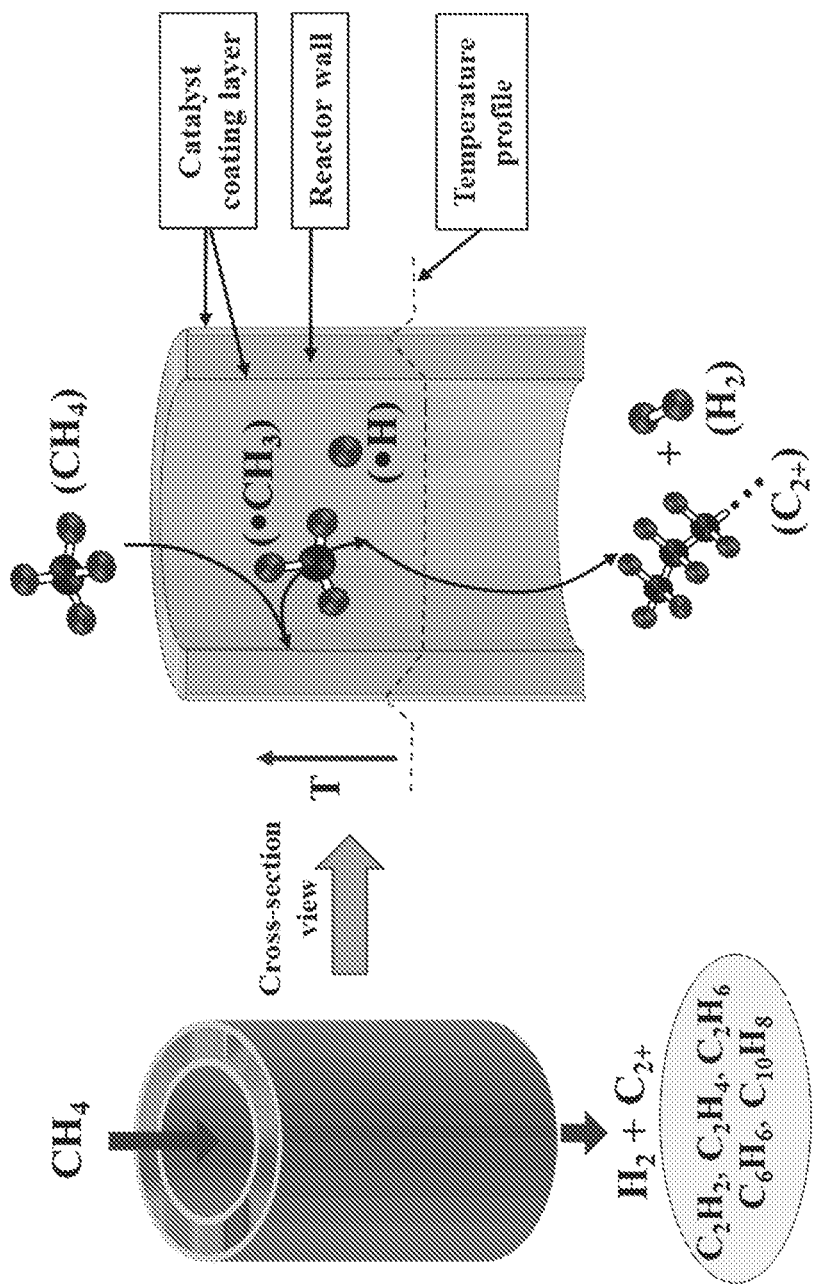
FIG. 1 is a schematic of catalytic wall reactor for $CH_4$ conversion into $C_{2+}$ hydrocarbons and $H_2$ in a DNMC process.

We innovated the DNMC technology by designing a millisecond catalytic wall reactor (FIG. 1) that manipulates $CH_4$ conversion, product selectivity and coke formation to realize its technoeconomic viability. The reactant flows in the reactor channel, and a reaction initiates on the wall surface and happens both on the reactor wall and in the reactor channel. The diffusion time of reactant to the reactive wall is within milliseconds. Such short contact time is viable for chemical synthesis from alkanes, such as oxidative dehydrogenation of hydrocarbons for olefins[8] or hydrogen production[9]. Placing catalyst directly onto the inner and outer walls of the reactor promotes heat transfer in thermal boundary layers so that heat released by exothermic reaction on one side of the reactor can be effectively coupled to heat supply for endothermic reaction on the opposite side[10]. Therefore, the process can be run autothermally and almost adiabatically with a residence time of approximately a few milliseconds. It also guarantees a very high throughput using a smaller amount of catalyst, energy and capital costs, compared to the traditional technology. However, such concept has never been attempted in DNMC reaction.

Figure 2A:
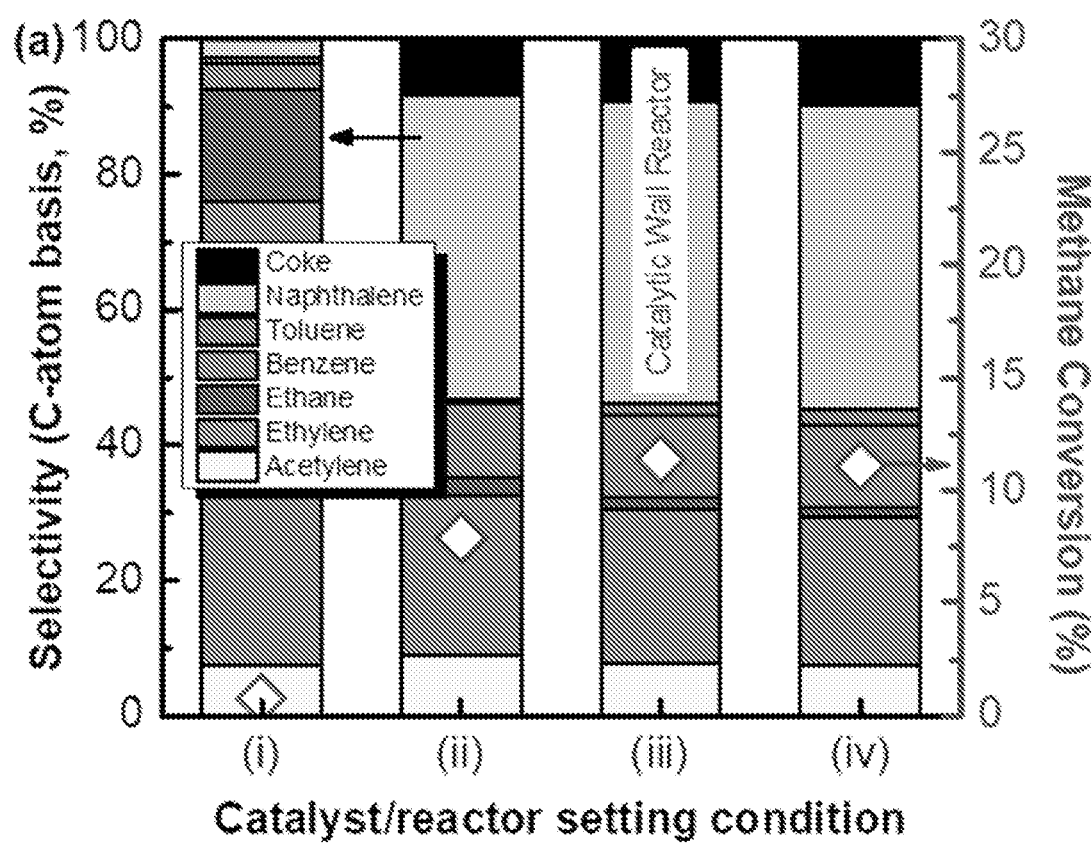
FIG. 2A shows $CH_4$ conversion and product selectivity in different catalyst/reactor settings: (i) blank quartz reactor, (ii) $Fe/SiO_2(Q)$ catalyst packed in quartz reactor, (iii) catalytic wall reactor coated with $Fe/SiO_2(Q)$ catalyst, and (iv) $Fe/SiO_2(Q)$ catalyst packed in catalytic wall reactor.

Our study on the millisecond catalytic wall reactor originated from a critically low surface area of Fe/$SiO_2$(Q) catalyst to activate DNMC in the fixed-bed reactor (FIG. 2A). It should be noted that acetylene, ethylene, ethane, benzene, toluene, naphthalene and coke were the products formed in the DNMC reaction, as shown in our precious work[12]. The Brunauer-Emmett-Teller surface area of our synthesized Fe/$SiO_2$(Q) catalyst is 0.38 $m^2$ $g^{-1}$. By fixing the catalyst bed length with quartz-balanced particles, the surface area of Fe/$SiO_2$(Q) catalyst was varied from 0 to 0.15 $m^2$, equivalent to 0 to 100 wt % mass percentage of Fe/$SiO_2$(Q) in the catalyst bed. $CH_4$ conversion was <1.0% in the blank reactor (FIG. 2B), increased to 5.7% in the reactor packed with quartz particles, and then increased to 10.3% by using 0.036 $m^2$ (or 25 wt %) Fe/$SiO_2$(Q) in catalyst bed, and maintained at ~11.0% with further increase in Fe/$SiO_2$(Q) catalyst quantity. The coke selectivity was the highest in the fixed-bed reactor packed with quartz-balance particles but decreased with increasing Fe/$SiO_2$(Q) usage in the catalyst bed. Clearly, a critically small active surface area of Fe/$SiO_2$(Q) catalyst is sufficient to enable the DNMC. The further increase in Fe/$SiO_2$(Q) catalyst usage did not increase $CH_4$ conversion, suggesting that the DNMC is not an exclusive heterogeneous reaction, but a mixed heterogeneous-homogeneous network, consistent with report by Bao et al.[5b] The Fe/$SiO_2$(Q) catalyst does not need induction period in the DNMC reaction, different from previous Fe/$SiO_2$ catalyst that a catalyst activation period is required.

The requirement for small amount (i.e., surface area) of Fe/$SiO_2$(Q) catalyst in DNMC suggests the potential to develop millisecond catalytic wall reactors comprised of a catalyst coating layer on the reactor wall that offers equivalent catalyst surface area to that in the fixed-bed reactor. The calculation shows that a reactor tube with inner diameter of 4.3 mm and length of 228.6 mm offers 0.036 $m^2$ of surface area, same as that of 25 wt % Fe/$SiO_2$(Q) mixed with 75 wt % quartz-balance particles in the catalyst bed in FIG. 2A. We, therefore, explored for the first time the development of Fe/$SiO_2$(Q) millisecond catalytic wall reactor for DNMC. The manufacturing process includes the curving of softened straight quartz tube into a "U" shape, loading of Fe/$SiO_2$(Q) into U-shaped quartz tube channel, heating of both Fe/$SiO_2$(Q) catalyst and quartz tube to melting temperature, and finally discharging of unmelted catalyst residue. The low cost and abundance of catalyst materials enabled fabrication of the catalytic wall reactor using commercial processes such as extrusion, which produces active surfaces on both sides of the reactor. The simplicity of reactor manufacturing process indicates the great potential in industrial practice of DNMC technology.

Figure 2B:
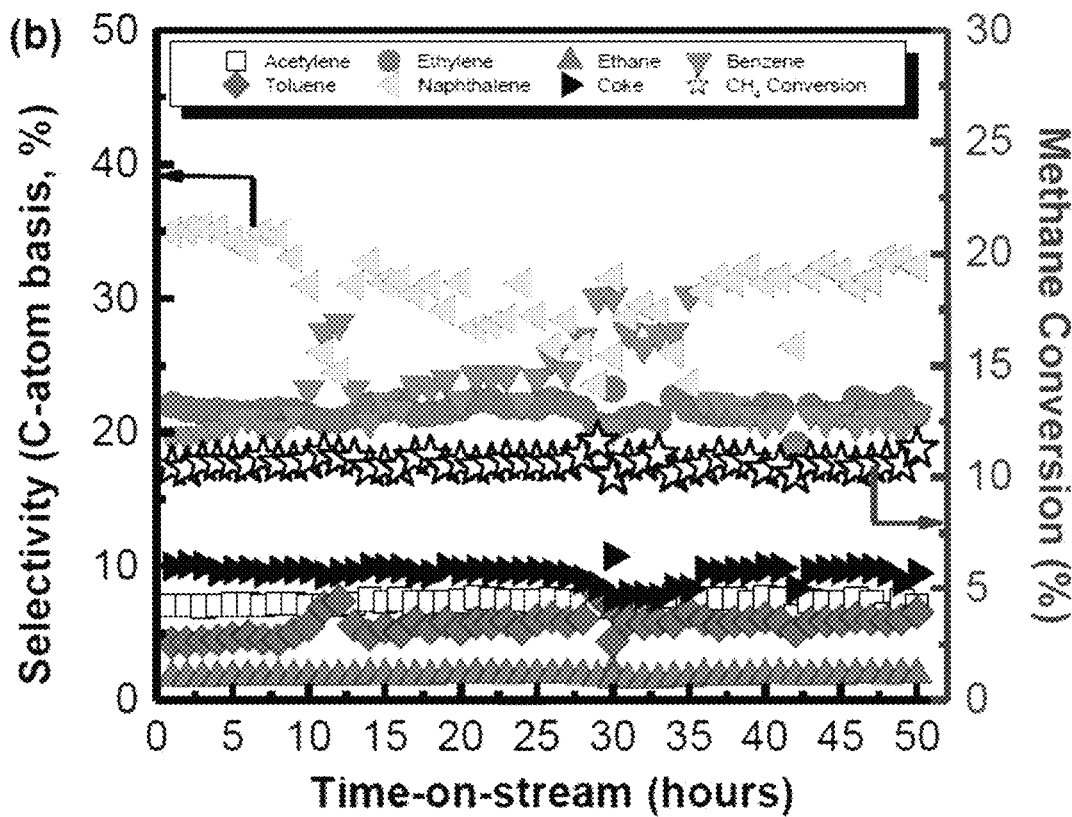
FIG. 2B shows a long-term stability test of a DNMC reaction in a catalytic wall reactor. (1273 K, 20 mL min$^{-1}$ gas flow rate, $CH_4:N_2=9:1$ ($N_2$: internal standard), 1 atm pressure, 0.075 wt % Fe in $Fe/SiO_2(Q)$, 0.375 g catalyst).
Figure 10:
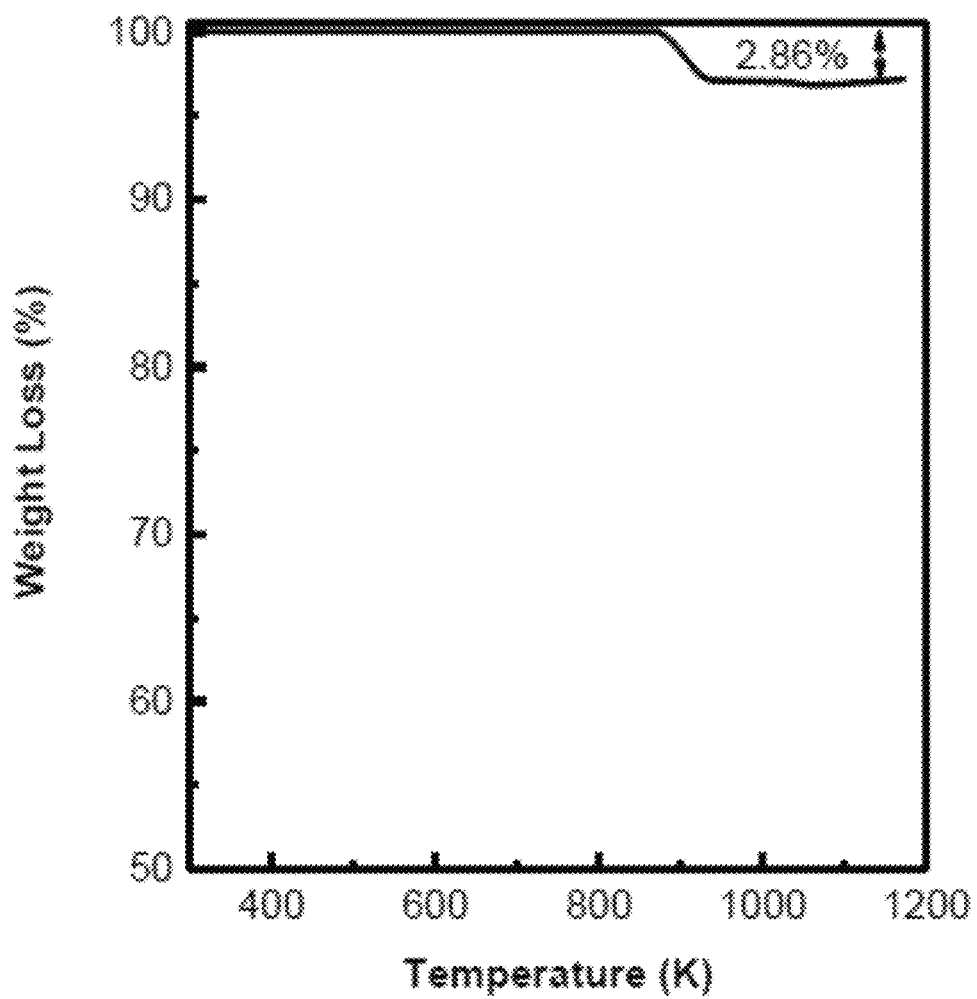
FIG. 10 shows a TGA curve of coke formed on $Fe/SiO_2(Q)$ powder after TOS=4 hours of DNMC reaction (Reaction temperature=1273 K, total gas flow rate=20 mL min$^{-1}$, $CH_4:N_2=9:1$, 1 atm pressure).
Figure 11:
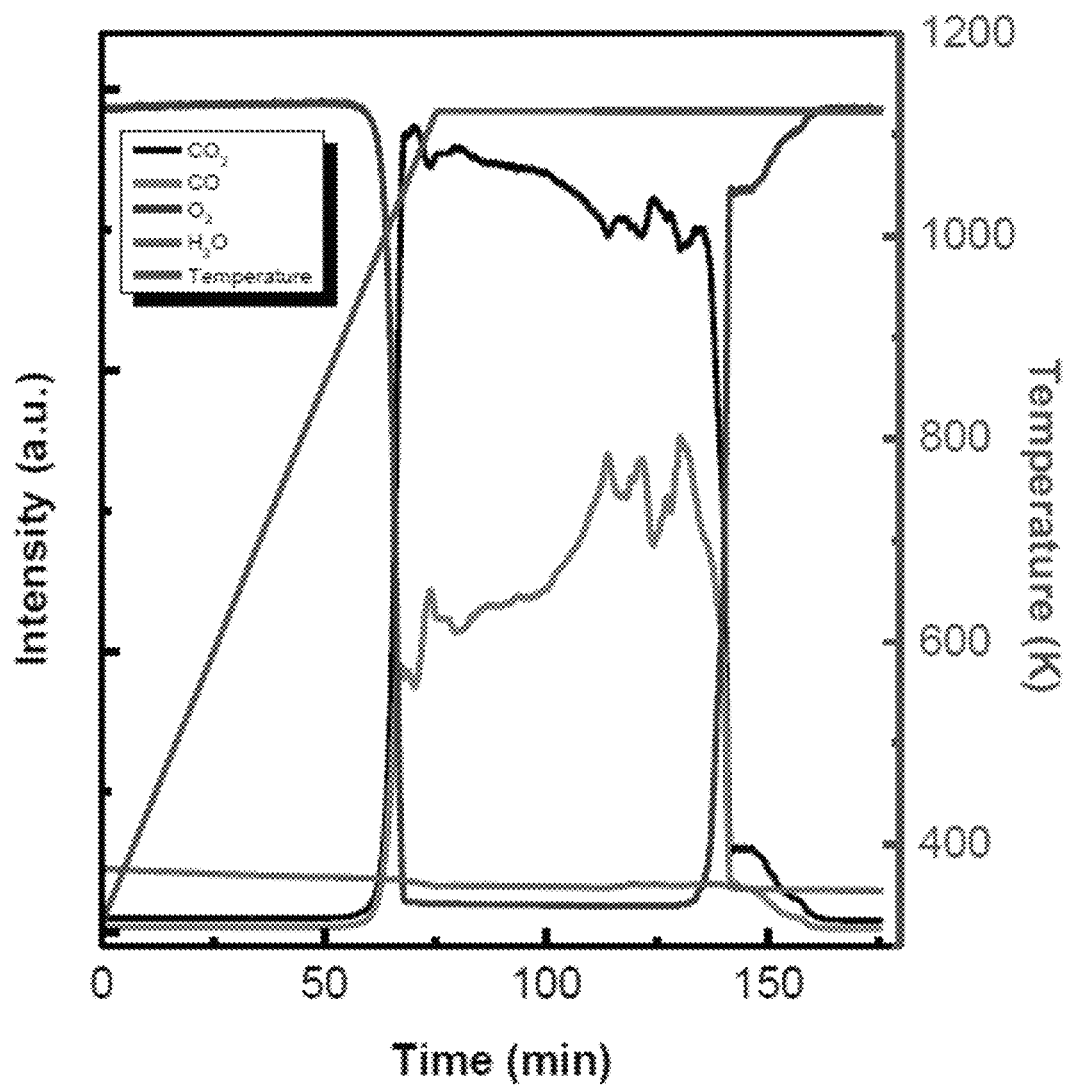
FIG. 11 shows a TPO profile of catalytic wall reactor after TOS=4 hours of DNMC reaction (Reaction temperature=1273 K, total gas flow rate=20 mL min$^{-1}$, $CH_4:N_2=9:1$, 1 atm pressure).

We tested the catalytic wall reactor performance and compared it to the DNMC in a non-catalytic quartz reactor, a fixed-bed quartz reactor packed with Fe/$SiO_2$(Q) catalyst, and a catalytic wall reactor loaded with Fe/$SiO_2$(Q), respectively. In sequence, these four reactor/catalyst settings presented 0.8%, 7.9%, 11.3% and 11.0% $CH_4$ conversions (FIG. 2A). The result confirms that the Fe/$SiO_2$(Q) catalyst was successfully incorporated into the quartz tube wall. Coke formation follows a steady state rate in the catalytic wall reactor. This data suggests that a homogeneous gas phase reaction might play a dominant role after DNMC initiation by the heterogeneous catalyst surface. The long-term stability of the catalytic wall reactor for DNMC was tested by running the reaction at 1273 K for 50 hours (FIG. 2B). $CH_4$ conversion was kept stable at ~11.3%, $C_2$ (30.3%), benzene (21.2%), toluene (6.6%) and naphthalene (32.4%) selectivity remained constant, and the total selectivity to these products ($C_2$+) were kept at >91.0%. The slight spikes at reaction times of ~12 hours and ~32 hours were caused by the temperature fluctuation, as shown in FIG. 10. A reproducibility test showed that the data were reproducible in multiple tests with multiple catalytic wall reactors made following the same procedure (FIG. 11). The combination of high CH$_4$ conversion, high product selectivity and excellent stability in the catalytic wall reactor is undeniably remarkable.

Figure 3A:
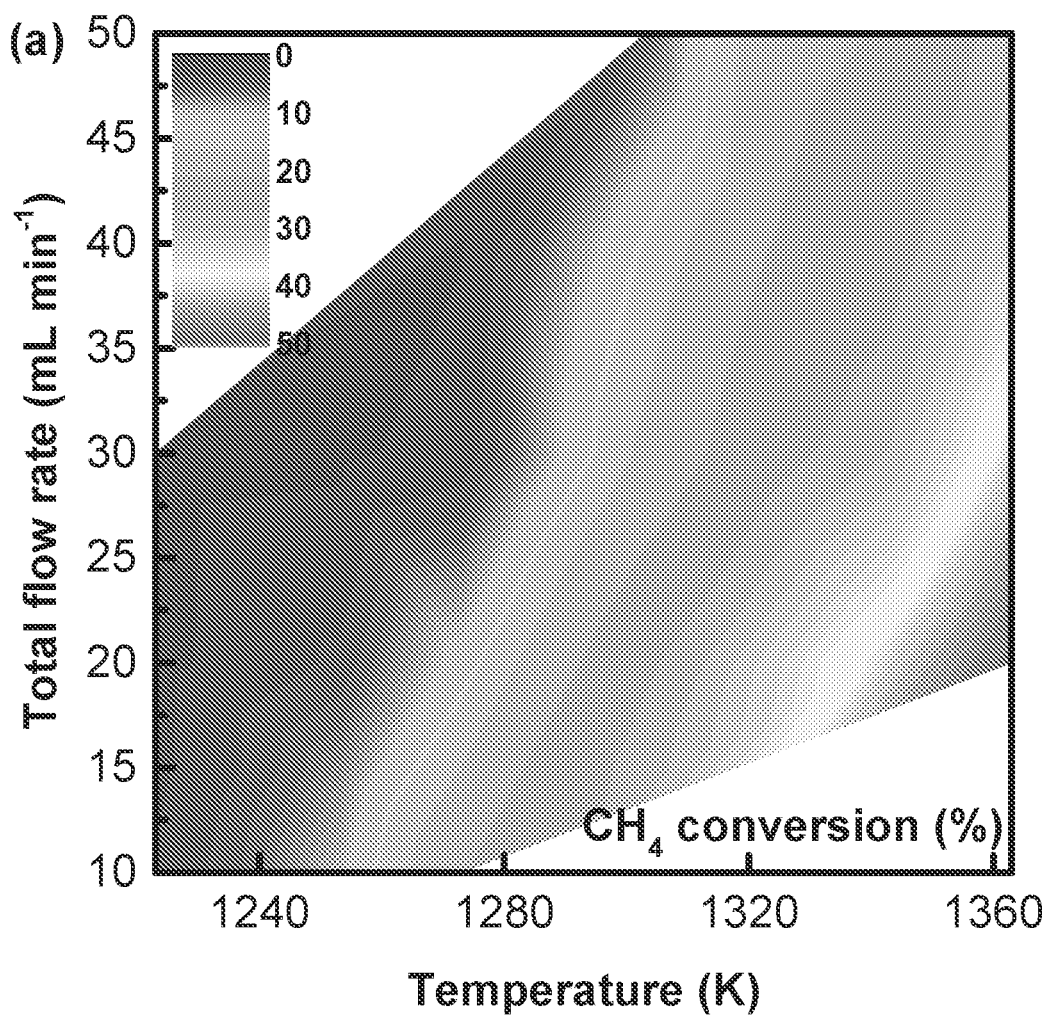
FIG. 3A shows $CH_4$ conversion as a function of reaction temperature and feed gas flow rate. ($C_2+$ selectivity and yield and coke yield are calculated from the carbon-atom basis).
Figure 3B:
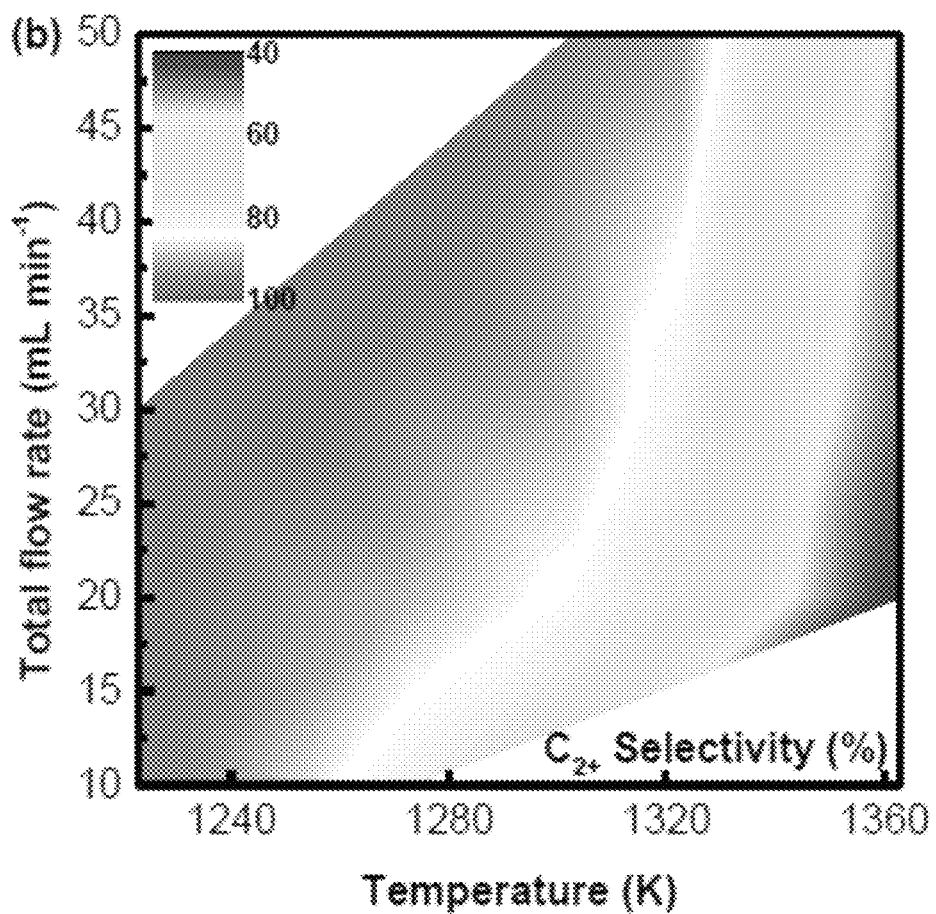
FIG. 3B shows $C_2+$ selectivity as a function of reaction temperature and feed gas flow rate. ($C_2+$ selectivity and yield and coke yield are calculated from the carbon-atom basis).
Figure 3C:
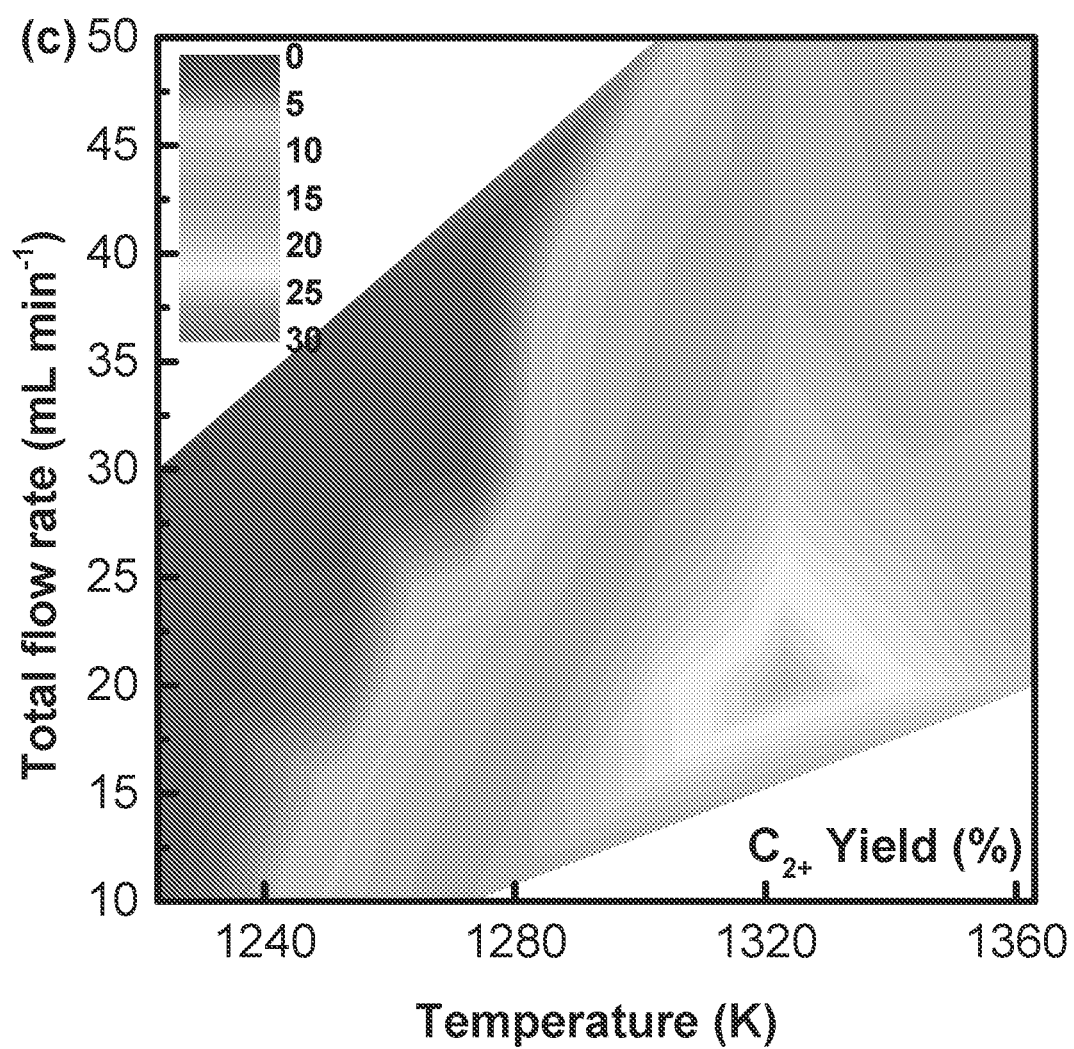
FIG. 3C shows $C_2+$ yields as a function of reaction temperature and feed gas flow rate. ($C_2+$ selectivity and yield and coke yield are calculated from the carbon-atom basis).
Figure 3D:
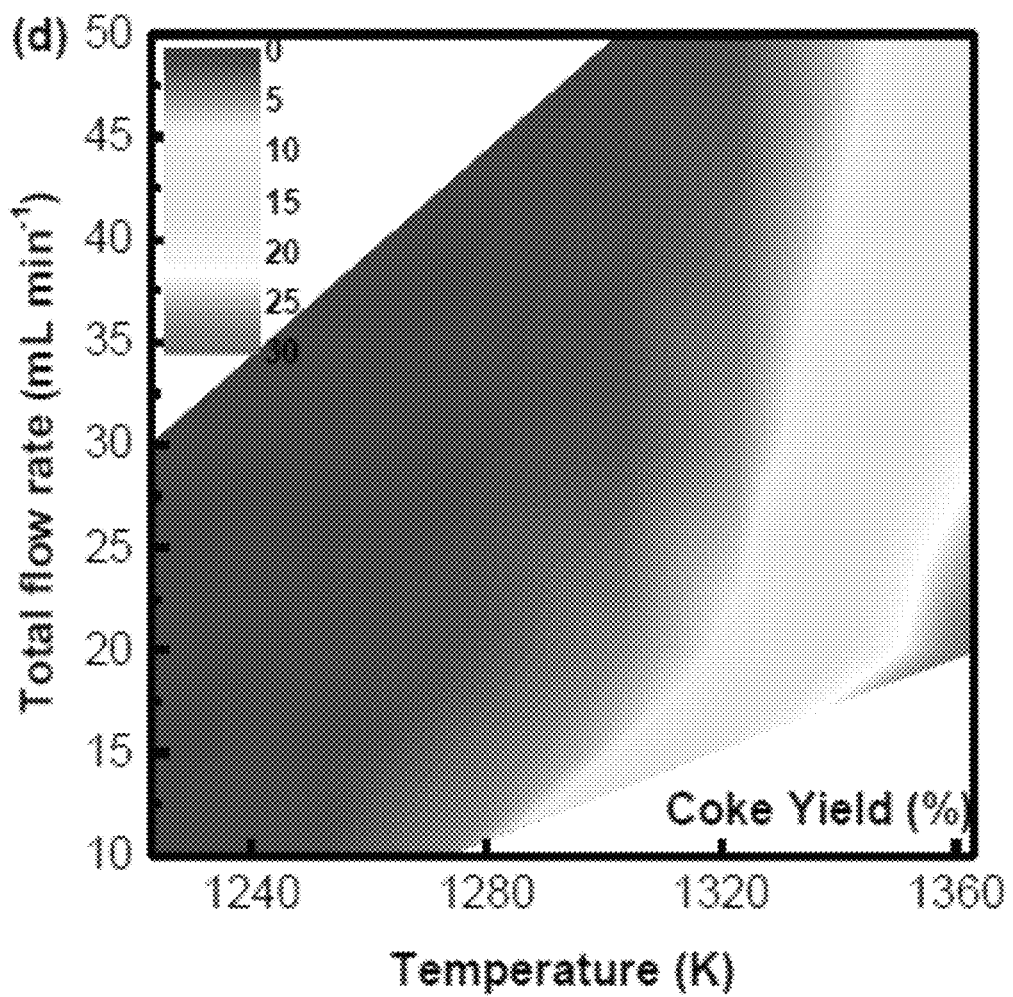
FIG. 3D shows coke yield as a function of reaction temperature and feed gas flow rate. ($C_2+$ selectivity and yield and coke yield are calculated from the carbon-atom basis).

The dependence of CH$_4$ conversion, C$_2$+ selectivity and yields, and coke yield on temperatures and gas flow rates were measured (FIGS. 3A-3D). CH$_4$ conversion increased proportionally with temperature and inversely with gas flow rate (FIG. 3A). The C$_2$+ selectivity (FIG. 3B) has opposite dependence, while C$_2$+ yield shows an increasing and then decreasing trend (FIG. 3C). Coke formation (FIG. 3D) follows the same trend as CH$_4$ conversion. A maximum (25.4%) C$_2$+ yield was achieved at 1323 K and 20 mL min$^{-1}$ gas flow rate, which corresponds to 33.9% CH$_4$ conversion and 25.2% coke selectivity. Both C$_2$ and aromatics are desirable chemicals needed by the petrochemical industry. Although coke is not a popular product, its formation did not deteriorate the DNMC reaction. Tuning the gas flow rate and/or reaction temperature can tune the lighter C$_2$ or heavier aromatic selectivity, for the targeted processes and reactor operation. On the basis of our reactor configuration and coke formation rate, the time required to fill up the reactor by coking is estimated to vary from 98 hours to infinite amount of time (Table 2), which is potentially compatible with the industrial practice.

We carried out the energy balance analysis (FIG. 4), based on standard heat of reaction from DNMC and coke combustion, respectively, to explore the techno-feasibility of autothermal catalytic wall reactor. When CH$_4$ conversion is <20%, the coke yield is <3%. The heat supply for enabling DNMC reaction is higher than heat release from combustion of coke formed in DNMC. Oppositely, when CH$_4$ conversion is >40% and the coke yield is >15%, the heat release from coke combustion is higher than heat supply for DNMC. The energy balance between two reactions can be achieved when DNMC is run at ~33.9% CH$_4$ conversion with 25.4% C$_2$+ yield. A recent agreement framework analysis for DNMC by Maravelias et al.[11] suggests that the economically feasible DNMC is achievable at >25% CH$_4$ conversion, <20% coke formation and low catalyst cost. The DNMC in our catalytic wall reactor sufficiently meet these targets.

Figure 14A:
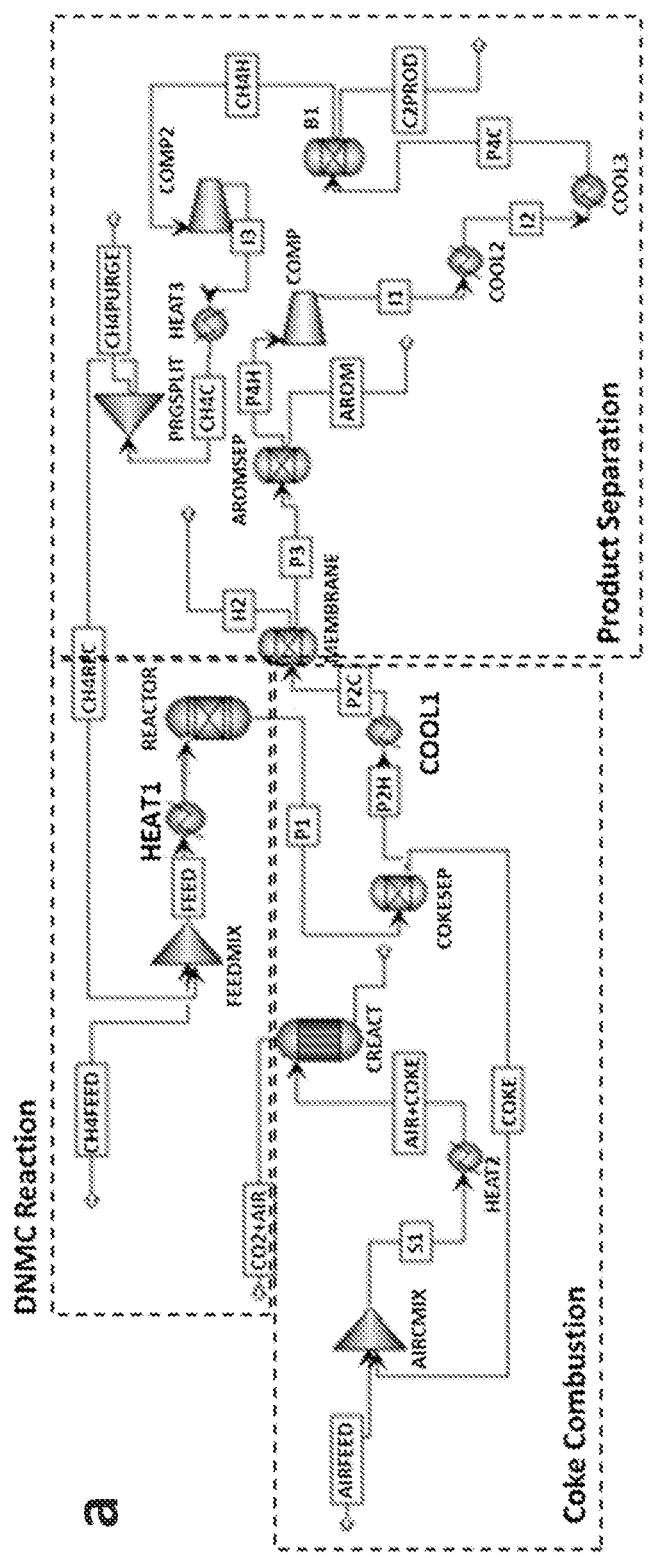
FIG. 14A shows an Aspen Plus (V10) simulation of a DNMC scale-up reaction without incorporating heat integration.

The process simulation using Aspen Plus tools was performed to evaluate the practical implications of the catalytic wall reactor. FIG. 14A presents the flowsheet for DNMC. A heat exchanger was incorporated to utilize heat released from coke combustion to raise the feed stream to reaction temperature, mimicking the autothermal process. The reactor configuration and operation are demonstrated conceptually in FIG. 14B. The Aspen Plus Utilities Object Manager and Economic Solver provided estimates for externally-supplied heating and cooling duties and costs (Tables 3 and 4). These calculations demonstrate a six-fold reduction in supplied energy costs from the autothermal process relative to a conventional system. The DNMC reaction produces multiple industrially-valuable chemicals and fuels—hydrogen, ethylene, benzene and naphthalene—whose production rates are converted into retrievable prices (Tables 5 and 6). These results, in combination with the low costs of CH$_4$ feedstock and reactor material, as well as simple reactor manufacturing process, demonstrate that DNMC in a catalytic wall reactor is an economically feasible and transformative technology for shifting the petrochemical sector to natural gas feedstock in industry.

In summary, a catalytic wall reactor made of a quartz tube and Fe/SiO$_2$(Q) catalyst was created for the first time for DNMC. The performance of the catalytic wall reactor was studied under a range of temperatures in combination in combination with different feed gas flow rates. The obtained performance results form a basis for optimizing reaction conditions towards lighter C$_2$ or heavier aromatic products from CH$_4$ feedstock. The integration of catalyst onto a reactor wall eliminates catalyst packing and discharging steps that occur in the fixed-bed reactor. Coke was formed in the catalytic wall reactor, and its yield varied with the operating conditions, but did not deteriorate the DNMC. The coke formation could enable an autothermal operation of DNMC. The process simulation demonstrates a six-fold reduction in supplied energy costs from the autothermal process with integrated endothermic DNMC and exothermic coke combustion on opposite sides of reactor, relative to a conventional system. The high carbon and thermal efficiencies, low cost in reactor materials and simple reactor manufacturing process are concurrently realized, indicating the great technoeconomic process viability of the DNMC technology.

Materials and Methods

Synthesis of the Fe/SiO$_2$(Q) Catalyst

To synthesize Fe/SiO$_2$(Q) catalyst, fayalite (Fe$_2$SiO$_4$) was first prepared as the iron source using the method reported by DeAngelis et al.[1] The synthesis setup comprised of a 1000 mL three-neck flask equipped with a magnetic stir bar, in which the right and left necks of the flask were sealed with rubber septa, while the middle neck was connected to a condenser that was sealed at the top with a septum. The flask was heated in an oil bath under constant stirring condition to keep the solvent under reflux condition and to ensure even mixing in the synthesis process. The right septum was removed as needed to add reactants and solvents while a needle was inserted through the left septum to deliver argon gas for purging purpose. The reactor setup and the condenser were connected to a circulating cooling bath to condense the evaporated solvents during the synthesis process.

In the synthesis of Fe$_2$SiO$_4$, 375 mL toluene (ACS Reagent 6 grade, Fischer) and 175 mL methanol (ACS Reagent grade, Fisher) were first added to the three-neck flask under magnetic stirring condition. The solution mixture was purged with flowing argon gas (100 mL·min$^{-1}$) for 30 minutes at room temperature. Next, 8.7 g of iron (II) chloride (FeCl$_2$, 99.5% metal basis, Alfa Aesar) and 9.3 g of sodium ethoxide (NaOC$_2$H$_5$, 96%, Acros) were added to the liquid mixture in the flask in sequence. The mixture was then heated to refluxing condition. During the ramping process, 7.9 g tetraethyl orthosilicate (TEOS, 98% purity, Sigma-Aldrich) was added to the mixture. The mixture was kept under refluxing condition for another 30 minutes. Lastly, 10 mL of 0.2 M NaOH (99%, Sigma-Aldrich) solution was added to the mixture via a syringe pump (New Era Pump Systems NE-1000) at a flow rate of 0.5 mL·min$^{-1}$. After the addition, the mixture was continued to stir under reflux condition for 12 hours. After 12 hours, the heating plate was turned off and the mixture was cooled down to room temperature. The flask was continuously purged by Argon gas throughout the whole synthesis process.

The gel-like mixture in the flask was transferred to a rotary evaporator (Heidolph Laborota 4000) to remove solvents. The powdered sample formed was then calcined in a tube furnace (National Electric Furnace FA120 type) for 4 hours under flowing nitrogen gas (100 mL min$^{-1}$) at 1073 K with a ramp rate of 5 K min$^{-1}$. After calcination, the Fe$_2$SiO$_4$ was washed and centrifuged with hot (~353 K) deionized H$_2$O to remove NaCl. The washing and centrifugation steps were repeated five times. Finally, the Fe$_2$SiO$_4$ sample was rinsed with methanol and dried with rotary evaporator. The mixture was then loaded into the center of a quartz tube (6.35 mm in outer diameter and 5.00 mm in inner diameter) and heated in a hydrogen/oxygen (H$_2$/O$_2$) flame using a torch (3A blow pipe). The tube softened and the packed particles stuck to each other. Once the quartz tube was cooled, the tube was broken down and the packed particles were collected as the Fe/SiO$_2$(Q) catalyst. The Fe/SiO$_2$(Q)

catalyst was crushed and ground to fine powder for the catalysis tests and deposition on the wall of quartz tube to form catalytic wall reactor.

Manufacturing of Catalytic Wall Reactor

The catalytic wall reactor was manufactured by heating the center of a 457 mm in length and 6.35 mm in outer diameter quartz tube to its melting temperature (1973 K) with a torch (3A blow pipe) flowing hydrogen and oxygen. The softened part of the quartz tube was then curved 180 degrees to form a "U" shape. To make the catalytic wall reactor, the as-synthesized Fe/SiO$_2$(Q) catalyst in fine powder form was packed into the U-shape quartz tube. Both the Fe/SiO$_2$(Q) catalyst and quartz tube were then heated to ~1973 K to fuse the Fe/SiO$_2$(Q) catalyst to the wall of the quartz tube. This step was repeated several times to make sure the Fe/SiO$_2$(Q) catalyst was uniformly dispersed and fully embedded into the wall of the quartz tube. The leftover Fe/SiO$_2$(Q) catalyst that was not fused into the reactor wall was taken out. Eventually, the reactor with a flow channel and catalyst on inner wall was prepared for the catalysis tests.

Characterization

The crystallinity of the catalysts was examined by powder X-ray diffraction (XRD) patterns using a Bruker D8 Advance Lynx Powder Diffractometer (LynxEye PSD detector, sealed tube, Cu Kα radiation with Ni β-filter). N$_2$ adsorption-desorption isotherms of the samples were measured using an Autosorb-iQ analyzer (Quantachrome Instruments) at 77 K. The specific surface areas of the samples were determined using (Brunauer, Emmett and Teller) (BET) method. The Fe composition of the catalyst was determined by inductively coupled plasma optical emission spectroscopy (ICP-EOS, Optima 4300DV Instrument, Perkin-Elmer). The amount of coke deposited on the Fe/SiO$_2$ catalyst obtained from setting (ii) in FIG. 2A was investigated on a thermo-gravimetric analyzer (TGA) (Shimadzu, TGA-50). In the TGA analysis, the temperature was increased to 1273 K under flowing air (50 mL min$^{-1}$, breathing grade, Airgas) at a ramp rate of 10 K min$^{-1}$. The amount of coke formed on the catalytic wall reactor was examined using temperature-programmed oxidation (TPO). Typically, the coked catalytic wall reactor was placed inside a temperature-controlled furnace. The temperature of the furnace was held constant by a Eurotherm Controller (2408 series). The catalyst temperature was monitored by a K-type thermocouple attaching to the outer wall of the catalytic wall reactor. The furnace was ramped to 1123 K at a ramp rate of 10 K min$^{-1}$ under flowing He (35 mL min$^{-1}$, ultrapure, Airgas) and O$_2$ (5 mL min$^{-1}$, ultrapure, Airgas) atmosphere. The O$_2$-TPD profile was recorded using a mass spectrometer (ABB Extrel) during this step.

DNMC Reaction Tests

DNMC Reaction in Fixed-Bed Reactor

The DNMC reaction was performed in a non-active U-shape quartz reactor under atmospheric pressure and at 973 K. Typically, 0.375 g of Fe/SiO$_2$(Q) was loaded into the quartz reactor in which the reactor was placed inside a temperature-controlled furnace (National Electric Furnace FA120 type). The temperature of the furnace was held constant by a Watlow Controller (96 series). The catalyst temperature was monitored by a K-type thermocouple attaching to the outer wall of the reactor. The catalyst was heated in N$_2$ atmosphere (20 mL min$^{-1}$, ultrapure, Airgas) to the desired reaction temperature prior to the DNMC reaction. CH$_4$ (research grade, Airgas) and N$_2$ (ultrapure, Airgas) were then introduced to the reactor at a total gas flow rate of 20 mL min$^{-1}$ (10% N$_2$ internal standard). The product effluents were analyzed on-line using gas chromatograph (Agilent Technologies, 6890N) equipped with ShinCarbon ST packed column connected to a TCD and DB-WAX column connected to a FID to determine methane conversion and product selectivity.

DNMC Reaction in Catalytic Wall Reactor

Same experimental setup as that of fixed-bed reactor was used to perform DNMC reaction in catalytic wall reactor. After the catalytic wall reactor was heated in N$_2$ atmosphere (20 mL min$^{-1}$, ultrapure, Airgas) to the desired reaction temperature, CH$_4$ (research grade, Airgas) and N$_2$ (ultrapure, Airgas) were then introduced to the reactor. The reaction was run at a temperature range of 1223 K-1363 K and at a total gas flow rate range of 10 to 50 mL min$^{-1}$.

Characterization and DNMC Performance Results

Catalyst Properties

Figure 6A:
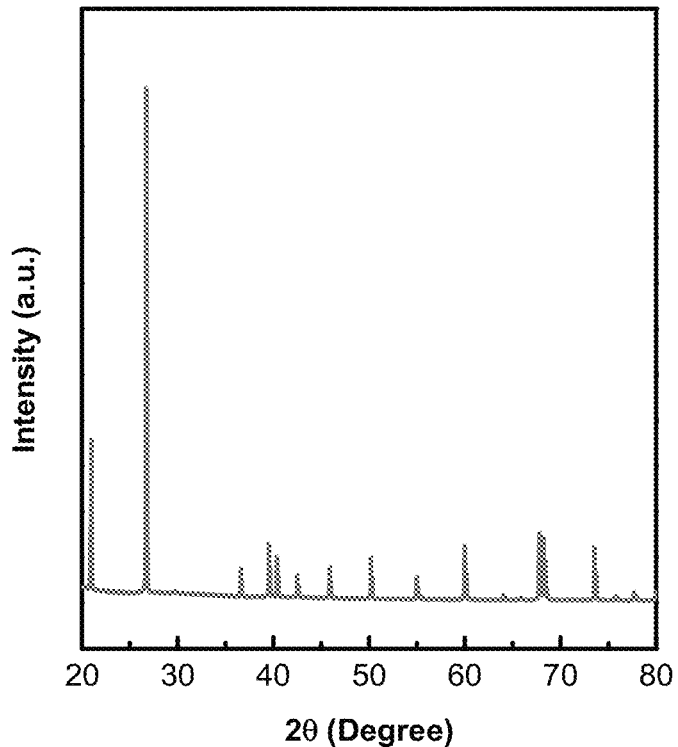
FIG. 6A shows an XRD pattern of the $Fe/SiO_2(Q)$ catalyst used for catalytic wall reactor in the DNMC reaction.
Figure 6B:
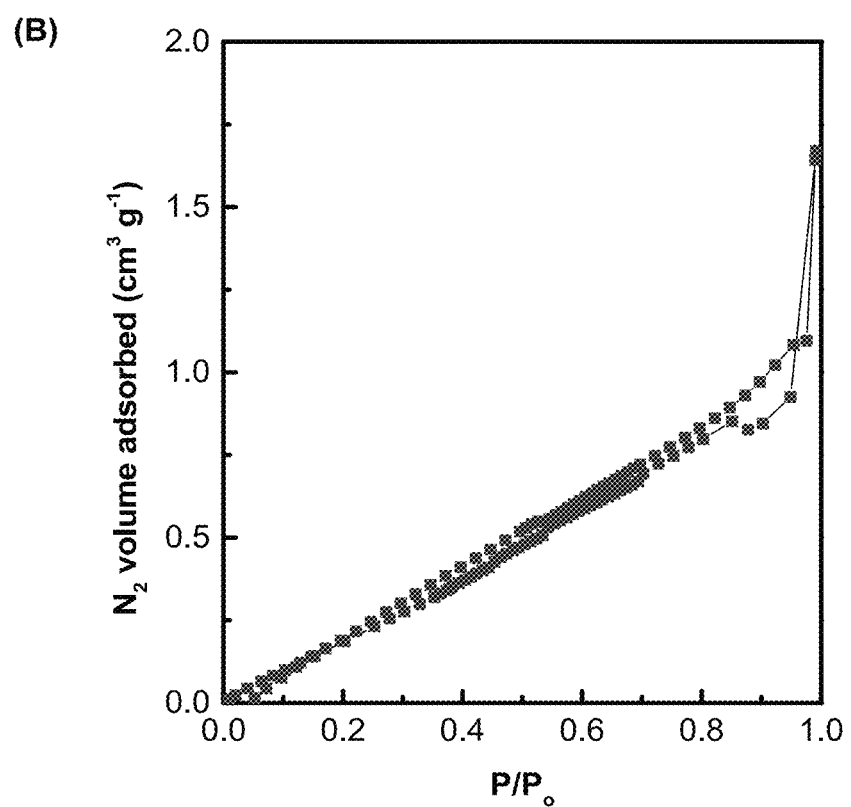
FIG. 6B shows a $N_2$ adsorption/desorption isotherm of the $Fe/SiO_2(Q)$ catalyst used for catalytic wall reactor in the DNMC reaction.
Figure 7A:
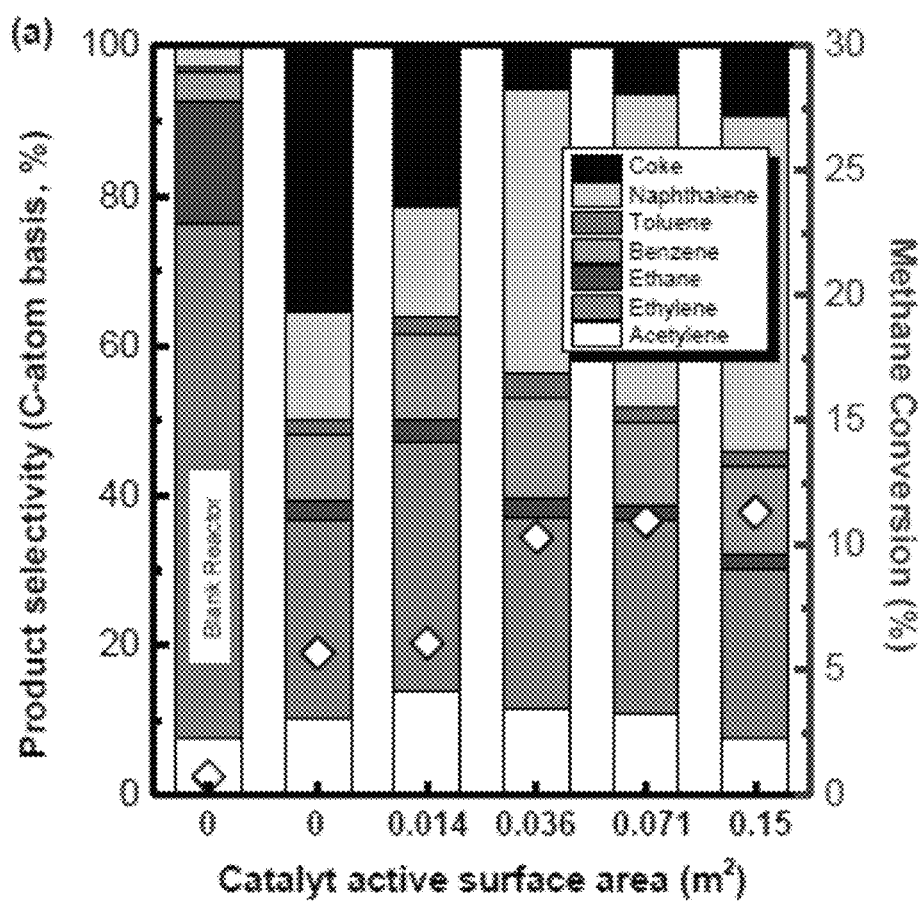
FIG. 7A shows methane conversion and product selectivity versus catalyst surface area (or mass) in a fixed-bed reactor with fixed catalyst bed length by quartz balance particles when catalyst quantity was varied (Reaction temperature=1273 K, total gas flow rate=20 mL min$^{-1}$, $CH_4:N_2=9:1$, 1 atm pressure, Fe concentration in $Fe/SiO_2(Q)$=0.075 wt %, $Fe/SiO_2(Q)$ catalyst usage: blank, 0.000, 0.035, 0.090, 0.178, and 0.375 g in sequence in the plot).
Figure 7B:
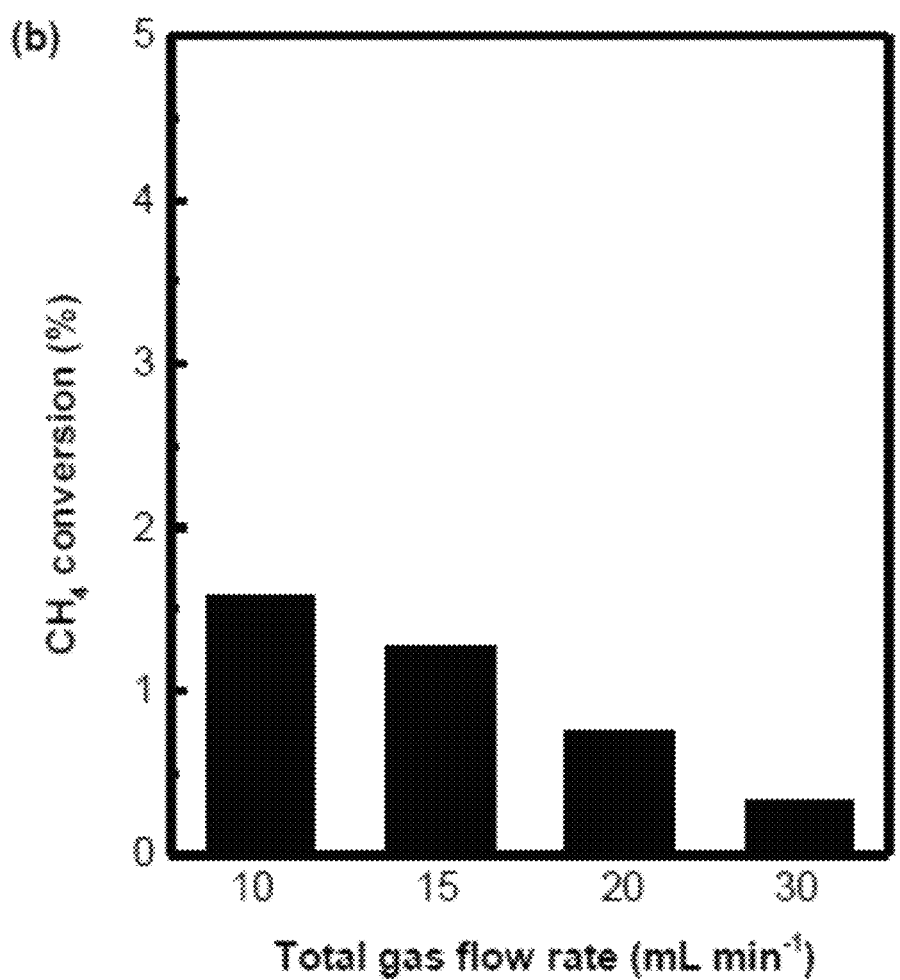
FIG. 7B shows methane conversion and product selectivity of DNMC reaction in non-active quartz tube as a function of total flow rate at 1273 K ($CH_4:N_2=9:1$, 1 atm pressure).
Figure 8:
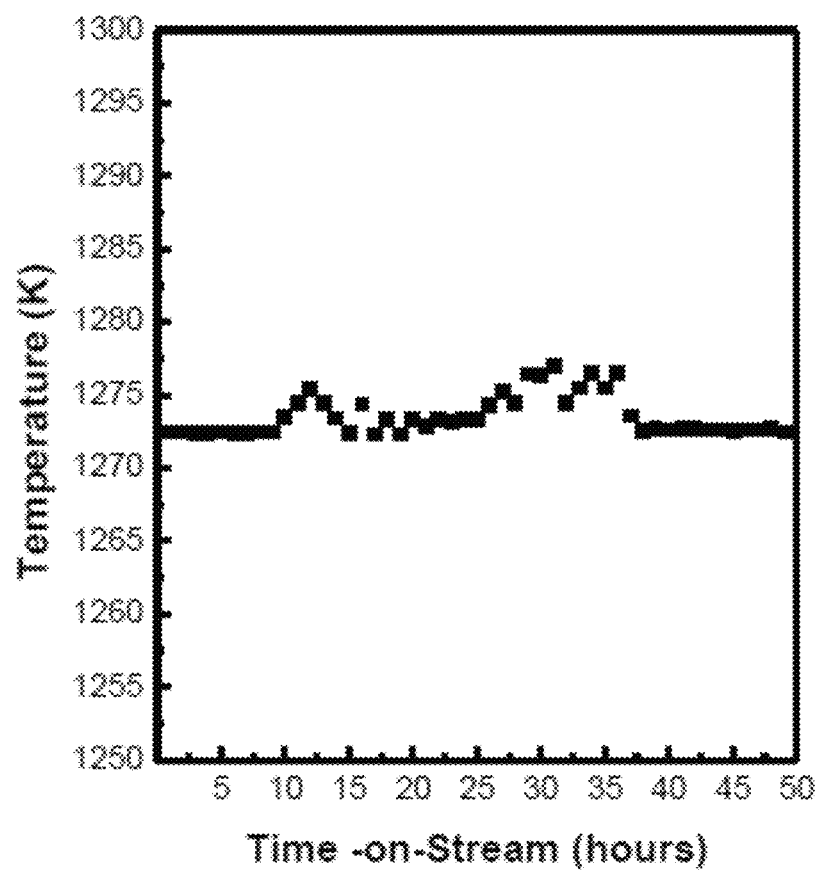
FIG. 8 shows a temperature profile during the 50-hour long-term stability test of DNMC reaction in catalytic wall reactor presented in FIG. 2B.

The XRD pattern in FIG. 6A shows the crystalline phase of SiO$_2$ (α-quartz) in the Fe/SiO$_2$(Q) sample. Neither Fe nor FeO$_x$ diffraction peaks were observed in the XRD pattern, hinting that only very small amount of Fe was present in the catalyst. FIG. 6B shows the N$_2$ adsorption/desorption isotherm of the Fe/SiO$_2$(Q) sample. The surface area of the catalyst was found to be 0.38 m$^2$·g$^{-1}$.

Catalytic Wall Reactor Properties

Residence Time Analysis

A simple dimensional calculation was performed to estimate the diffusion time of reactant to the catalytic wall reactor[2]. The time for diffusion, t to the reactive wall in laminar flow is approximated as $$t \cong \frac{(x/2)^2}{D} \cong \frac{(4.31 \text{ mm}/2)^2}{10 \text{ mm}^2/s} = 0.046 \text{ s}$$

where x is the inner diameter (4.31 mm) of the catalytic wall reactor and D is the methane diffusion coefficient estimated to be 10 mm$^2$ s$^{-1}$ at reaction temperatures. Therefore, the diffusion time of the reactant to the catalytic wall is much shorter than the experimental residence time.

Blank (Non-Active) Reactor Performance

Control experiments were performed by running DNMC reactions in a non-active quartz reactor at 1273 K at total gas flow rate range of 10-30 mL min$^{-1}$. The result showed that methane conversion was kept below 2% when there was no active species deposited onto the wall of the reactor (FIG. 2A).

Long-Term Stability Test

A positive spike in benzene/toluene selectivity and negative spike in naphthalene selectivity at ~10 and 30 hours on stream were observed in the reproducibility tests. Such behavior originated from the slight periodic temperature fluctuation with time-on-stream (TOS) during the DNMC reaction. The periodic fluctuation originated from the temperature program setting in the temperature controller (Omega Engineering Inc., Catalog #: CN7823). There were 8 ramp/soak segments in the temperature program. The maximum time duration of each soak segment was 15 hours. Since the long-term stability tests were carried out for 50-hour, three soak segments were needed in the entire tests. The temperature stability was slightly disturbed during the moment of soak temperature segment transition. The DNMC reaction was started ~3-4 hours after the first soak segment. Since the transition from the first temperature soak segment to the second one happened at ~11-12 hours of the reaction, first spike was observed in FIG. 2B. The second spike appeared at ~30 hours of the TOS in FIG. 2B, which corresponded to the transition from the second soak segment to the third one in the temperature program.

Reproducibility Study on the 50-Hour Long-Term Stability Test

Figure 9A:
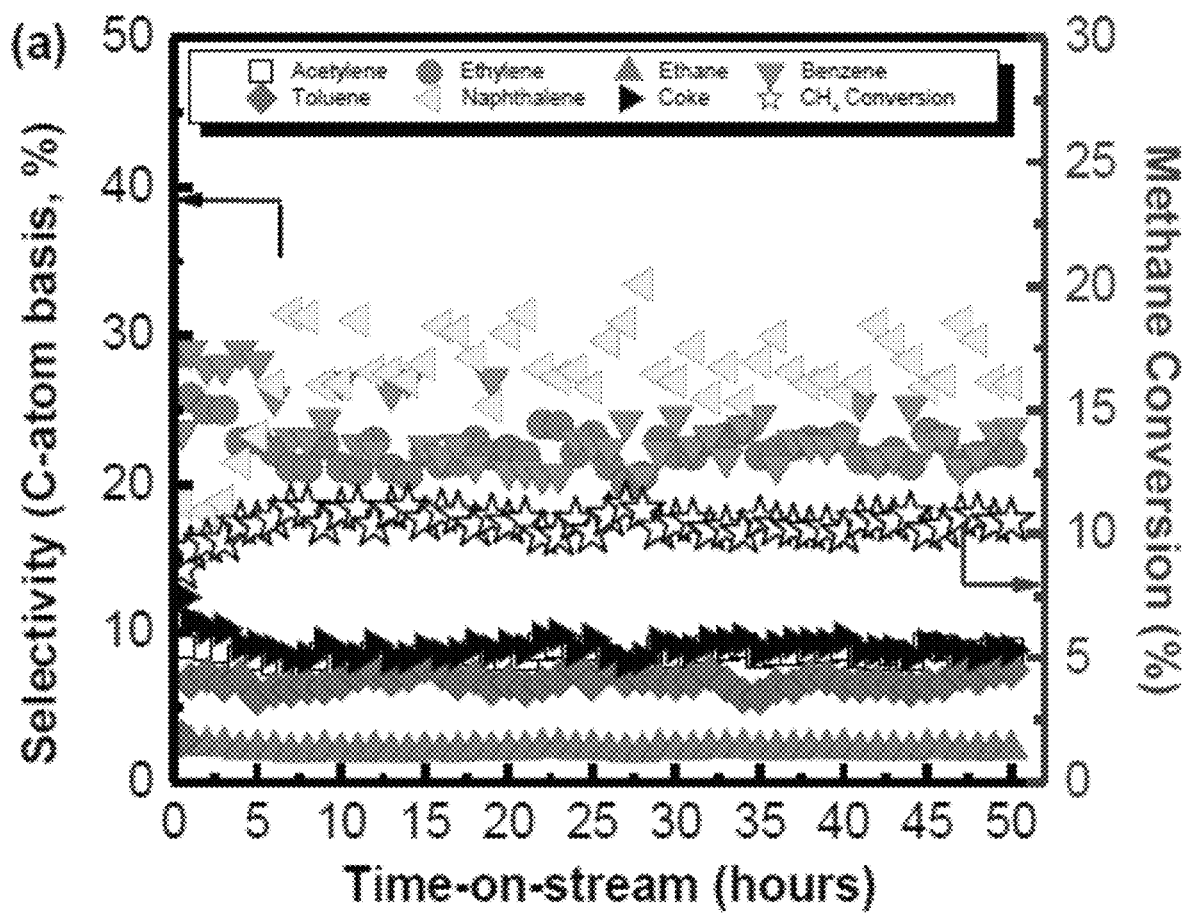
FIG. 9A shows a long-term stability test of the DNMC reaction in a catalytic wall reactor made from the same synthesis process as that used in FIG. 2B (1273 K, 20 mL min$^{-1}$ gas flow rate, $CH_4:N_2=9:1$ ($N_2$: internal standard), 1 atm pressure, 0.075 wt % Fe in $Fe/SiO_2(Q)$).
Figure 9B:
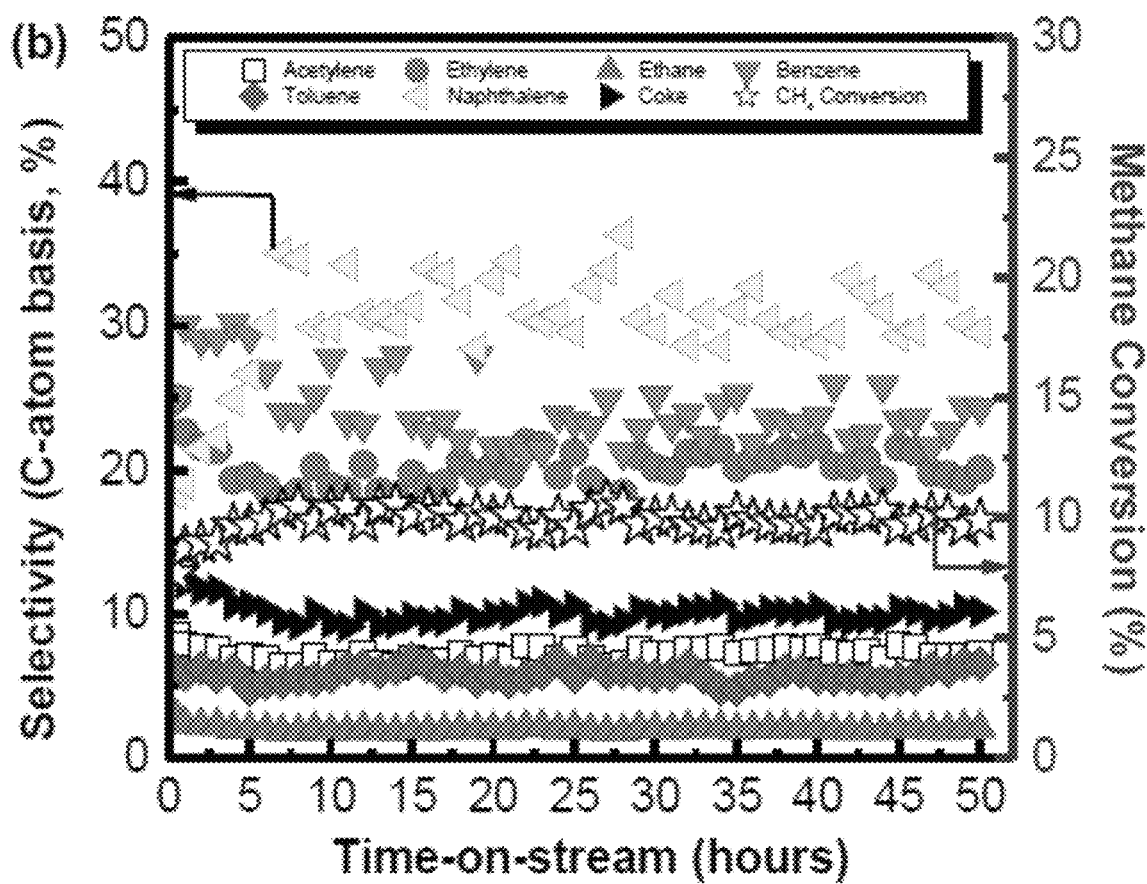
FIG. 9B shows a long-term stability test of the DNMC reaction in a different catalytic wall reactor made from the same synthesis process as that used in FIG. 2B. (1273 K, 20 mL min$^{-1}$ gas flow rate, $CH_4:N_2=9:1$ ($N_2$: internal standard), 1 atm pressure, 0.075 wt % Fe in $Fe/SiO_2(Q)$).
Figure 9C:
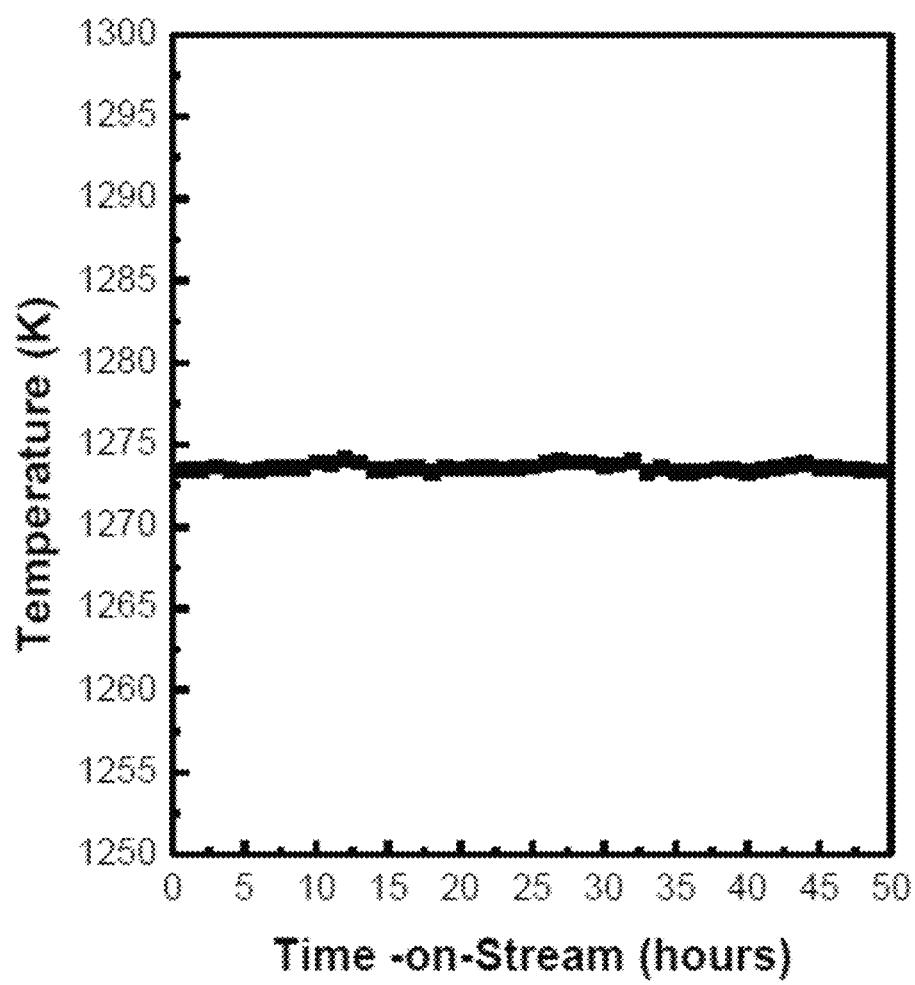
FIG. 9C shows a temperature profile during the repeated 50-hour long-term stability test presented in FIG. 9A.
Figure 9D:
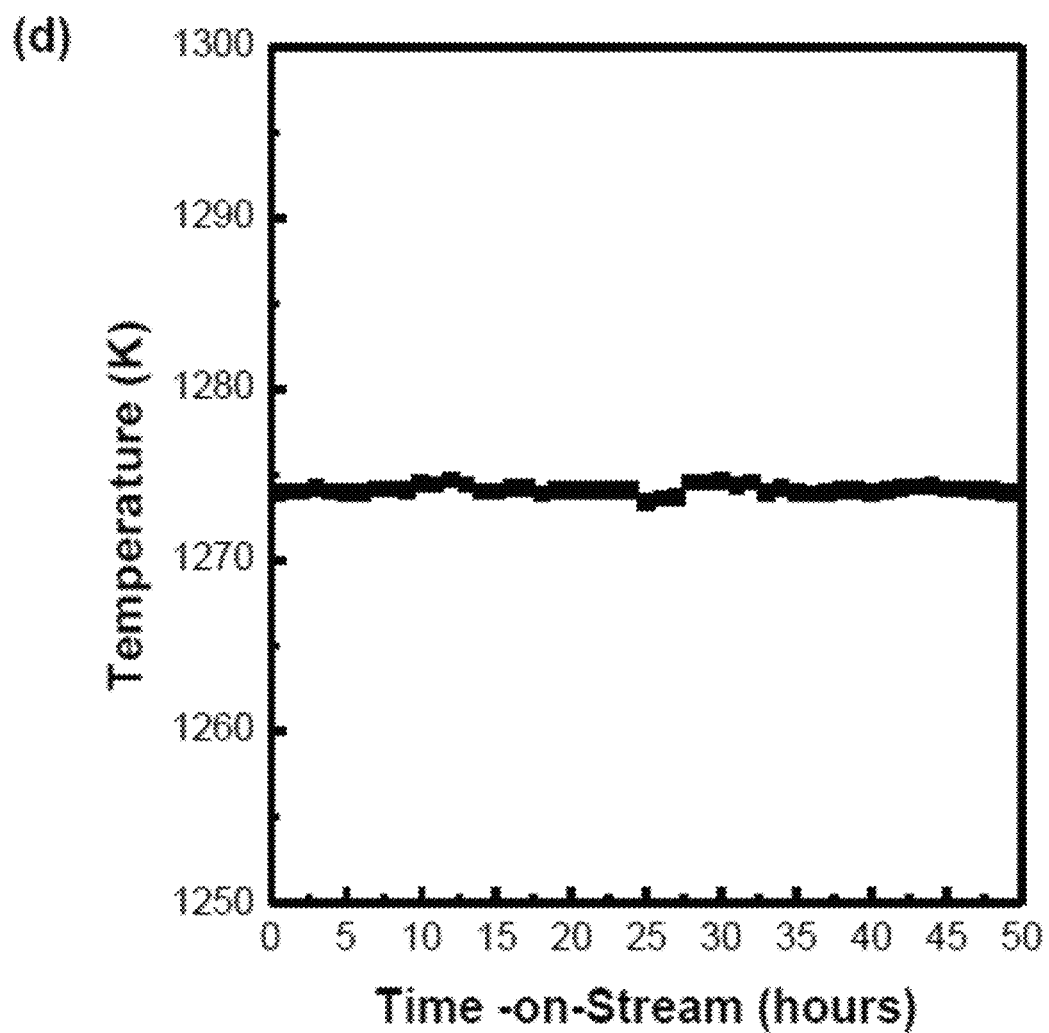
FIG. 9D shows a temperature profile during the repeated 50-hour long-term stability test presented in FIG. 9B.

A reproducibility study on the 50-hour long-term stability test was performed with another two catalytic wall reactors that were made following the same procedure, and the results are shown in FIGS. 9A-9C. The long-term stability data shows that the DNMC performance was reproducible even with different catalytic wall reactors in multiple tests. The temperature profile for these two sets of reaction data was shown in FIG. 9C and FIG. 9D. The slight instability in the reaction temperatures shown in these two figures was minimized in these tests, so that slight spikes in the reaction data in FIG. 2B were not clearly seen in FIGS. 9A-9D.

Coke Formation Analysis in Catalytic Wall Reactor

Methods to Quantify Total Amount of Coke Formed in DNMC Reaction

The amount of coke formed in the catalytic wall reactor was determined by three methods: (i) weight-difference, (ii) TGA and (iii) TPO. For the weight difference method, before loading the reactor to the reactor system, the weight of the clean catalytic wall reactor was measured. After the DNMC reaction at each reaction condition was done, the weight of the catalytic wall reactor with now coke deposited on it was measured again. The difference in weight of the catalytic wall reactor was regarded as the amount of coke formed during the DNMC reaction. One example of coke formation rate quantified using weight difference method is shown below.

Method 1: Weight-Difference Method
Sample Calculation of Coke Formation Rate Using Weight-Difference Method:
Reaction condition: 1273 K, 20 mL min$^{-1}$, total reaction time=4 hours
Mass of reactor before DNMC reaction: 19.6837 g
Mass of reactor after DNMC reaction: 19.7002 g $$\text{Average coke formation rate} = \frac{19.7062\ g - 19.6837\ g}{240\ \text{minute} * 12\ g/mole} = 7.81 \times 10^{-6}\ \text{mole min}^{-1}$$

TGA

The TGA profile of the Fe/SiO$_2$(Q) powder obtained from setting (ii) in FIG. 2B is shown in FIG. 10. The weight loss in the temperature range of 835 K to 945 K in FIG. 10 reveals the burning-off of the coke deposited on Fe/SiO$_2$(Q) catalyst. A total weight loss of 2.86% was observed on the catalyst after 4 hours of DNMC reaction, which is equivalent to 8.51×10$^{-6}$ mole min$^{-1}$ of coke formation rate.

TPO

TPO of the catalytic wall reactor was performed to check the feasibility of weight-difference method to quantify coke. FIG. 11 shows the TPO profiles of catalytic wall reactor after 4 hours of DNMC reaction while Table 1 presents the amount of O$_2$ consumed and CO and CO$_2$ generated during the TPO process.

TABLE 1

Amount of O$_2$ consumed and products formed during TPO process.

| Gases | Concentration (moles) | Consumption/Formation rate over TOS = 4 hours (moles/min) |
|---|---|---|
| O$_2$ | 1.80 × 10$^{-3}$ | 7.48 × 10$^{-6}$ |
| CO$_2$ | 1.85 × 10$^{-3}$ | 7.72 × 10$^{-6}$ |
| CO | 4.70 × 10$^{-8}$ | 1.96 × 10$^{-10}$ |

From the TPO results, the coke formation rate in the catalytic wall reactor over the course of 4 hours during DNMC reaction was ~7.60×10$^{-6}$ mole min$^{-1}$ (average of O$_2$ consumption rate and CO$_2$ and CO formation rates). Since the coke formation rate determined from TPO method is similar to the coke formation rate determined from weight-difference method (7.81×10$^{-6}$ mole min$^{-1}$), we employed the weight-difference method in all our catalytic performance data analysis later on.

Time Required for Coke to Completely Fill Up the Catalytic Wall Reactor

We estimated the amount of time required for the coke to completely fill up the reactive reactor at each reaction conditions, and the results are shown in Table 2. The coke growth rate was assumed to be uniform throughout the wall of the catalytic wall reactor. One example of time required calculation is shown below.

Sample Calculation of Time Required to Completely Fill Up the Reactor:
Reaction temperature: 1303 K
Gas flow rate: 30 mL min$^{-1}$
Volume of catalytic wall reactor: 8.11 cm$^3$
Density of coke: 2.267 g cm$^{-3}$
Mass of coke formed in 2.5 hours: 0.0318 g $$\text{Volume of coke formed in 2.5 hours:}\ \frac{0.318\ g}{2.267\ g/cm^3} = 0.013\ cm^3$$

Therefore, the time taken to completely fill up the catalytic wall reactor is 1445 hours.

Time Required for Coke to Completely Fill Up the Catalytic Wall Reactor

We estimated the amount of time required for the coke to completely fill up the reactive reactor at each reaction conditions, and the results are shown in Table 2. The coke growth rate was assumed to be uniform throughout the wall of the catalytic wall reactor. One example of time required calculation is shown below.

Coke Formation Rate Versus Time-On-Stream

Figure 12A:
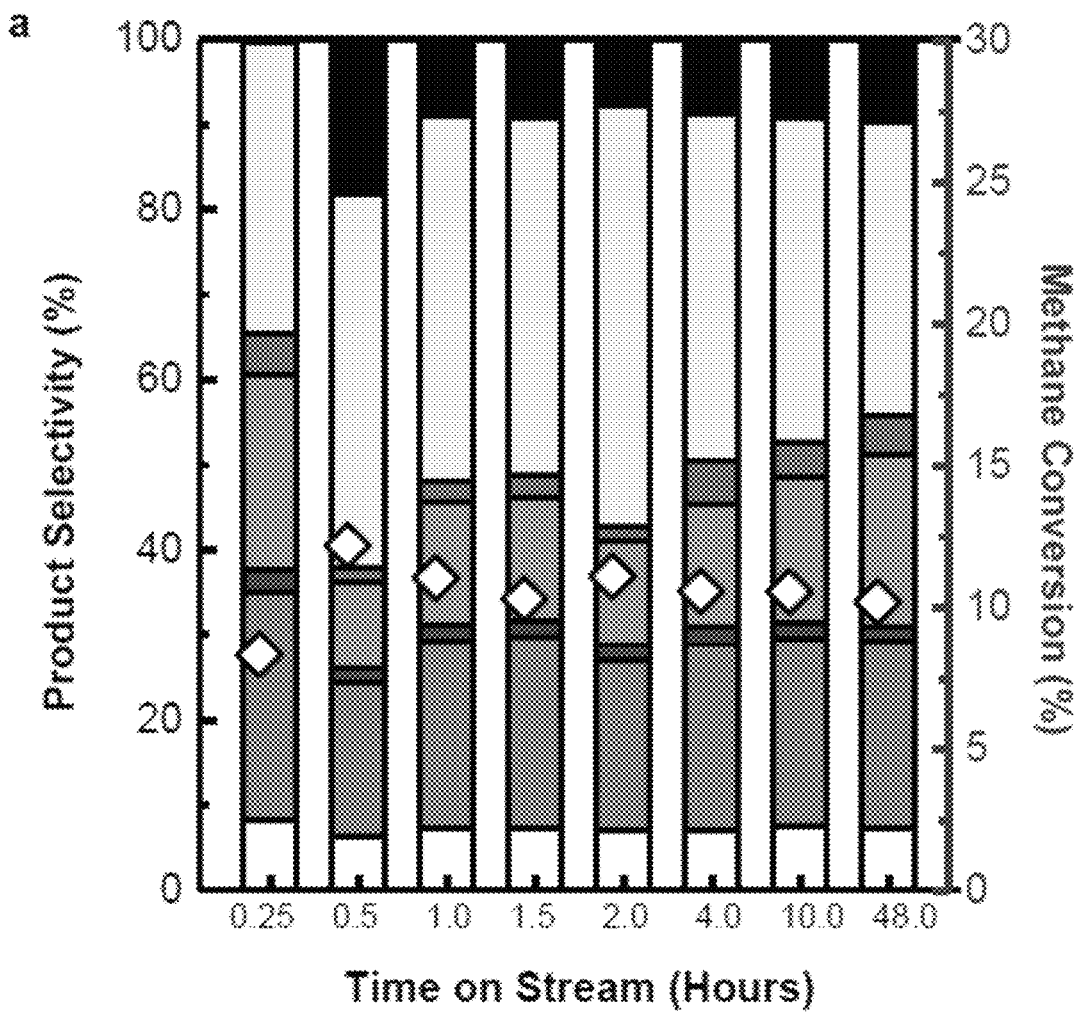
FIG. 12A shows methane conversion as a function of time on stream at 1273 K (total flow rate=20 mL min−1, $CH_4:N_2=9:1$, 1 atm pressure).
Figure 12B:
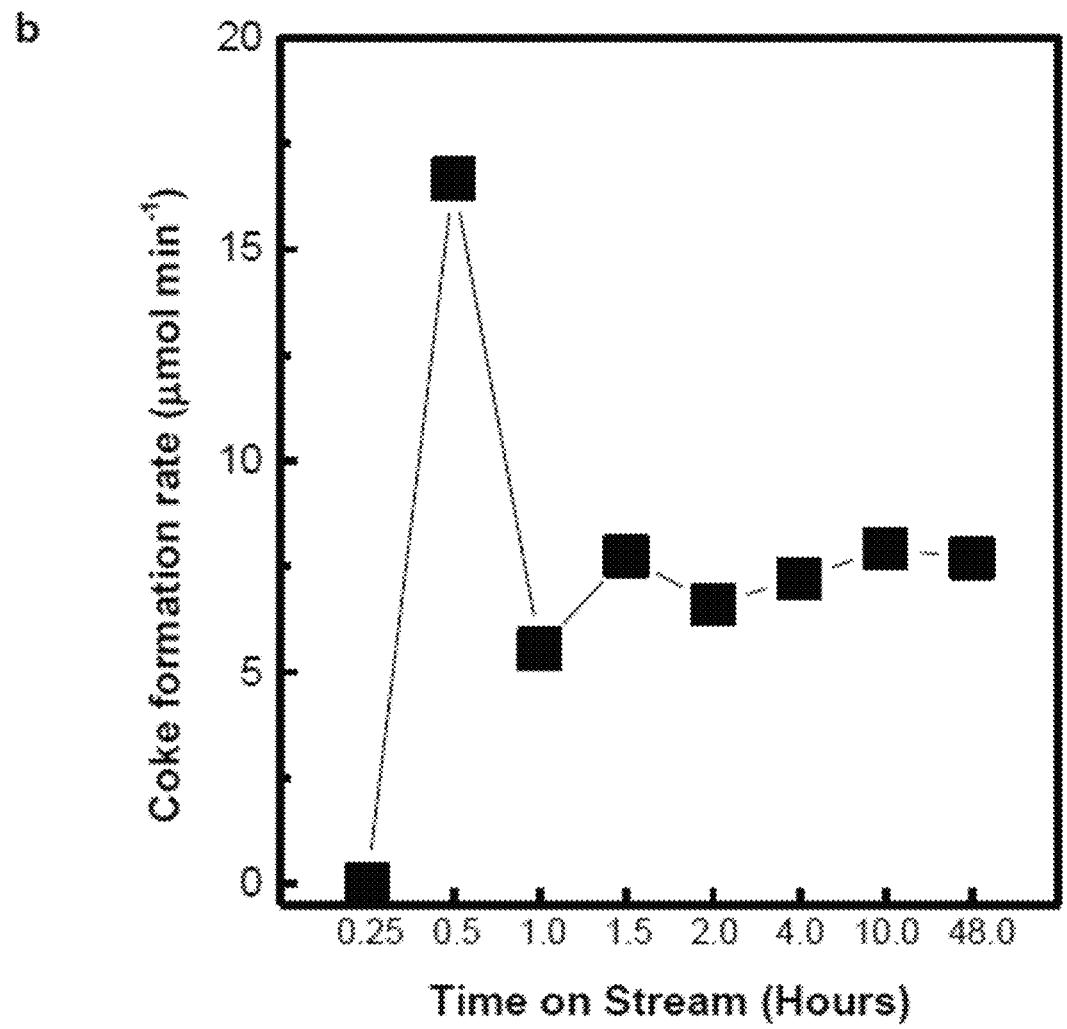
FIG. 12B shows coke formation rate as a function of time on stream at 1273 K (total flow rate=20 mL min−1, $CH_4:N_2=9:1$, 1 atm pressure).

The coke formation rate in the Fe/SiO$_2$(Q)-based catalytic wall reactor was also studied over the course of 50-hours and the results are shown in FIGS. 12A-12B. The coke formation rate increased significantly from TOS=0 hour to TOS=0.25 hours. After 0.25 hours, the coke formation rate started to decrease until it reached a plateau starting from TOS=1.0 hour onward.

Heat of Reaction Analysis for Autothermal Catalytic Wall Reactor

Analysis of Energy Input for DNMC Reaction and Energy Release from Coke Combustion The energy balance analysis was performed to explore the techno feasibility of autothermal catalytic wall reactor for DNMC. The analysis was simply based on the standard heat of reaction (ΔH°) calculation from each product formation reaction equation at each reaction temperature. Standard heat-capacity (ΔC°) was assumed to be independent of temperature.

Sample Calculation of Heat Required for DNMC and Heat Released by Coke Combustion Reactions:
Reaction temperature: 1323 K
Gas flow rate: 20 mL min−1
Methane in feed: 1 mole basis

| Methane Conversion (%) | Acetylene Selectivity (%) | Ethylene Selectivity (%) | Ethane Selectivity (%) | Benzene Selectivity (%) | Toluene Selectivity (%) | Naphthalene Selectivity (%) | Coke Selectivity (%) |
|---|---|---|---|---|---|---|---|
| 33.9 | 3.8 | 12.7 | 0.77 | 16.9 | 1.05 | 39.7 | 25.1 |

Product Formation Reaction Equation from DNMC:
(1) $CH_4 \rightarrow \frac{1}{2} C_2H_2 + \frac{3}{2} H_2$
(2) $CH_4 \rightarrow \frac{1}{2} C_2H_4 + H_2$
(3) $CH_4 \rightarrow \frac{1}{2} C_2H_6 + \frac{1}{2} H_2$
(4) $CH_4 \rightarrow 1/6 C_6H_6 + 3/2 H_2$
(5) $CH_4 \rightarrow 1/7 C_7H_8 + 10/7 H_2$
(6) $CH_4 \rightarrow 1/7 C_{10}H_8 + 8/5 H_2$
(7) $CH_4 \rightarrow C + 2H_2$ We assumed that the coke is mainly comprised of carbon, so the product formation reaction equation from coke combustion in air is:

$$C + O_2 \rightarrow CO_2 \quad (1)$$

Thermal Properties of Gases:

| Gas | Heat capacity (J mol$^{-1}$ K$^{-1}$)$^a$ | Enthalpy of formation (kJ mol$^{-1}$) (298 K, 1 atm)$^a$ |
|---|---|---|
| $H_2$ | 29.1 | 0 |
| $O_2$ | 29.3 | 0 |
| $CH_4$ | 35.7 | −74.5 |
| $C_2H_2$ | 44.2 | 226.9 |
| $C_2H_4$ | 43.7 | 52.51 |
| $C_2H_6$ | 52.7 | −84.7 |
| $C_6H_6$ (g) | 81.7 | 82.9 |
| $C_7H_8$ (g) | 104.4 | 50.0 |
| $C_{10}H_8$ (g) | 133.9 | 150.6 |
| $CO_2$ | 37.2 | −393.52 |
| Coke | 20.8 | 0 |

$^a$Source: *National Standard of Institute and Technology (NIST) Chemistry WebBook*.

The heat of reaction was calculated based on the following equation:

$$\Delta H° = n[\Delta H°_0 + \Delta C°_p(T - T_0)]$$

where n (mole) is the number of moles of product, $\Delta H°_0$ (kJ mol$^{-1}$) is the standard enthalpy of formation, $\Delta C°_p$ (J mol$^{-1}$ K$^{-1}$) is the standard heat capacity, T (K) is the reaction temperature and $T_0$ (K) is the temperature at standard condition.

For reaction (1) from DNMC, $$\begin{aligned}\Delta H_1^o &= n[\Delta H_0^o + \Delta C_p^o(T - T_0)] \\ &= \left(\frac{33.9}{100}\right) * \left(\frac{3.8}{100}\right)\left\{\left[\frac{1}{2} * 226.9 + 0 - (-74.5)\right] * 1000 + \left[\frac{1}{2} * 44.2 + \frac{1}{2} * 29.1 - 35.7(1323 - 298)\right]\right\}/1000 \\ &= 3.82 \text{ kJ mol}^{-1}\end{aligned}$$

Same calculation steps were applied to the rest of the reaction equations for DNMC as well as the reaction equation for coke combustion.

The results for DNMC reaction and the corresponding coke combustion is summarized in Table 2 below.

TABLE 2

Summary of DNMC reaction and the corresponding coke combustion at different reaction conditions.

| Reaction Condition | | $CH_4$ conversion (%) | $C_{2+}$ yield (%) | Coke yield (%) | Heat supplied for DNMC (kJ mol$^{-1}$) | Heat released from coke combustion (kJ mol$^{-1}$) | Time required to fill reactor up by coke (Hours) |
|---|---|---|---|---|---|---|---|
| Temperature (K) | Total gas flow rate (mL min$^{-1}$) | | | | | | |
| 1223 | 10 | 1.7 | 1.7 | 0 | 2.7 | 0 | ∞ |
| | 15 | 0.8 | 0.8 | 0 | 1.3 | 0 | ∞ |
| | 20 | 0.7 | 0.7 | 0 | 0.8 | 0 | ∞ |
| | 30 | 0.5 | 0.5 | 0 | 0.7 | 0 | ∞ |
| 1253 | 10 | 9.5 | 8.3 | 1.2 | 10.3 | −4.7 | 6050 |
| | 15 | 7.4 | 6.8 | 0.6 | 8.2 | −2.3 | 8187 |
| | 20 | 4.2 | 3.9 | 0.3 | 5.3 | −1.2 | 11393 |
| | 30 | 0.9 | 0.9 | 0 | 1.7 | 0 | ∞ |
| 1273 | 10 | 20.4 | 16.4 | 4.0 | 22.1 | −16.4 | 1580 |
| | 20 | 11.2 | 10.1 | 1.1 | 12.6 | −4.3 | 3402 |
| | 30 | 2.5 | 2.3 | 0.1 | 3.4 | −0.6 | 15885 |
| | 40 | 1.3 | 1.3 | 0 | 2.4 | 0 | 0 |
| 1303 | 20 | 26.2 | 22.0 | 4.3 | 28.0 | −17.3 | 743 |
| | 30 | 16.6 | 15.0 | 1.6 | 18.2 | −6.6 | 1445 |
| | 40 | 13.0 | 11.9 | 1.0 | 14.5 | −4.3 | 1782 |
| | 50 | 5.4 | 5.2 | 0.2 | 6.8 | −0.8 | 6967 |
| 1323 | 20 | 33.9 | 25.4 | 8.5 | 34.4 | −34.8 | 362 |
| | 30 | 25.1 | 20.4 | 4.8 | 25.7 | −19.1 | 488 |
| | 40 | 20.8 | 17.9 | 3.0 | 22.4 | −13.8 | 517 |
| | 50 | 18.7 | 17.3 | 1.5 | 19.2 | −5.5 | 984 |
| 1343 | 20 | 40.2 | 22.6 | 17.7 | 44.3 | −71.9 | 190 |
| | 30 | 30.1 | 18.3 | 12.0 | 32.5 | −48.8 | 223 |
| | 40 | 24.8 | 16.2 | 8.8 | 26.6 | −35.6 | 263 |
| | 50 | 21.4 | 15.0 | 6.4 | 22.8 | −26.1 | 355 |
| 1363 | 20 | 49.0 | 19.3 | 30.0 | 55.6 | −121.9 | 98 |

TABLE 2-continued

Summary of DNMC reaction and the corresponding coke combustion at different reaction conditions.

| Reaction Condition | | CH$_4$ conversion (%) | C$_{2+}$ yield (%) | Coke yield (%) | Heat supplied for DNMC (kJ mol$^{-1}$) | Heat released from coke combustion (kJ mol$^{-1}$) | Time required to fill reactor up by coke (Hours) |
|---|---|---|---|---|---|---|---|
| Temperature (K) | Total gas flow rate (mL min$^{-1}$) | | | | | | |
| | 30 | 40.0 | 18.9 | 21.2 | 44.4 | −86.5 | 113 |
| | 40 | 33.2 | 16.6 | 16.7 | 36.9 | −68.0 | 147 |
| | 50 | 29.1 | 15.8 | 14.2 | 37.3 | −57.9 | 198 |

Model Simulations for DNMC Process with Autothermal Catalytic Wall Reactor

Figure 13A:
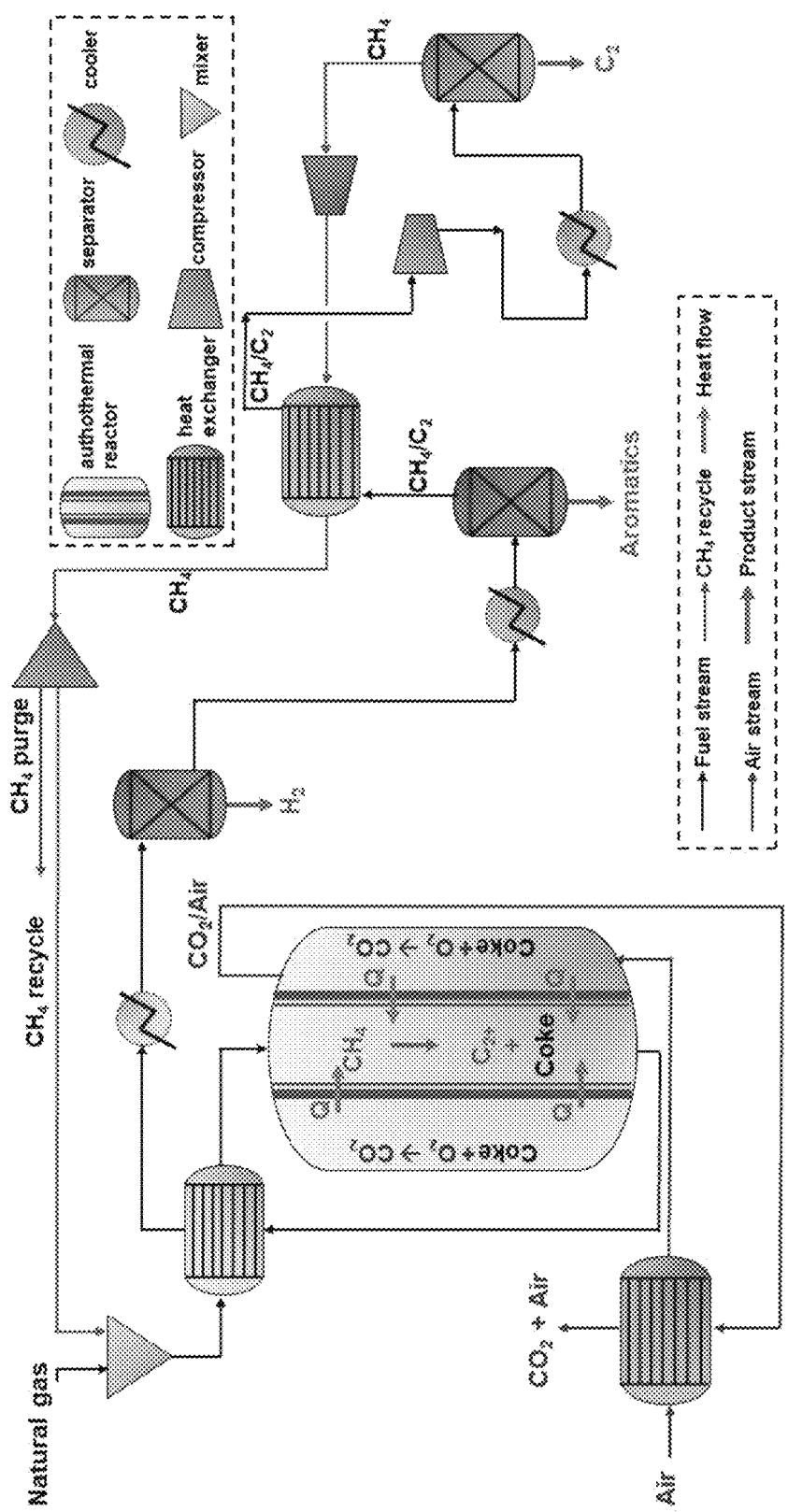
FIG. 13A shows a process flow sheet of DNMC in catalytic wall reactor coupling both endothermic DNMC and exothermic coke combustion, and product separations.
Figure 13B:
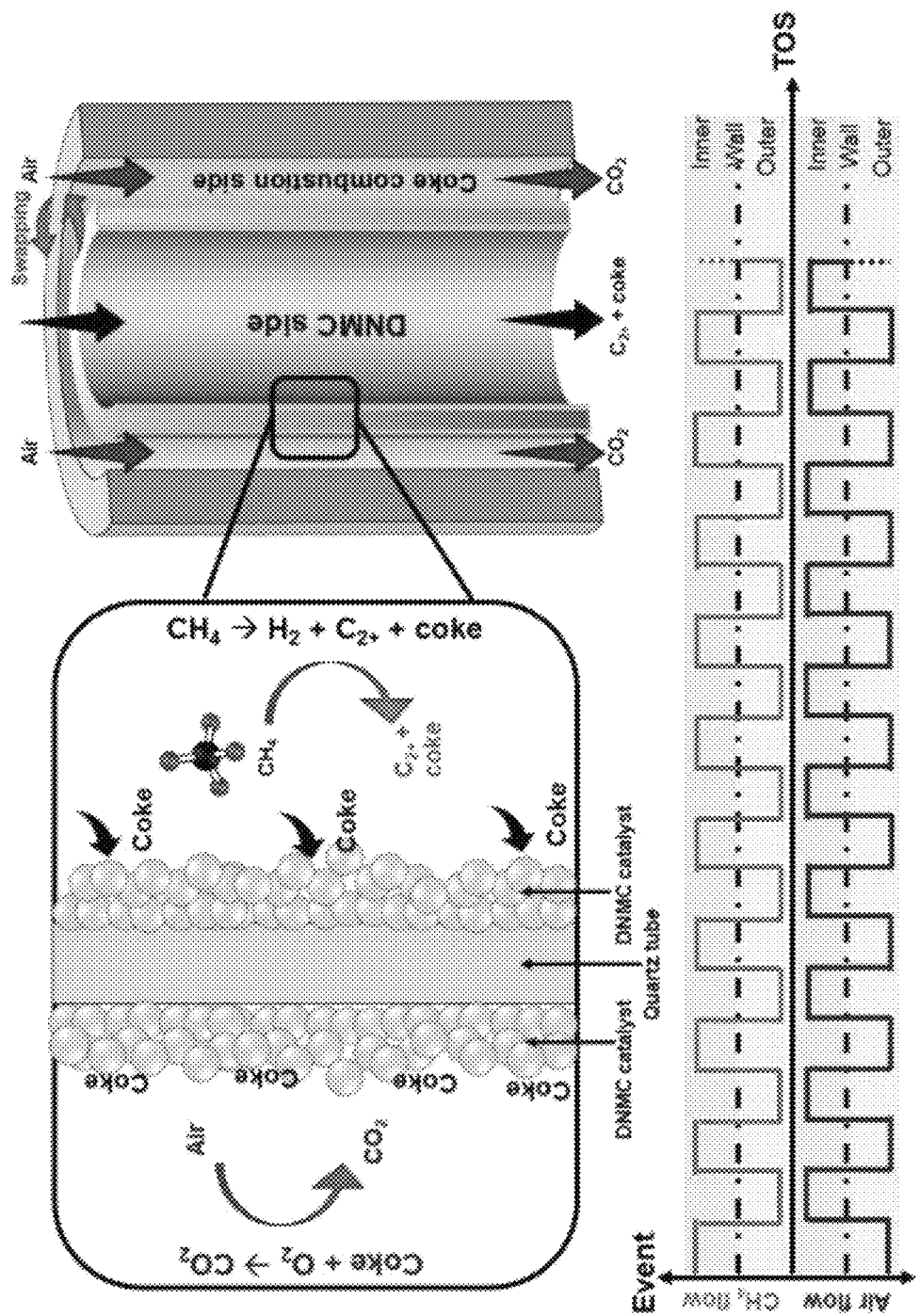
FIG. 13B shows a schematic of DNMC and coke combustion on opposite sides of catalytic wall reactor for autothermal operation in the process simulation process.

The process flowsheet of DNMC in catalytic wall reactor coupling both endothermic DNMC and exothermic coke combustion, and product separations is shown in FIG. 13A. The schematic of the catalytic wall reactor in the process is demonstrated in FIG. 13B. The catalytic wall reactor has catalyst coating layers on both sides of reactor wall, enclosed in a larger diameter housing tube. The inner wall can be firstly used for the DNMC reaction. After an optimal reaction period and coke formation quantity, the DNMC reaction is switched to the opposite side while the inner tube is supplied with air for coke combustion and catalyst regeneration. From now on, the two reactions, endothermic DNMC and exothermic coke combustion, are swapped periodically and thus, achieving autothermal operation of DNMC. The reactor coupling both endothermic DNMC and exothermic coke combustion on opposite sides of reactor wall was considered in the process simulation, as detailed below.

A theoretical scale-up design was simulated in Aspen Plus (V10) to assess the feasibility of the DNMC reaction at an industrial scale. A yield-specific reactor was used to input conversion data based on the experimental reaction results from 1323 K and 20 mL min$^{-1}$ using an initial feed of 1000 kmol/hr. To model the coke combustion process demonstrated in the concentric cylindrical autothermal reactor, an additional separator and reactor following the product stream from the reaction are proposed. The coke-free stream is cooled to 973 K and a hydrogen-permeable membrane is used to separate hydrogen from the product stream without energy-intensive separation units. The resulting hydrocarbon stream is then separated into light (C$_1$ & C$_2$) and heavy (aromatics) hydrocarbons, then the distillate is compressed and enters a demethanizer to separate and recycle methane. FIG. 14A presents this system without using heat integration to obtain the overall energy requirements for the process. Six total heat exchangers using external utilities are required; three use various pressure and temperature steam for heating, two require cooling water, and one requires cryogenic liquid to reduce the temperature significantly for methane/C$_2$ separation. Table 3 shows the heating and cooling duty for each exchanger while Table 4 shows the hourly duties and costs for system operation without heat integration.

TABLE 3

Heating and cooling duties for heat exchangers with and without using heat integration and their hourly costs, respectively.

| | Unit | Heating/Cooling duty (×10$^6$ kJ/hr) | Utility | Utility Cost ($/hr) |
|---|---|---|---|---|
| Without heat integration | COOL1 | −172.5 | Cooling Water | 36.44 |
| | COOL2 | −35.08 | Cooling Water | 7.43 |
| | COOL3 | −6.481 | Liquid Propane | 17.75 |
| | HEAT1 | 10.35 | High Pressure Steam | 389.59 |
| | HEAT2 | 2.145 | High Pressure Steam | 80.89 |
| | HEAT3 | 10.20 | Low Pressure Steam | 19.28 |
| With heat integration (700° C. perovskite H$_2$ separation) | COOL1 | −66.527 | Cooling Water | 14.12 |
| | COOL2 | −19.386 | Liquid Propane | 53.10 |
| | COOL3 | −65.051 | Cooling Water | 13.81 |
| With heat integration (polymer H2 separation membrane) | COOL1 | −305.316 | Cooling Water | 64.82 |
| | COOL2 | −2.2439 | Liquid Propane | 6.15 |

TABLE 4

Hourly duties and costs for system operation with and without heat integration.

| | Without heat integration | With heat integration (700° C. perovskite H$_2$ separation) | With heat integration (polymer H$_2$ separation membrane) |
|---|---|---|---|
| Total heating duty (×10$^6$ kJ/hr) | 198 | 0 | 0 |
| Total cooling duty (×10$^6$ kJ/hr) | 214 | 152 | 308 |
| Net duty (×10$^6$ kJ/hr) | −15.5 | −152 | −308 |
| Total heating cost flow ($/hr) | 489.76 | 0 | 0 |
| Total cooling cost flow ($/hr) | 61.62 | 82.70 | 72.57 |
| Total cost ($/hr) | 551.38 | 82.70 | 72.57 |

TABLE 5

Current costing and hourly production rates for feed and product species in the DNMC reaction.

| Methane Price ($/cu ft) | .00288 | Methane Cost ($/hr) | −2632 |
|---|---|---|---|
| Hydrogen Price ($/kg) | 1.39 | Hydrogen Cost ($/hr) | 3658 |
| Ethylene Price ($/kg) | 1.16 | Ethylene Cost ($/hr) | 1707 |

TABLE 5-continued

Current costing and hourly production rates for
feed and product species in the DNMC reaction.

| | | | |
|---|---|---|---|
| Benzene Price ($/kg) | 0.73 | Benzene Cost ($/hr) | 1326 |
| Naphthalene Price ($/kg) | 0.52 | Naphthalene Cost ($/hr) | 4205 |

TABLE 6

Annual plant operational utility and raw material costs
and sales credit for heat-integrated process Aspen model.

| | Operation Cost [USD/yr] | | | Sales Credit [USD/yr] |
|---|---|---|---|---|
| Utility/Material | Perovskite Membrane | Polymer Membrane | Product | Both Variations |
| Liquid propane | 480,459 | 68,710 | Hydrogen | 32,044,080 |
| Cooling water | 244,543 | 567,396 | Ethylene | 14,953,320 |
| Methane (feed) | 23,056,320 | 23,056,320 | Benzene | 11,615,760 |
| Electricity | 17,571,200 | 17,233,523 | Naphthalene | 36,835,800 |
| Catalyst | 438,000 | 438,000 | | |
| Total cost | 41,790,102 | 41,363,949 | Total Credit | 62,448,960 |

Figure 14B:
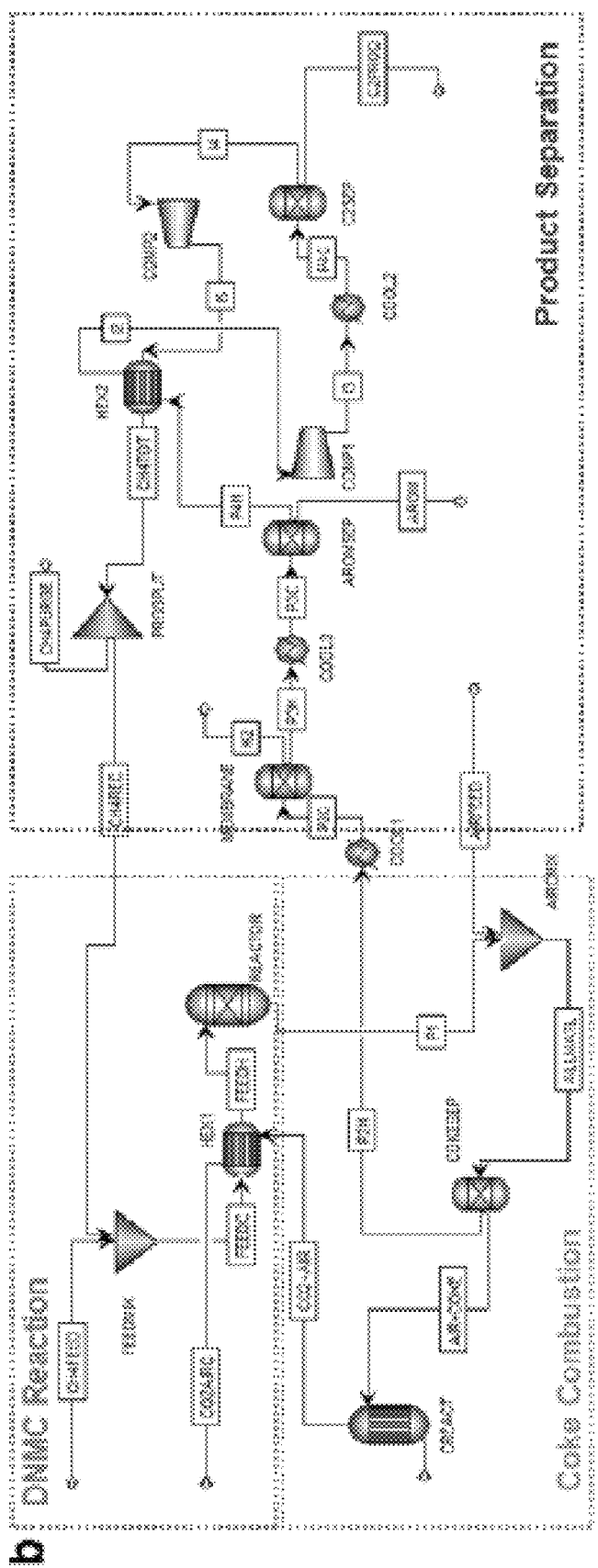
FIG. 14B shows an Aspen Plus (V10) simulation of a DNMC scale-up reaction using a perovskite-based hydrogen separation membrane with a feed at atmospheric pressure (1 atm) and hydrogen outlet pressure of 0.5 bar and 973 K, incorporating heat integration based on HEN design and pinch analysis.
Figure 14C:
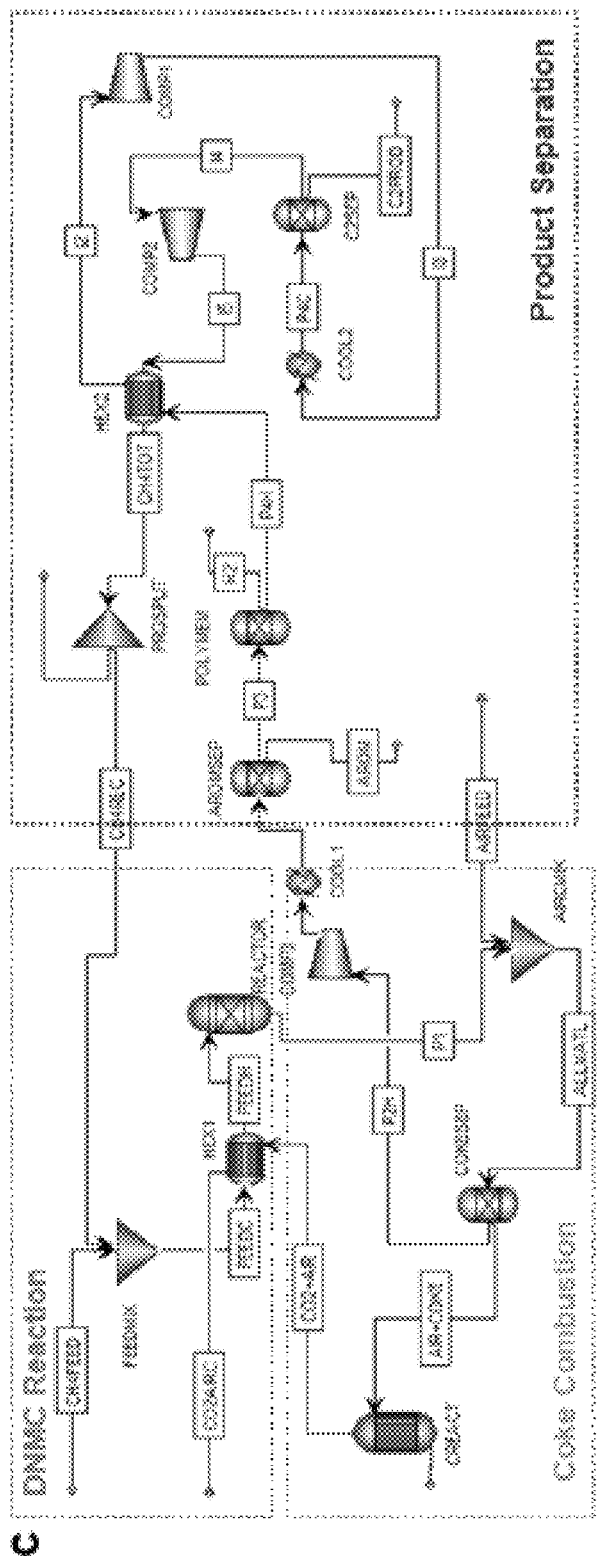
FIG. 14C shows an Aspen Plus (V10) simulation of a DNMC scale-up reaction using a polymer-based hydrogen separation membrane under 200 psig pressure and 355 K incorporating heat integration based on HEN design and pinch analysis.

In FIG. 14B, a heat exchanger network is incorporated to introduce heat integration into the system as an energy—and cost-saving technique and to model the autothermal nature of the reaction process. The feedstream needs to reach the reaction temperature of 1323 K, and the product stream following the combustion reaction provides adequate heat release from the exothermic reaction to maintain this feed stream temperature following the initial heating process. This energy-saving step eliminates the requirement for any external heating in the entire process. Furthermore, heating methane following the demethanizer with the heat released from the pre-treatment of the demethanizer feed stream is another optimization performed in the second simulation. As previously done for the simulation shown in FIG. 14A, the heating and cooling duties for the remaining heat exchangers and for the overall system were determined in the case of incorporating heat integration. The results from these calculations are tabulated in Table 3 and Table 4.

Comparing the results obtained from each simulation, the use of heat integration has a significant impact on the total cost of heating and cooling duties within the system. Due to the lack of further heating requirements in the system, we are able to sell all hydrogen gas produced in the process for a profit and avoid burning the hydrogen for an additional heat source. Finally, the potential profitability of this reaction is assessed, with some results in Table 5. Four products—ethylene, benzene, naphthalene and hydrogen—are valuable and can be sold for a substantial profit due to the low cost of obtaining natural gas. Additional electricity costs are also incorporated for powering some of the equipment operating under highly energy-intensive conditions. Table 6 provides an overall cost analysis of the annual plant operation expenses for utility and raw material use and the annual credit received from selling valuable reaction products. However, this analysis does not account for the costs of equipment, plant operators, separation of the desirable products, or storage. As such, the hourly cost of plant operation would be significantly higher than that determined by utility of heat exchanger costs alone.

The price of methane was obtained from the Bloomberg energy database online as was reported on Jul. 26, 2018[3]. Ethylene prices were determined using 2018 projections from ICIS pricing models based on historical data through 2012[4]. A linear correlation between crude oil and ethylene prices was observed and was used to determine the current price of ethylene based on the reported oil price of 69.65 USD/bbl in the morning on Monday, Jun. 23, 2018[3]. Benzene prices were determined using data from the ICIS analysis of CIF ARA prices in Europe in 2016[5]. Naphthalene prices were obtained using bulk costs for crude naphthalene on the Alibaba world trade website[7]. The market value for hydrogen was determined using a correlation between the cost of natural gas and hydrogen prices using historical data and projections assembled by the US Department of Energy in 2012. The hydrogen cost presented here correlates to the natural gas cost of 3 USD/MMBtu, which is representative of current market conditions[6].

TABLE 7

Equipment list for Aspen Plus simulation without heat integration.

| Name | Type | Description |
|---|---|---|
| COOL2 | cooler | step 1 in $C_1$ & $C_2$ product cooling (cooling water) |
| HEAT1 | heater | heats methane feed to 1050° C. (electricity) |
| REACTOR | yield reactor | DNMC reaction occurs |
| AIRCMIX | mixer | combines air with coke |
| COMP2 | turbine | reduces unreacted methane pressure |
| HEAT2 | heater | heats air/coke to reaction temperature (high-pressure steam) |
| COKESEP | separator | separates gas products from coke |
| B1 | demethanizer | used to thermally separate methane and $C_2$ |
| AROMSEP | separator | separates aromatics from $C_2$ and methane |
| COOL3 | cooler | uses cryogenic liquid to cool methane and $C_2$ (liquid propane) |
| COOL1 | cooler | reduces gas product temperature (cooling water) |
| MEMBRANE | membrane separator | semi-permeable membrane used to separate hydrogen |
| HEAT3 | heater | returns cryogenically cooled methane to room temperature (low-pressure steam) |
| CREACT | reactor | coke combustion reactor |
| COMP | compressor | increases methane and $C_2$ products before demethanizer |
| PRGSPLIT | splitter | splits unreacted methane into recycle and purge streams |
| FEEDMIX | mixer | mixes methane feed and recycle before reaction |

TABLE 8

Stream compositions for Aspen Plus simulation without heat integration.

| | | CH4FEED | FEED | 3 | P1 | P2H | P2C | H2 | P3 |
|---|---|---|---|---|---|---|---|---|---|
| Temperature | °C. | 25 | 24.99993 | 1050 | 1050 | 1133.178 | 100 | 100 | 100 |
| Pressure | bar | 1.01 | 1 | 1 | 1.01 | 1.01 | 1.01 | 1.01 | 1.01 |
| Molar Vapor Fraction | | 1 | 1 | 1 | 1 | 1 | 1 | 1 | 1 |
| Molar Liquid Fraction | | 0 | 0 | 0 | 0 | 0 | 0 | 0 | 0 |
| Mole Flow | kmol/hr | 1000 | 2434.722 | 2434.722 | 3251.223 | 3044.134 | 3044.134 | 1305.308 | 1738.826 |
| Mass Flow | kg/hr | 16042.76 | 39059.67 | 39059.67 | 39059.67 | 36572.27 | 36572.27 | 2631.344 | 33940.93 |
| Methane | kg/hr | 16042.76 | 39059.67 | 39059.67 | 25832.67 | 25832.67 | 25832.67 | 0 | 25832.67 |
| Hydrogen | kg/hr | 0 | 0 | 0 | 2631.337 | 2631.344 | 2631.344 | 2631.344 | 0 |
| Ethane | kg/hr | 0 | 0 | 0 | 95.5926 | 95.59226 | 95.59226 | 0 | 95.59226 |
| Ethylene | kg/hr | 0 | 0 | 0 | 1471.016 | 1471.014 | 1471.014 | 0 | 1471.014 |
| Acetylene | kg/hr | 0 | 0 | 0 | 408.5548 | 408.5541 | 408.5541 | 0 | 408.5541 |
| Benzene | kg/hr | 0 | 0 | 0 | 1816.885 | 1816.882 | 1816.882 | 0 | 1816.882 |
| Toluene | kg/hr | 0 | 0 | 0 | 114.1366 | 114.1397 | 114.1397 | 0 | 114.1397 |
| Naphthalene | kg/hr | 0 | 0 | 0 | 4202.088 | 4202.077 | 4202.077 | 0 | 4202.077 |
| Carbon | kg/hr | 0 | 0 | 0 | 2487.389 | 0 | 0 | 0 | 0 |
| Nitrogen | kg/hr | 0 | 0 | 0 | 0 | 0 | 0 | 0 | 0 |
| Carbon Dioxide | kg/hr | 0 | 0 | 0 | 0 | 0 | 0 | 0 | 0 |
| Oxygen | kg/hr | 0 | 0 | 0 | 0 | 0 | 0 | 0 | 0 |
| Water | kg/hr | 0 | 0 | 0 | 0 | 0 | 0 | 0 | 0 |

| | | AROM | P4H | I1 | I2 | P4C | C2PROD | CH4H | I3 |
|---|---|---|---|---|---|---|---|---|---|
| Temperature | °C. | 100 | 100 | 451.3995 | 14 | −91 | −91 | −91 | −161.644 |
| Pressure | bar | 1.01 | 1.01 | 21 | 21 | 21 | 21 | 21 | 1 |
| Molar Vapor Fraction | | 0 | 1 | 1 | 1 | 0.968928 | 0 | 1 | 0.992597 |
| Molar Liquid Fraction | | 1 | 0 | 0 | 0 | 0.031072 | 1 | 0 | 0.007403 |
| Mole Flow | kmol/hr | 57.28251 | 1681.544 | 1681.544 | 1681.544 | 1681.544 | 87.40771 | 1594.136 | 1594.136 |
| Mass Flow | kg/hr | | | | | | | | |
| Methane | kg/hr | 6133.099 | 27807.83 | 27807.83 | 27807.83 | 27807.83 | 2233.487 | 25574.34 | 25574.34 |
| Hydrogen | kg/hr | 0 | 25832.67 | 25832.67 | 25832.67 | 25832.67 | 258.3267 | 25574.34 | 25574.34 |
| Ethane | kg/hr | 0 | 0 | 0 | 0 | 0 | 0 | 0 | 0 |
| Ethylene | kg/hr | 0 | 95.59226 | 95.59226 | 95.59226 | 95.59226 | 95.59226 | 0 | 0 |
| Acetylene | kg/hr | 0 | 1471.014 | 1471.014 | 1471.014 | 1471.014 | 1471.014 | 0 | 0 |
| Benzene | kg/hr | 0 | 408.5541 | 408.5541 | 408.5541 | 408.5541 | 408.5541 | 0 | 0 |
| Toluene | kg/hr | 1816.882 | 0 | 0 | 0 | 0 | 0 | 0 | 0 |
| Naphthalene | kg/hr | 114.1397 | 0 | 0 | 0 | 0 | 0 | 0 | 0 |
| Carbon | kg/hr | 4202.077 | 0 | 0 | 0 | 0 | 0 | 0 | 0 |
| Nitrogen | kg/hr | 0 | 0 | 0 | 0 | 0 | 0 | 0 | 0 |
| Carbon Dioxide | kg/hr | 0 | 0 | 0 | 0 | 0 | 0 | 0 | 0 |
| Oxygen | kg/hr | 0 | 0 | 0 | 0 | 0 | 0 | 0 | 0 |
| Water | kg/hr | 0 | 0 | 0 | 0 | 0 | 0 | 0 | 0 |

| | | CH4C | CH4PURGE | CH4REC | COKE | AIRFEED | S1 | AIR + COKE | CO2 + AIR |
|---|---|---|---|---|---|---|---|---|---|
| Temperature | °C. | 25 | 25 | 25 | 1133.178 | 25 | 166.7769 | 1050 | 1050 |
| Pressure | bar | 1 | 1 | 1 | 1.01 | 1.01 | 1.01 | 1.01 | 1.01 |
| Molar vapor fraction | | 1 | 1 | 1 | 1 | 0 | 1 | 0.828357 | 1 |
| Molar Liquid Fraction | | 0 | 0 | 0 | 0 | 1 | 0 | 0.171643 | 0 |
| Mole Flow | kmol/hr | 1594.136 | 159.4136 | 1434.722 | 207.0926 | 1000 | 1207.093 | 1207.248 | 999.9997 |
| Mass Flow | kg/hr | 25574.34 | 2557.434 | 23016.91 | 2487.389 | 28850.4 | 31337.79 | 31337.79 | 31312.9 |
| Methane | kg/hr | 25574.34 | 2557.434 | 23016.91 | 0 | 0 | 0 | 0 | 0 |
| Hydrogen | kg/hr | 0 | 0 | 0 | 0 | 0 | 0 | 0 | 0 |
| Ethane | kg/hr | 0 | 0 | 0 | 0 | 0 | 0 | 0 | 0 |
| Ethylene | kg/hr | 0 | 0 | 0 | 0 | 0 | 0 | 0 | 0 |
| Acetylene | kg/hr | 0 | 0 | 0 | 0 | 0 | 0 | 0 | 0 |
| Benzene | kg/hr | 0 | 0 | 0 | 0 | 0 | 0 | 0 | 0 |
| Toluene | kg/hr | 0 | 0 | 0 | 0 | 0 | 0 | 0 | 0 |
| Naphthalene | kg/hr | 0 | 0 | 0 | 0 | 0 | 0 | 0 | 0 |
| Carbon | kg/hr | 0 | 0 | 0 | 2487.389 | 0 | 2487.389 | 2487.389 | 2.47E−06 |
| Nitrogen | kg/hr | 0 | 0 | 0 | 0 | 22130.65 | 22130.65 | 22130.65 | 22130.64 |
| Carbon | kg/hr | 0 | 0 | 0 | 0 | 0 | 0 | 0 | 9022.961 |
| Oxygen | kg/hr | 0 | 0 | 0 | 0 | 6719.748 | 6719.748 | 6719.748 | 159.3008 |
| Water | kg/hr | 0 | 0 | 0 | 0 | 0 | 0 | 0 | 0 |

TABLE 9

Equipment list for Aspen Plus simulations using heat integration.

| Name | Type | Description |
|---|---|---|
| HEX1 | heat exchanger | heat exchange between methane feed (cold) & combustion product stream (hot) - represents autothermal process |
| HEX2 | heat exchanger | heat exchange between unreacted methane (cold) & $C_1 + C_2$ products (hot) |
| REACTOR | yield reactor | DNMC reaction occurs |
| AIRCMIX | mixer | combines air with coke |
| COMP3[a] | compressor | increases product pressure for hydrogen separation |
| COMP2 | turbine | reduces unreacted methane pressure |
| COKESEP | separator | separates gas products from coke + air (theoretical step) |
| C2SEP | demethanizer | used to thermally separate methane and $C_2$ |
| AROMSEP | separator | separates aromatics from C2 and methane |
| COOL2 | cooler | uses cryogenic liquid to cool methane and C 2 (liquid propane) |
| COOL1 | cooler | reduces gas product temperature (cooling water) |
| COOL3b | cooler | reduces gas product temperature (cooling water) |
| MEMBRANE/POLY SEP | membrane separator | semi-permeable membrane used to separate hydrogen |
| CREACT | reactor | coke combustion reactor |
| COMP | compressor | increases methane and C2 product pressures |
| PRGSPLIT | splitter | splits unreacted methane into recycle and purge streams |
| FEEDMIX | mixer | mixes methane feed and recycle before reaction |

TABLE 10

Stream compositions for Aspen Plus simulation with heat integration using perovskite membrane for H2 separation (feed 1.01 bar, H$_2$ product 0.5 bar, temperature 700° C.).

| | | CH4FEED | FEEDC | FEEDH | AIRFEED | ALLMATL | AIR + COKE | CO2 + AIR | CO2AIRC |
|---|---|---|---|---|---|---|---|---|---|
| Temperature | ° C. | 25 | 24.9999 | 1050 | 1050 | 1050 | 1050 | 4747.86 | 988.793 |
| Pressure | bar | 1.01325 | 1.01 | 1.01 | 1.01325 | 1.01 | 1.01 | 1.01 | 1.01 |
| Molar Vapor Fraction | | 1 | 1 | 1 | 1 | .951 | .829 | 1 | 1 |
| Molar Liquid Fraction | | 0 | 0 | 0 | 0 | 0 | 0 | 0 | 0 |
| Molar Solid Fraction | | 0 | 0 | 0 | 0 | 0.0488 | 0.172 | 0 | 0 |
| Mole Flow | kmol/hr | 1000 | 2432.207 | 2438.166 | 1000 | 4245.52 | 1206.73 | 1000 | 1000 |
| Mass Flow | kg/hr | 16042.76 | 39019.32 | 39019.32 | 28850.4 | 67910.07 | 31333.4 | 31106.9 | 31106.9 |
| Methane | kg/hr | 16042.76 | 39019.32 | 39019.32 | 0 | 25787.4 | 0 | 0 | 0 |
| Hydrogen | kg/hr | 0 | 0 | 0 | 0 | 2626.72 | 0 | 0 | 0 |
| Ethane | kg/hr | 0 | 0 | 0 | 0 | 95.425 | 0 | 0 | 0 |
| Ethylene | kg/hr | 0 | 0 | 0 | 0 | 1468.44 | 0 | 0 | 0 |
| Acetylene | kg/hr | 0 | 0 | 0 | 0 | 407.839 | 0 | 0 | 0 |
| Benzene | kg/hr | 0 | 0 | 0 | 0 | 1813.7 | 0 | 0 | 0 |
| Toluene | kg/hr | 0 | 0 | 0 | 0 | 113.937 | 0 | 0 | 0 |
| Naphthalene | kg/hr | 0 | 0 | 0 | 0 | 4194.72 | 0 | 0 | 0 |
| Carbon | kg/hr | 0 | 0 | 0 | 0 | 2483.03 | 2483.03 | 0 | 0 |
| Nitrogen | kg/hr | 0 | 0 | 0 | 22130.6 | 22130.6 | 22130.6 | 22130.6 | 22130.6 |
| Carbon Dioxide | kg/hr | 0 | 0 | 0 | 0 | 0 | 0.0 | 8268.08 | 8268.08 |
| Oxygen | kg/hr | 0 | 0 | 0 | 6719.75 | 6719.75 | 6719.75 | 708.161 | 708.161 |
| Water | kg/hr | 0 | 0 | 0 | 0 | 0 | 0 | 0 | 0 |

| | | P2H | P2C | H2 | P3 | AROM | P4H | I2 | I3 |
|---|---|---|---|---|---|---|---|---|---|
| Temperature | ° C. | 1050 | 100 | 100 | 100 | 100 | 100 | −68.0288 | 204.709 |
| Pressure | bar | 1.01 | 1.01 | 0.5 | 1.01 | 1.01 | 1.01 | 1.01 | 21 |
| Molar Vapor Fraction | | 1 | 1 | 1 | 1 | 1 | 0 | 1 | 1 |
| Molar Liquid Fraction | | 0 | 0 | 0 | 0 | 0 | 1 | 0 | 0 |
| Molar Solid Fraction | | 0 | 0 | 0 | 0 | 0 | 0 | 0 | 0 |
| Mole Flow | kmol/hr | 3038.79 | 3038.79 | 1303.02 | 1735.78 | 57.1822 | 1678.6 | 1678.6 | 1678.6 |
| Mass Flow | kg/hr | 36508.2 | 36508.2 | 2626.72 | 33881.4 | 6122.36 | 27759.1 | 27759.1 | 27759.1 |
| Methane | kg/hr | 25787.4 | 25787.4 | 0.0 | 25787.4 | 0 | 25787.4 | 25787.4 | 25787.4 |
| Hydrogen | kg/hr | 2626.72 | 2626.72 | 2626.72 | 0.0 | 0 | 0 | 0 | 0 |
| Ethane | kg/hr | 95.425 | 95.425 | 0 | 95.425 | 0 | 95.425 | 95.425 | 95.425 |
| Ethylene | kg/hr | 1468.44 | 1468.44 | 0 | 1468.44 | 0 | 1468.44 | 1468.44 | 1468.44 |
| Acetylene | kg/hr | 407.839 | 407.839 | 0 | 407.839 | 0 | 407.839 | 407.839 | 407.839 |
| Benzene | kg/hr | 1813.7 | 1813.7 | 0 | 1813.7 | 1813.7 | 0 | 0 | 0 |
| Toluene | kg/hr | 113.937 | 113.937 | 0 | 113.937 | 113.937 | 0 | 0 | 0 |
| Naphthalene | kg/hr | 4194.72 | 4194.72 | 0 | 4194.72 | 4194.72 | 0 | 0 | 0 |
| Carbon | kg/hr | 0 | 0 | 0 | 0 | 0 | 0 | 0 | 0 |
| Nitrogen | kg/hr | 0 | 0 | 0 | 0 | 0 | 0 | 0 | 0 |
| Carbon Dioxide | kg/hr | 0 | 0 | 0 | 0 | 0 | 0 | 0 | 0 |
| Oxygen | kg/hr | 0 | 0 | 0 | 0 | 0 | 0 | 0 | 0 |
| Water | kg/hr | 0 | 0 | 0 | 0 | 0 | 0 | 0 | 0 |

TABLE 10-continued

Stream compositions for Aspen Plus simulation with heat integration using perovskite membrane for H2 separation (feed 1.01 bar, H$_2$ product 0.5 bar, temperature 700° C.).

| | | P4C | C2PROD | I4 | I5 | CH4TOT | CH4REC | CH4PURGE |
|---|---|---|---|---|---|---|---|---|
| Temperature | ° C. | −91 | −91 | −91 | −161.644 | 25 | 25 | 25 |
| Pressure | bar | 21 | 21 | 21 | 1.01 | 1.01 | 1.01 | 1.01 |
| Molar Vapor Fraction | | 0.9689 | 0 | 0 | 1 | 0.9926 | 1 | 1 |
| Molar Liquid Fraction | | 0.03107 | 1 | 1 | 0 | 0.007407 | 0 | 0 |
| Molar Solid Fraction | | 2.23E−17 | 0 | 0 | 4.41E−17 | 0 | 0 | 0 |
| Mole Flow | kmol/hr | 1678.6 | 87.255 | 1591.34 | 1591.34 | 1591.34 | 1432.21 | 159.134 |
| Mass Flow | kg/hr | 27759.1 | 2229.57 | 25529.5 | 25529.5 | 25529.5 | 22976.6 | 2552.95 |
| Methane | kg/hr | 25787.4 | 257.874 | 25529.5 | 25529.5 | 25529.5 | 22976.6 | 2552.95 |
| Hydrogen | kg/hr | 0 | 0 | 0 | 0 | 0 | 0 | 0 |
| Ethane | kg/hr | 95.425 | 95.425 | 0 | 0 | 0 | 0 | 0 |
| Ethylene | kg/hr | 1468.44 | 1468.44 | 0 | 0 | 0 | 0 | 0 |
| Acetylene | kg/hr | 407.839 | 407.839 | 0 | 0 | 0 | 0 | 0 |
| Benzene | kg/hr | 0 | 0 | 0 | 0 | 0 | 0 | 0 |
| Toluene | kg/hr | 0 | 0 | 0 | 0 | 0 | 0 | 0 |
| Naphthalene | kg/hr | 0 | 0 | 0 | 0 | 0 | 0 | 0 |
| Carbon | kg/hr | 0 | 0 | 0 | 0 | 0 | 0 | 0 |
| Nitrogen | kg/hr | 0 | 0 | 0 | 0 | 0 | 0 | 0 |
| Carbon Dioxide | kg/hr | 0 | 0 | 0 | 0 | 0 | 0 | 0 |
| Oxygen | kg/hr | 0 | 0 | 0 | 0 | 0 | 0 | 0 |
| Water | kg/hr | 0 | 0 | 0 | 0 | 0 | 0 | 0 |

References for Example 1

1. a) M. Peplow, Nature 2017, 550, 26-28; b) J. A. Rapporteur, National Academies Press 2016, 1-102.
2. a) C. Mesters, Annu. Rev. Chem. Biomol. Eng. 2016, 7, 223-238; b) W. Taifan, J. Baltrusaitis, Appl. Catal. 8. 2016, 198, 525-547.
3. a) C. Karakaya, R. J. Kee, Prog. Energy Combus. Sci. 2016, 55, 60-97; b) P. Schwach, X. Pan, X. Bao, Chem. Rev. 2017, 117, 8497-8520; c) P. Tang, Q. Zhu, Z. Wu, D. Ma, Energy Environ. Sci. 2014, 7, 2580-2591; d) J. J. Spivey, G. Hutchings, Chem. Soc. Rev. 2014, 43, 792-803.
4. a) A. M. Dean, J. Phys. Chem. 1990, 94, 1432-1439; b) C. Keramiotis, G. Vourliotakis, G. Skevis, M. A. Founti, C. Esarte, N. E. Sanchez, A. Millera, R. Bilbao, M. U. Alzueta, Energy 2012, 43, 103-110; c) J. Erlebacher, J. B. Gaskey, U.S. Pat. No. 9,776,860B2, 2017.
5. a) N. Kosinov, F. J. A. G. Coumans, E. Uslamin, F. Kapteijn, E. J. M. Hensen, Angew. Chem. Int. Ed. 2016, 55, 15086-15090; b) X. G. Guo, G. Z. Fang, G. Li, H. Ma, H. J. Fan, L. Yu, C. Ma, X. Wu, D. H. Deng, M. M. Wei, D. L. Tan, R. Si, S. Zhang, J. Q. Li, L. T. Sun, Z. C. Tang, X. L. Pan, X. H. Bao, Science 2014, 344, 616-619; c) A. I. Olivos-Suarez, À. Szécsény i, E. J. M. Hensen, J. Ruiz-Martinez, E. A. Pidko, J. Gascon, ACS Catal. 2016, 6, 2965-2981; d) D. C. Upham, V. Agarwal, A. Khechfe, Z. R. Snodgrass, M. J. Gordon, H. Metiu, E. W. McFarland, Science 2017, 358, 917-921. e) Seung Ju Han, Sung Woo Lee, Hyun Woo Kim, Seok Ki Kim, Yong Tae Kim. Nonoxidative Direct Conversion of Methane on Silica-Based Iron Catalysts: Effect of Catalytic Surface. ACS Catalysis 2019, 9 (9), 7984-7997.
6. a) C. Guéret, M. Daroux, F. Billaud, Chem. Eng. Sci. 1997, 52, 815-827; b) A. Holmen, O. Olsvik, O. Rokstad, Fuel Process. Technol. 1995, 42, 249-267; c) D. M. Matheu, A. M. Dean, J. M. Grenda, W. H. Green, J. Phys. Chem. A 2003, 107, 8552-8565.
7. a) W. Ding, S. Li, G. D Meitzner, E. Iglesia, J. Phys. Chem. 8. 2001, 105, 506-513; b) N. Kosinov, F. J. A. G. Coumans, E. A. Uslamin, A. S. G. Wijpkema, B. Mezari, E. J. M. Hensen, ACS Catal. 2017, 7, 520-529; c) M. C. Alvarez-Galvan, N. Mota, M. Ojeda, S. Rojas, R. M. Navarro, J. L. G. Fierro, Catal. Today 2011, 171, 15-23; d) Z. Cao, H. Jiang, H. Luo, S. Baumann, W. A. Meulenberg, J. Assmann, L. Mleczko, Y. Liu, J. Caro, Angew. Chem. Int. Ed. 2013, 52, 13794-13797; e) S. H. Morejudo, R. Zanón, S. Escolástico, I. Yuste-Tirados, H. Malerød-Fjeld, P. K. Vestre, W. G. Coors, A. Martínez, T. Norby, J. M. Serra, C. Kjølseth, Science 2016, 353, 563-566.
8. a) K. Venkataraman, J. Redenius, L. Schmidt, Chem. Eng. Sci. 2002, 57, 2335-2343.
9. a) E. Wanat, K. Venkataraman, L. Schmidt, Appl. Catal. A 2004, 276, 155-162; b) K. Venkataraman, E. Wanat, L. Schmidt, AIChE J. 2003, 49, 1277-1284; c) A. L. Y. Tonkovich, B. Yang, S. T. Perry, S. P. Fitzgerald, Y. Wang, Catal. Today 2007, 120, 21-29.
10. a) M. Zanfir, A. Gavriilidis, Chem. Eng. Sci. 2003, 58, 3947-3960; b) J. Redenius, L. Schmidt, O. Deutschmann, AIChE J. 2001, 47, 1177-1184; c) G. Kolios, J. Frauhammer, G. Eigenberger, Chem. Eng. Sci. 2002, 57, 1505-1510.
11. a) K. Huang, J. B. Miller, G. W. Huber, J. A. Dumesic, C. T. Maravelias, Joule 2018, 2, 349-365.
12. M. Sakbodin, Y. Wu, S. C. Oh, E. D. Wachsman, D. Liu, Angew. Chem. Int. Ed. 2016, 55, 16149-16152.

References for Results Section

1. M. T. DeAngelis, A. J. Rondinone, M. D. Pawel, T. C. Labotka, L. M. Anovitz, American Mineralogist 2012, 97, 653-656.
2. K. Venkataraman, J. Redenius, L. Schmidt, Chemical engineering science 2002, 57, 2335-2343.
3. Bloomberg, in Market: Energy, 2018.
4. P. Hodges, in Chemicals & the Economy, Vol. 2018 (Ed.: ICIS), 2014.
5. T. Mellor, in ICIS Chemical Business, 2016.
6. T. R. Sara Dillich, Marc Melaina, (Ed.: D. o. Energy), 2012.
7. Crude Naphthalene https://www.alibaba.com/showroom/crude-naphthalene.html (accessed August 23).

Example 2

Improving Hydrocarbon Yield and Autothermality with Oxidative Co-Feed in Direct Non-Oxidative Methane Conversion on Iron/Quartz Catalyst Direct non-oxidative methane conversion (DNMC) into larger hydrocarbons over an iron/silica (Fe/SiO$_2$) catalyst is a promising solution for developing liquid fuels and chemicals from methane feedstock. This reaction has typically been studied using pure methane on cristobalite-supported Fe-species that was made via the quartz-cristobalite transformation at 1973 K. The endothermicity nature of DNMC requires high temperatures to obtain attractive methane conversion, but high temperatures require high energy input to initiate and maintain the DNMC reaction. Here, we report an oxidative co-feed addition method to concurrently supply energy for DNMC and improve methane conversion as well as hydrocarbon product yield over a quartz-supported Fe-species (Fe/SiO$_2$(Q), "Q" denotes for quartz) catalyst. The catalyst was prepared via a flame-fusion method that maintains quartz crystalline phase of the support. Oxidative co-feeds including oxygen (O$_2$), carbon dioxide (CO$_2$) and carbon monoxide (CO) were introduced in DNMC. The O$_2$ co-feed demonstrates the positive impact on methane conversion, lighter hydrocarbon selectivity and hydrocarbon yield; while CO$_2$ and CO are unable to provide advantages regarding either methane conversion or hydrocarbon product selectivity. In a non-limiting embodiment, an energy balance between energy required by DNMC and energy released from oxidation reactions was reached at around 15 vol % O$_2$ co-feed to maintain autothermality of the DNMC reaction.

Introduction

Methane (CH$_4$) is the primary component in natural gas whose abundance in the world has gained intensive attention as a potential source, alternative to petroleum, for hydrocarbon fuel and chemical production. Methane is also the second most abundant anthropogenic greenhouse gas after carbon dioxide (CO$_2$) in the earth's atmosphere, roughly 30 times more potent as a heat-trapping gas than CO$_2$. Therefore, methane conversion into liquid fuels has been a focus of current research efforts, which aims to reduce the world's reliance on dwindling fossil fuel reserves, while also to decrease the concentration of this potent greenhouse gas in the earth's atmosphere.

The leading technology used in industry to achieve conversion of methane to liquids consists of oxidative reforming of methane to syngas (CO and H$_2$) followed by Fischer-Tropsch synthesis of higher hydrocarbons.[1] This process involves multiple steps, is energy-intensive and emits CO$_2$ greenhouse gas. This leads to high capital cost, low overall energy efficiency, and low carbon efficiency. The direct conversion of methane to ethylene (C$_2$H$_4$) through the oxidative coupling of methane is being studied at the lab-scale, but suffers from a low C$_2$H$_4$ yield and substantial waste as a large fraction of CH$_4$ is fully or partially oxidized to CO$_2$ and carbon monoxide (CO). The direct non-oxidative methane conversion (DNMC) reaction is promising since it converts CH$_4$ in one-step to olefins and aromatics (such as ethylene and benzene) and hydrogen (H$_2$) co-product. The DNMC pathway is significantly simple, requires a lower investment, and all the products are highly valuable for the fuel, chemical, and polymer industries. However, this reaction, using molybdenum loaded zeolite such as Mo/ZSM-5 as a catalyst in the past, suffers from low methane conversion and rapid catalyst deactivation, due to the high endothermicity of the reaction and coke deposition on the catalyst, and the low hydrocarbon product yield[2-3].

Investigation into improved catalyst for DNMC has resulted in the development of a silica material containing embedded single iron sites (Fe/SiO$_2$). This catalyst demonstrated superior DNMC performance, with very high methane conversions and high selectivity for ethylene and aromatics. A mixed heterogeneous-homogeneous reaction network was hypothesized for the DNMC on Fe/SiO$_2$ catalyst, in which the silica lattice confined Fe species initiate CH$_4$ dehydrogenation to generate methyl (·CH$_3$) and hydrogen (·H) radicals and the radicals enable a series of gas-phase reactions to form dehydrogenated and cyclized larger hydrocarbon products. The Fe/SiO$_2$ catalyst prepared from fayalite and quartz by a melt-fusing at 1973 K showed a higher resistance to structural sintering and coke deposition than other Fe-containing catalyst analogues. The involvement of ·H radicals in the reaction network was verified by the thermal decomposition of hydrogen-donor molecules, such as 1,2,3,4-tetrahydronaphthalene and benzene, in the DNMC which improved methane conversion to olefins and aromatics. It should be noted that the catalyst support in the Fe/SiO$_2$ catalyst in previous studies was cristobalite due to the silica phase transformation from quartz-to-cristobalite upon melting at 1973 K in a heating furnace. The reaction, however, is still challenged by a high reaction temperature (i.e., exceeding 1200 K) and high heat supply for CH$_4$ activation due to the highly endothermic nature of the DNMC.

The past research in our group aims to achieve the technoeconomic feasibility of DNMC by concurrently surpassing the challenges of low methane conversion, low larger hydrocarbon product selectivity, low catalyst durability, and high energy input via advanced reactor designs and reaction operations. The hydrogen (H$_2$) permeable mixed ionic-electronic membrane reactor that holds the promise of circumventing limitations of thermodynamic equilibrium by removal of H$_2$ by-product in-situ and resulting in increased product yields and H$_2$ product separation was designed for DNMC over the Fe/SiO$_2$ catalyst. The methane conversion, product selectivity towards C$_2$ or aromatics were manipulated purposely by adding or removing H$_2$ from the membrane reactor feed and permeate gas streams. A simple energy balance calculation shows that the membrane reactor can self-sustain its heat requirement (i.e. autothermality) by combusting ~36% of the H$_2$ permeate. The usage of other type of sweep gases such as CO$_2$ in the H$_2$ permeate side can lead to the reverse water gas shift reaction. The single hydrogen-permeable membrane reactor integrated dual reactions in one device, realizing the potentials to produce value-added hydrocarbons from CH$_4$ and CO$_2$ greenhouse gases. In addition, we created the catalytic wall reactor comprised of the Fe/SiO$_2$(Q) catalyst coating layer on a quartz reactor wall for the DNMC reaction. The catalytic wall reactor enabled stable methane conversion, C$_{2+}$ selectivity, coke yield, and long-term durability. These effects originate from initiation of the DNMC on a reactor wall and maintenance of the reaction by gas-phase chemistry within the reactor compartment. The energy balance analysis based on standard heat of reaction from both DNMC and coke combustion indicated the techno feasibility of the autothermal operation of the catalytic wall reactor for DNMC reaction.

In this Example, we report another strategy to initiate DNMC on Fe/SiO$_2$(Q) catalyst with high methane conversion, larger hydrocarbon selectivity, low coke formation and concurrently realizing reaction autothermality of this highly endothermic reaction. The Fe-species in the Fe/SiO$_2$(Q) catalyst maintains similar coordination structure to that of activated in the DNMC. Therefore, catalyst deactivation is not required in the beginning of DNMC, different from the Fe/SiO$_2$ catalyst. This was achieved by adding oxidative co-feed in DNMC on a quartz-supported Fe-species (Fe/SiO$_2$(Q)) catalyst. The flame-fusing method was employed to prepare the Fe/SiO$_2$(Q) catalyst which maintained the quartz crystalline phase of catalyst support. Oxidative co-feeds including oxygen (O$_2$), carbon dioxide (CO$_2$) and carbon monoxide (CO) were introduced in DNMC. The O$_2$ co-feed demonstrates the positive impact on methane conversion, lighter hydrocarbon selectivity and hydrocarbon yield; while CO$_2$ and CO are unable to provide advantages regarding either methane conversion or hydrocarbon product selectivity. An energy balance between energy required by DNMC and energy released from oxidation reactions might be reached at ~15 vol % $O_2$ co-feed to maintain autothermality of the DNMC reaction. The present Example also provides a guidance towards DNMC reaction using natural gas feedstock that often contain oxidative compounds since the use of natural gas over purified methane is energetically and economically desirable.

Experimental

Synthesis of Fe/SiO$_2$(Q) Catalyst

Prior to synthesizing the Fe/SiO$_2$(Q) catalyst, fayalite (Fe$_2$SiO$_4$) was prepared using the method reported by DeAngelis et al[4] to serve as the Fe source. Details on the preparation of Fe$_2$SiO$_4$ were also reported in our previous work. The as-prepared Fe$_2$SiO$_4$ and quartz (SiO$_2$) particles were mixed together and ball milled for 12 hours. The mixture was then loaded into the center of a quartz tube (6.35 mm in outer diameter and 5.00 mm in inner diameter) and heated in a hydrogen/oxygen (H$_2$/O$_2$) flame using a torch (3A blow pipe). The tube softened and the packed particles stuck to each other. Once the quartz tube was cooled, the tube was broken down and the packed particles were collected as the Fe/SiO$_2$(Q) catalyst.

DNMC Reaction on Fe/SiO$_2$(Q) Catalysts

The DNMC reaction was carried out using a tubular U-shaped packed-bed quartz reactor (10 mm inner diameter). Experiments were performed at 101 kPa gas pressure, and temperature was held constant using a Watlow Controller (96 series) to control the resistively-heated furnace (National Electric Furnace type FA120). The catalyst temperature was measured using a K-type thermocouple whose tip was placed at the bottom of the catalyst bed on the external surface of the quartz reactor. Fe/SiO$_2$(Q) catalyst (0.375 g) was heated from room temperature to 1273 K under flowing helium (50 mL min$^{-1}$, UHP grade, Airgas) controlled by a Brooks (SLA1580S, 200 sccm) mass flow controller at a ramping rate of 10 K min$^{-1}$. After reaching the reaction temperature, argon (internal standard) at 4 mL min$^{-1}$, methane at 16 mL min$^{-1}$, both managed using an AALBORG (GFC17, 200 sccm) mass flow controller, and the highest concentration of co-feed (O$_2$, CO$_2$, or CO) at 2 mL min$^{-1}$ (10 v/v %) using an MKS MFC was introduced into the catalyst bed. After 6 hours of reaction, the co-feed concentration was reduced to 1.4 mL min$^{-1}$ (7 v/v %) and held for 6 hours. This process was repeated for each co-feed concentration, 1 mL min$^{-1}$ (5 v/v %) and 0.4 mL min$^{-1}$ (2 v/v %) and concluded with a 0 v/v % co-feed control experiment. Effluents from the reactor were analyzed using a gas chromatograph (Agilent 7890A) containing a methyl-siloxane capillary column (HP-1, 50.0 m×320 μm×0.52 μm) connected to a flame-ionization detector (FID) and a packed column (ShinCarbon ST Columns, 80/100 mesh, 6 feet) linked to a thermal conductivity detector (TCD).

Catalyst Characterization

Powder X-ray diffraction (XRD) using a Bruker D8 Advance Lynx Powder Diffractometer (LynxEye PSD detector, sealed tube, Cu Kα radiation with Ni β-filter) was used to measure the crystalline phase of the fresh and spent Fe/SiO$_2$(Q) catalysts. The nitrogen (N$_2$) adsorption-desorption isotherm was measured using an Autosorb-iQ analyzer (Quantachrome Instruments) at 77 K. The specific surface area of the catalyst was determined using the Brunauer, Emmett and Teller (BET) method. The Fe composition of the catalyst was determined by inductively coupled plasma optical emission spectroscopy (ICP-EOS, Optima 4300DV Instrument, Perkin-Elmer). Raman spectroscopy was conducted on the spent catalysts using a LabRAM HR Evolution instrument ARAMIS, CCD detector) under ambient conditions with a 633 nm HeNe laser source for excitation. X-ray photoelectron spectroscopy was performed to measure the bonding environment of elements in the catalysts. X-ray absorption spectroscopy (XAS) measurement was conducted to determine the coordination structure of Fe species in the catalyst under ambient conditions. Fe K edge XAS measurement of the Fe/SiO$_2$(Q) sample was conducted at beamline 5-BMD at the Advanced Photon Source in Argonne National Laboratory. The XAS data were recorded under fluorescence mode. Fe foil, FeO, Fe$_2$O$_3$ and Fe$_3$O$_4$ were used as references and measured using the same beam lines. The X-ray absorption near edge structure (XANES) of the XAS data were analyzed using Athena software.

High-resolution transmission electron micrographs were acquired using transmission electron microscope (TEM) operated at 200 keV. The high-angle annular-dark-field (HAADF) image was acquired with the illumination semi-angle of 25 mrad and probe current of 100 pA. The dwell time for image acquisition was set at 10 microseconds per pixel to ensure an appropriate signal to noise ratio was achieved.

Analyses of Coke on Spent Fe/SiO$_2$(Q) Catalysts

The coke quantity and formation rate on the spent catalysts at different reaction conditions was measured using a Thermogravimetric analysis (TGA, Shimadzu, TGA-50) instrument. In the measurement, 0.01 g of spent catalyst was exposed to 50 mL min$^{-1}$ flowing air and ramped from room temperature to 1273 K at 10 K min$^{-1}$. The weight loss resulting from combustion of coke on the catalyst was recorded. The coke formation rate was calculated by division of coke weight by the total reaction time.

The coke nature on the spent catalyst was examined using temperature-programmed oxidation (TPO) experiment. The coked catalyst was placed inside a quartz tube and held in place with quartz wool, which was then set in a temperature-controlled furnace with temperature held constant using a Eurotherm Controller (2408 series). The catalyst temperature was monitored by a K-type thermocouple attached to the outer wall of the quartz sample holder. The furnace was ramped to 1123 K at a ramp rate of 10 K min$^{-1}$ under a flowing He (35 mL min$^{-1}$, ultrapure, Airgas) and O$_2$ (5 mL min$^{-1}$, ultrapure, Airgas) atmosphere. The O$_2$-TPD profile was recorded using a mass spectrometer (ABB Extrel) during this step.

Results and Discussion

Structural Properties of the Fe/SiO$_2$(Q) Catalyst

Figure 15A:
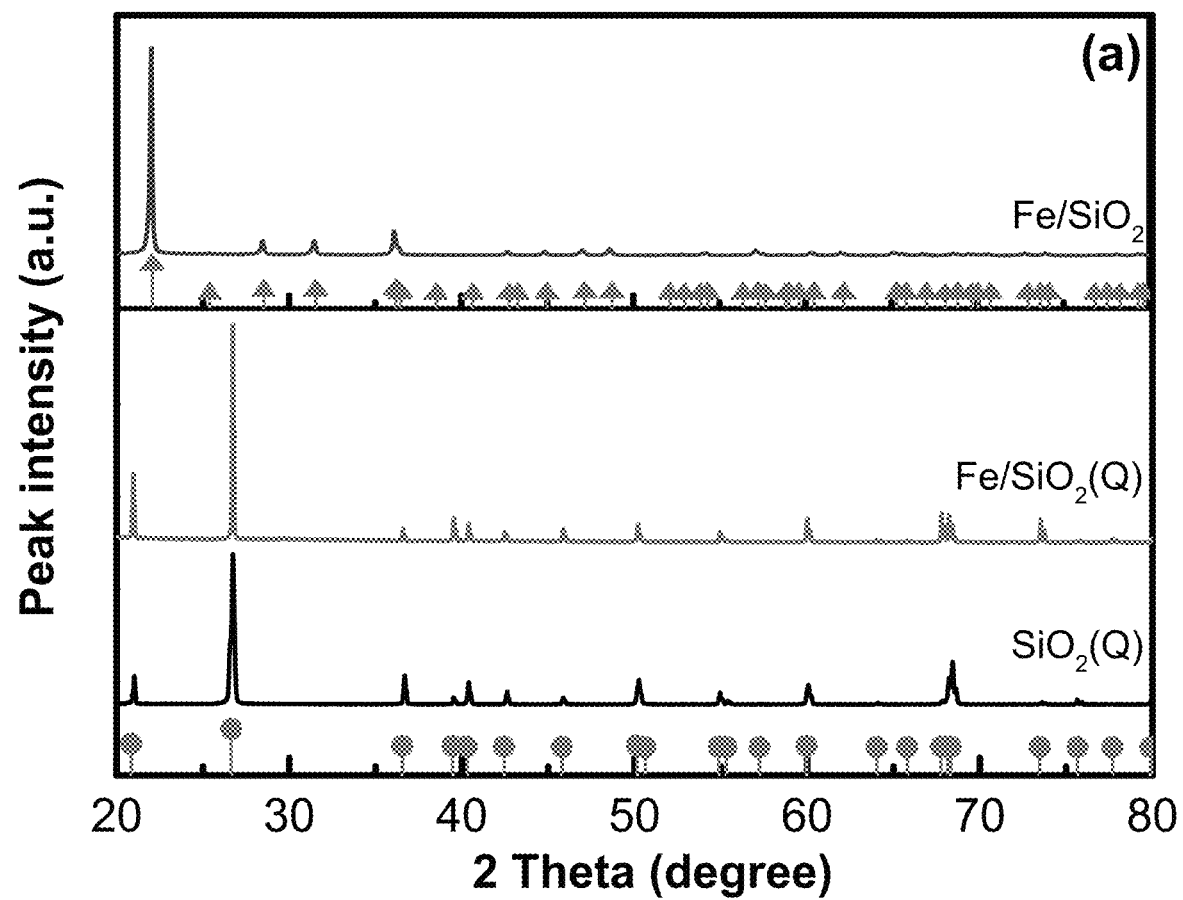
FIG. 15A shows XRD patterns $Fe/SiO_2$, $SiO_2(Q)$ and $Fe/SiO_2(Q)$ materials. ※ and ❈ stand for α-cristobalite and α-quartz crystalline phases, respectively.

The Fe/SiO$_2$(Q) catalyst prepared by the flame-fusing method was firstly characterized for structural properties prior to the DNMC tests. FIG. 15A shows the XRD patterns of Fe/SiO$_2$(Q), Fe/SiO$_2$ and SiO$_2$(Q) materials. SiO$_2$(Q) is the support precursor of Fe/SiO$_2$(Q) and Fe/SiO$_2$ catalysts, and Fe/SiO$_2$ was prepared by the high-temperature (1973 K) melting method. The appearance of the same pattern of XRD peaks between Fe/SiO$_2$(Q) and SiO$_2$(Q) indicates there was no crystalline phase change in the catalyst preparation process. The catalyst support maintains the α-quartz phase. The Fe/SiO$_2$ sample, however, shows different XRD pattern to SiO$_2$(Q), indicating a crystalline phase change in the high temperature melting process. The SiO$_2$ support in the Fe/SiO$_2$ sample belongs to the α-cristobalite phase.

Figure 15B:
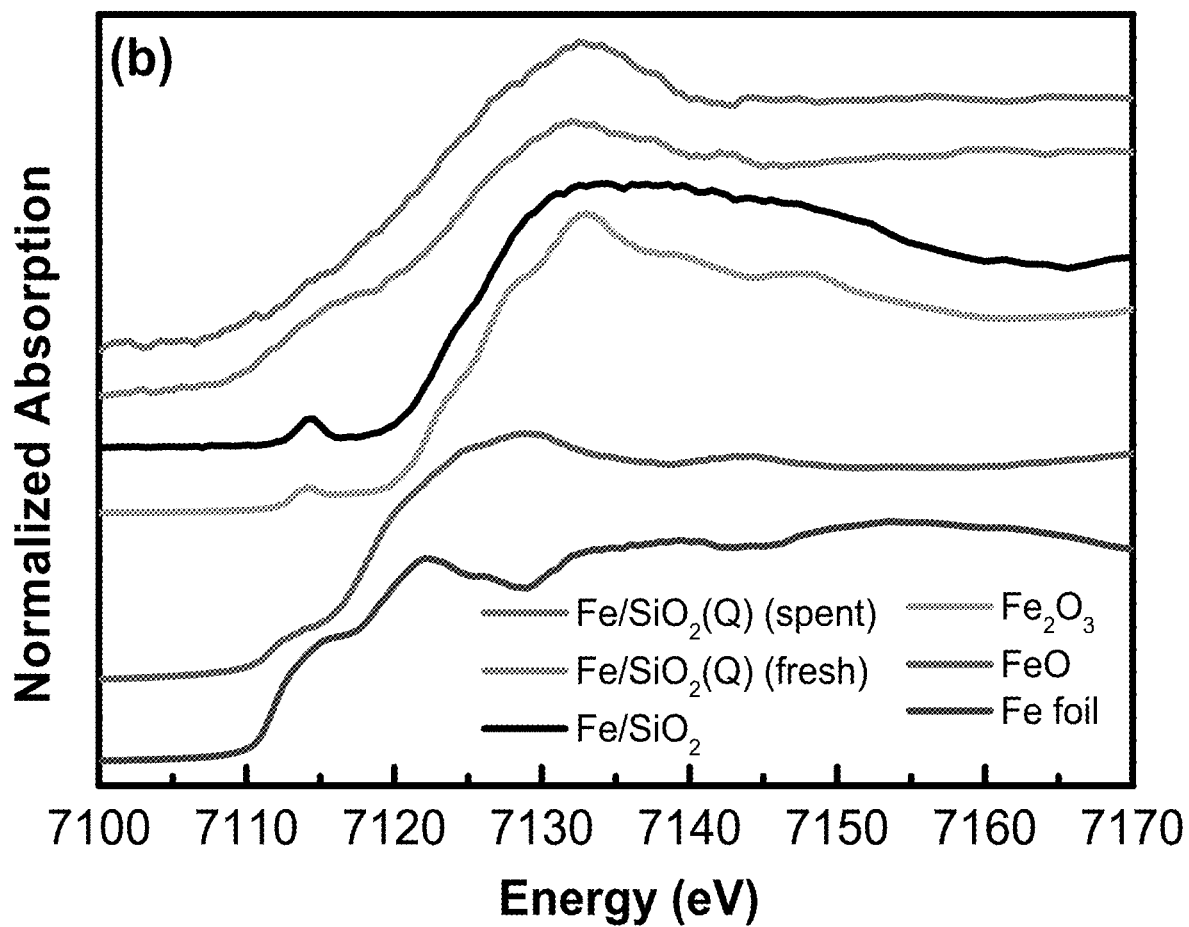
FIG. 15B shows Fe K-edge near-edge spectra showing coordination environment of Fe species in $Fe/SiO_2(Q)$ catalyst.

FIG. 15B shows the XANES spectra of fresh and spent (after 15 minutes DNMC test) Fe/SiO$_2$(Q) catalysts, together with FeO, Fe foil and Fe$_2$O$_3$ samples for comparison purposes. Both Fe$_2$O$_3$ and FeO exhibited a pre-edge peak, which is indicative of a 1 s-3d transition in Fe$^{3+}$ on tetrahedral sites. It was also observed that the white line position of Fe$_2$O$_3$ appeared at a higher energy than that of FeO due to its higher oxidation number. The fresh Fe/SiO$_2$ (Q) catalyst exhibited white lines at similar position to that of FeO. Compared with those of the fresh catalyst, the XANES profiles of spent Fe/SiO$_2$(Q) catalysts were similar to those of Fe foil. The shift in edge energy position in the spent catalysts implies that a reduction of Fe$^{3+}$ or Fe$^{2+}$ to Fe$^0$ occurred during the reaction. The coordination status of Fe species in Fe/SiO$_2$(Q) prepared by the flame-fusing method is different from that of Fe/SiO$_2$ prepared by the high-temperature melting method since the XAS data of the latter sample show that Fe-species has similar coordination environment to that of Fe$_3$O$_4$, according to precious reports.

Figure 16A:
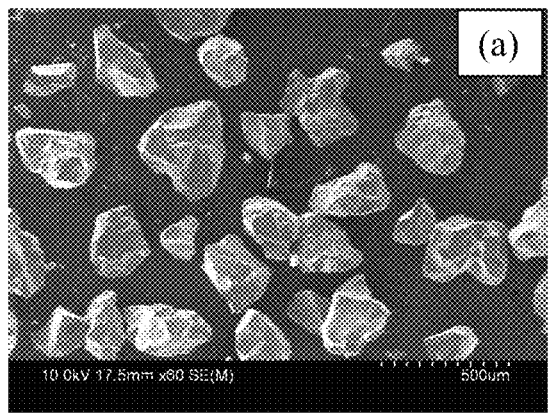
FIG. 16A is an SEM image of $Fe/SiO_2(Q)$ catalyst at 500 μm.
Figure 16B:
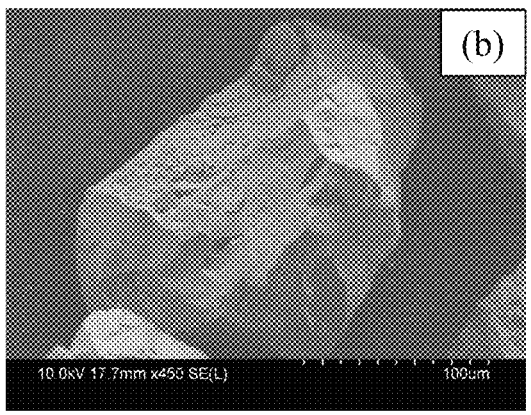
FIG. 16B is an SEM image of $Fe/SiO_2(Q)$ catalyst at 100 μm.
Figure 16C:
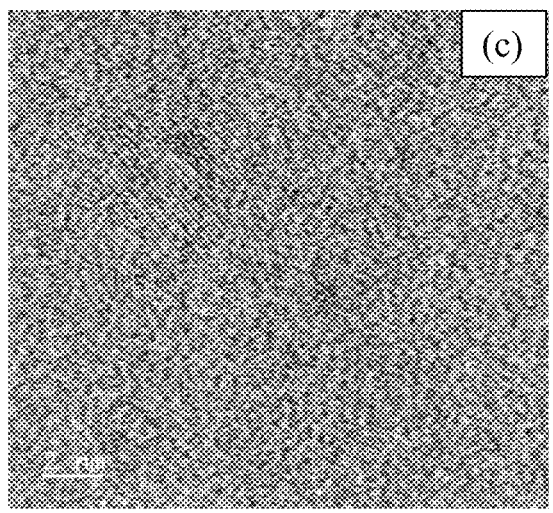
FIG. 16C is a HR-TEM image showing morphology of Fe species and quartz lattice structure in $Fe/SiO_2(Q)$ catalyst.
Figure 16D:
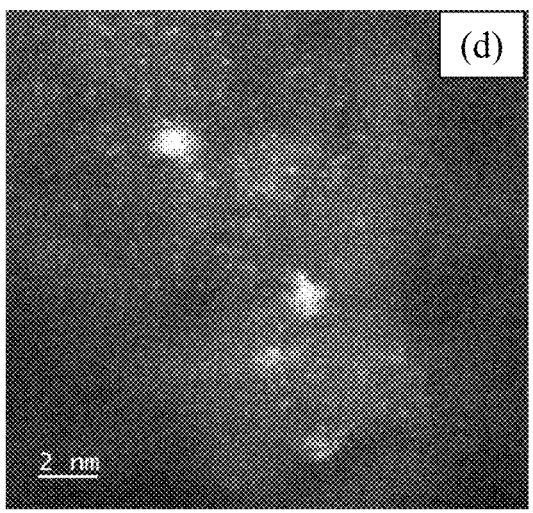
FIG. 16D is a STEM-HAADF image showing morphology of Fe species in $Fe/SiO_2(Q)$ catalyst.

The morphologies of the catalyst surfaces and Fe species in the fresh Fe/SiO$_2$(Q) catalysts were investigated by SEM analyses as shown in FIGS. 16A and 16B and by TEM analyses as shown in FIG. 16C. The particle sizes are in the range of sub-millimeters. This is consistent with its low surface area of 0.4 m$^2$ g$^{-1}$, as measured by the BET method from the N$_2$ isotherm. There are no clear iron oxide nanoparticles visible in the Fe/SiO$_2$(Q) catalyst. This could be attributed to the low concentration of Fe-species in the catalyst, which contains 0.075% Fe as determined by the ICP-OES analysis. The isolated nature of the Fe sites was evidenced by sub-angstrom-resolution high-angle annular-dark field (HAADF) scanning transmission electron microscopy (STEM) in FIG. 16D. The STEM-HAADF image of the Fe/SiO$_2$(Q) catalyst reveals many bright dots of atomic size scattered across the SiO$_2$(Q) matrix. Each dot represents an individual Fe atom, considering the much lower contrast of Si and O in the HAADF image. This result suggests that the iron species are distributed as isolated atoms during the catalyst preparation for the DNMC reactions.

Catalytic Performance of Fe/SiO$_2$(Q) in Oxidative Co-Fed DNMC Reactions

DNMC Reactions on Fe/SiO$_2$(Q) with O$_2$ Co-Feed

Figure 17A:
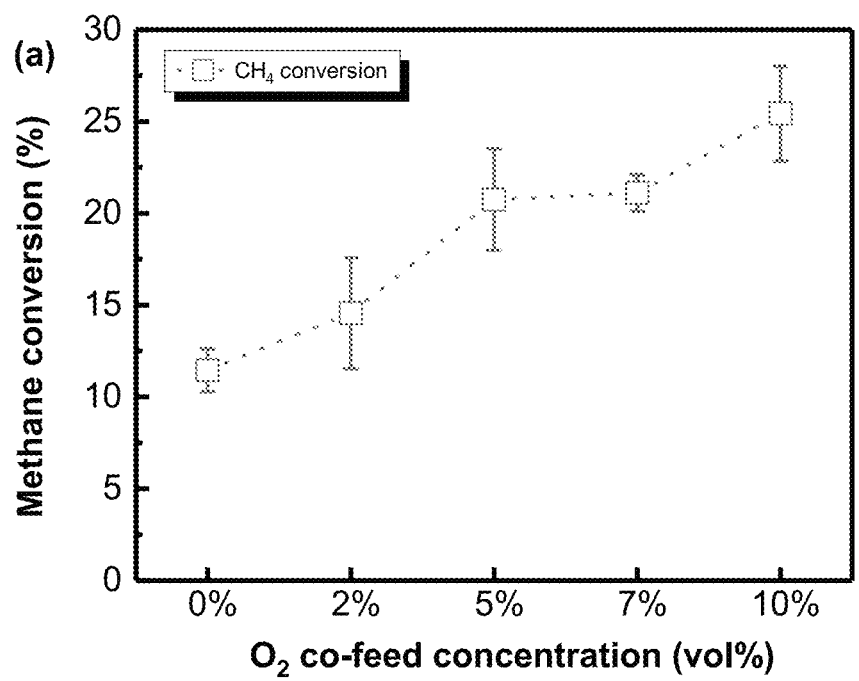
FIG. 17A shows methane conversion for $O_2$ co-feed volume concentrations of 2 vol %, 5 vol %, 7 vol % and 10 vol % in DNMC. Error bars are standard deviation values of methane conversion from multiple (>3 times) repeating experiments.
Figure 17B:
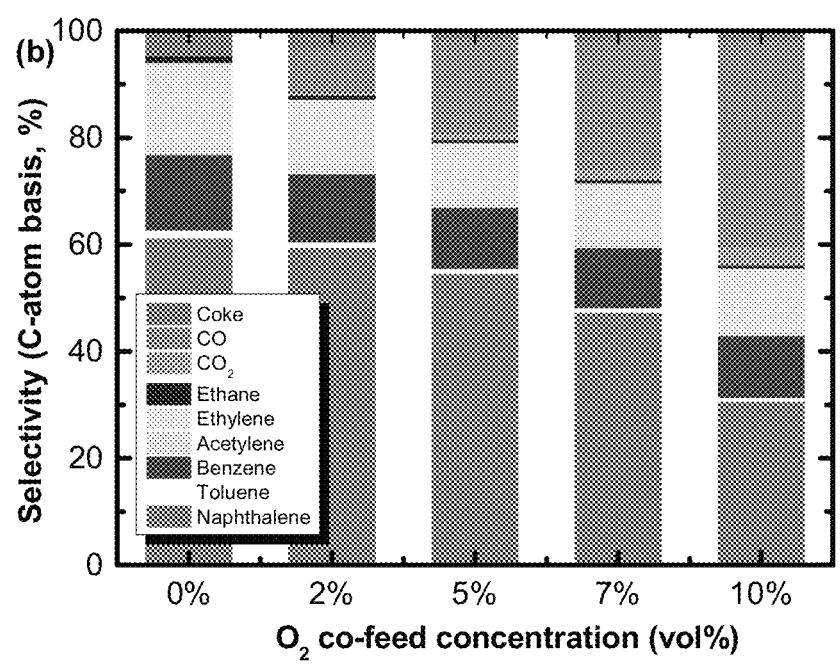
FIG. 17B shows product selectivity for $O_2$ co-feed volume concentrations of 2 vol %, 5 vol %, 7 vol % and 10 vol % in DNMC.

The oxidative O$_2$ co-feed was added into the methane stream at concentrations of 2 vol %, 5 vol %, 7 vol %, and 10 vol % to test its effects on the performance of the Fe/SiO$_2$(Q) catalyst in the DNMC reaction. FIGS. 17A-17B show the methane conversion and product selectivity measured in each case. The performance of the catalyst in DNMC in the absence of O$_2$ co-feed was included in FIGS. 17A-17B for comparison. The O$_2$ co-feed increased the methane conversion beyond that of the methane-only reaction over Fe/SiO$_2$(Q), with further improvements on methane conversion occurring with increasing O$_2$ concentrations. The methane conversion was 11.45% in the absence of any O$_2$ co-feed and increased to 14.56%, 20.75%, 21.11%, and 25.43% in sequence with O$_2$ concentration from 2 vol % to 10 vol %. The product selectivity was changed accordingly with different O$_2$ co-feed concentrations. In the absence of O$_2$ co-feed, the product distribution mainly contains naphthalene (60.78%), benzene (14.04%), and ethylene (15.17%), accompanied with small amounts of acetylene (2.10%), ethane (1.17%), toluene (2.02%) and coke (4.71%). The presence of O$_2$ in the methane feed led to formation of CO$_2$ and CO products in addition to the species produced from the co-feed free reaction listed above. The selectivity toward these two oxidized products increased with increasing O$_2$ co-feed. The selectivities toward all hydrocarbon products decreased, and the same trend is observed for coke selectivity.

Figure 17C:
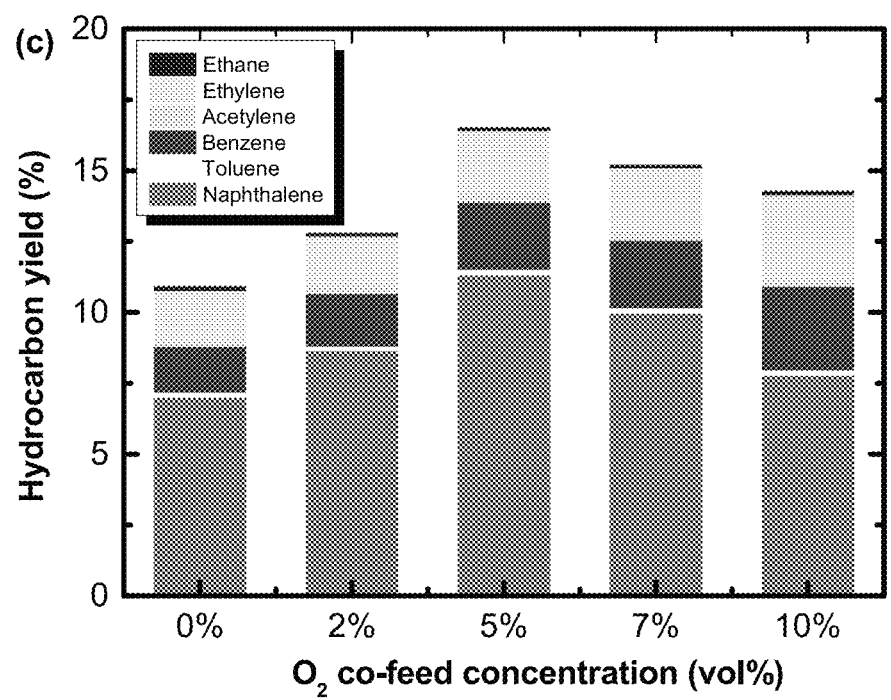
FIG. 17C shows hydrocarbon product for $O_2$ co-feed volume concentrations of 2 vol %, 5 vol %, 7 vol % and 10 vol % in DNMC.
Figure 17D:
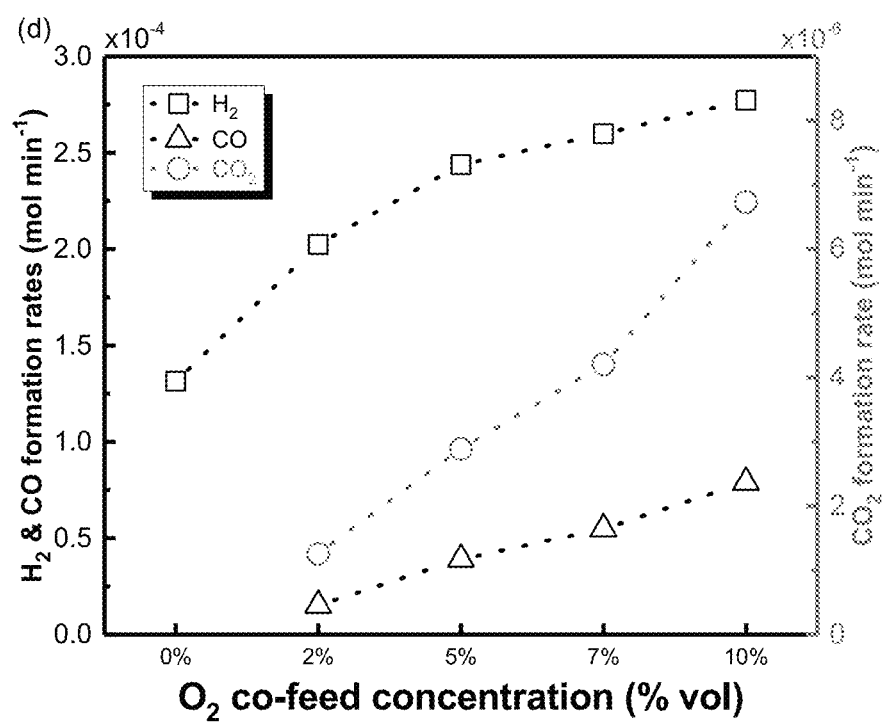
FIG. 17D shows $H_2$, CO and $CO_2$ formation rates for $O_2$ co-feed volume concentrations of 2 vol %, 5 vol %, 7 vol % and 10 vol % in DNMC.

FIG. 17C shows hydrocarbon product yields from the DNMC reaction over the Fe/SiO$_2$(Q) catalyst in the absence and presence of O$_2$ co-feed at the four different concentrations. Although the hydrocarbon product selectivities were reduced in each case involving O$_2$ co-feed, their yield, however, exhibited interesting behavior, i.e. a volcano-shape, with increasing O$_2$ concentrations. For instance, the C$_2$+ yields were 10.91%, 12.72%, 16.28%, 14.92%, and 13.85, corresponding to O$_2$ co-feed concentrations of 0 vol %, 2 vol %, 5 vol %, 7 vol % and 10 vol % in sequence. The C$_2$+ yield was maximized at an O$_2$ concentration of 5 vol %. If we consider the individual hydrocarbon product yields in FIG. 17C, it is interesting to see that the naphthalene yield follows the same volcano trend as that of the C$_2$+ products. The yield of ethylene or benzene, however, continued increasing with increasing O$_2$ co-feed concentrations. The coke yield is 0.54%, 0.44%, 0.39%, 0.40%, and 0.47% for O$_2$ concentrations of 0 vol % to 10 vol %, respectively, demonstrating an inverse trend to that of the C$_2$+ yields, with the minimum coke yield existing at the 5 vol % O$_2$ co-feed concentration. The current market analysis shows that ethylene and benzene are more valuable products than naphthalene across industries; the capability of increasing ethylene and benzene product yields by introducing an O$_2$-cofeed in the methane feed stream offers a new approach for producing more valuable hydrocarbon products from the DNMC process.

DNMC Reactions on Fe/SiO$_2$(Q) with CO Co-Feed

Figure 18A:
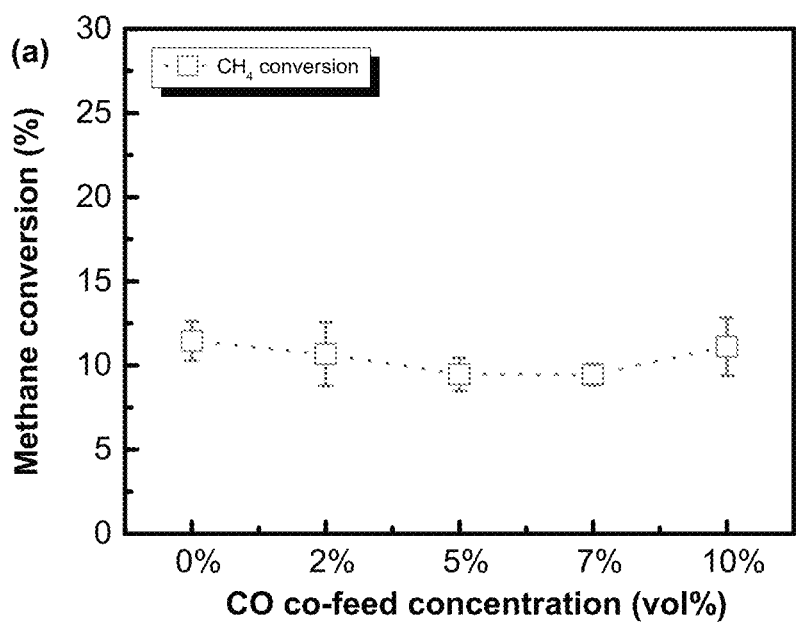
FIG. 18A shows methane conversion for CO co-feed volume concentrations of 2 vol %, 5 vol %, 7 vol % and 10 vol % in DNMC. Error bars are standard deviation values of methane conversion from multiple (>3 times) repeating experiments.
Figure 18B:
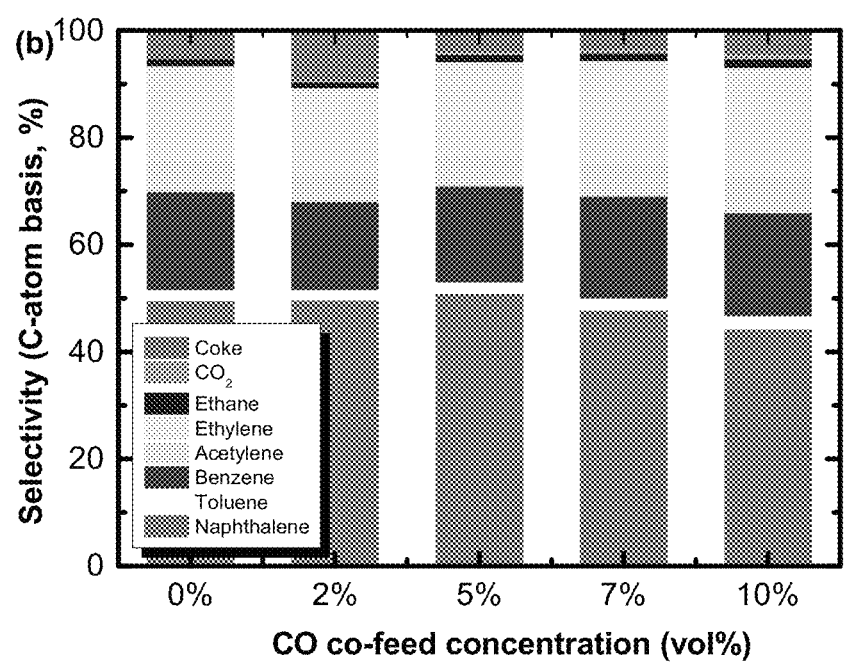
FIG. 18B shows product selectivity for CO co-feed volume concentrations of 2 vol %, 5 vol %, 7 vol % and 10 vol % in DNMC.
Figure 18C:
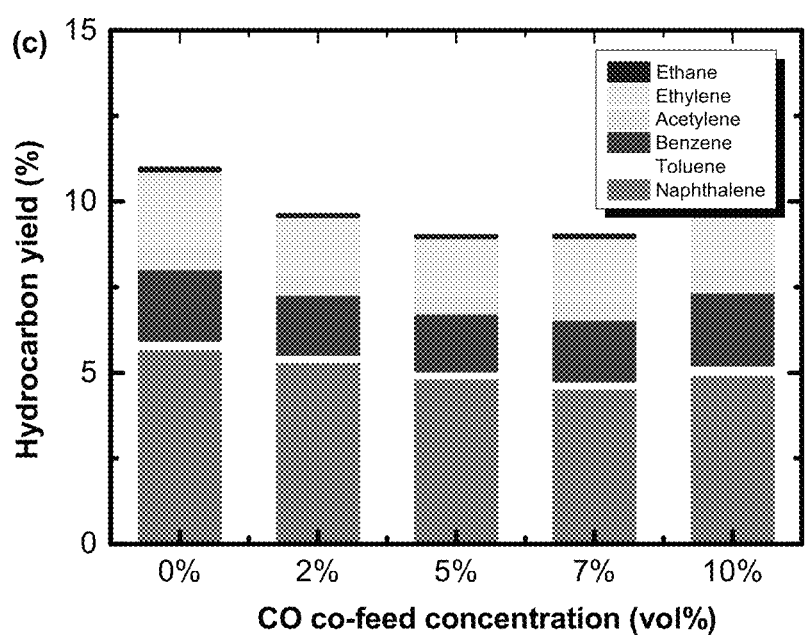
FIG. 18C shows hydrocarbon product yield for CO co-feed volume concentrations of 2 vol %, 5 vol %, 7 vol % and 10 vol % in DNMC.
Figure 18D:
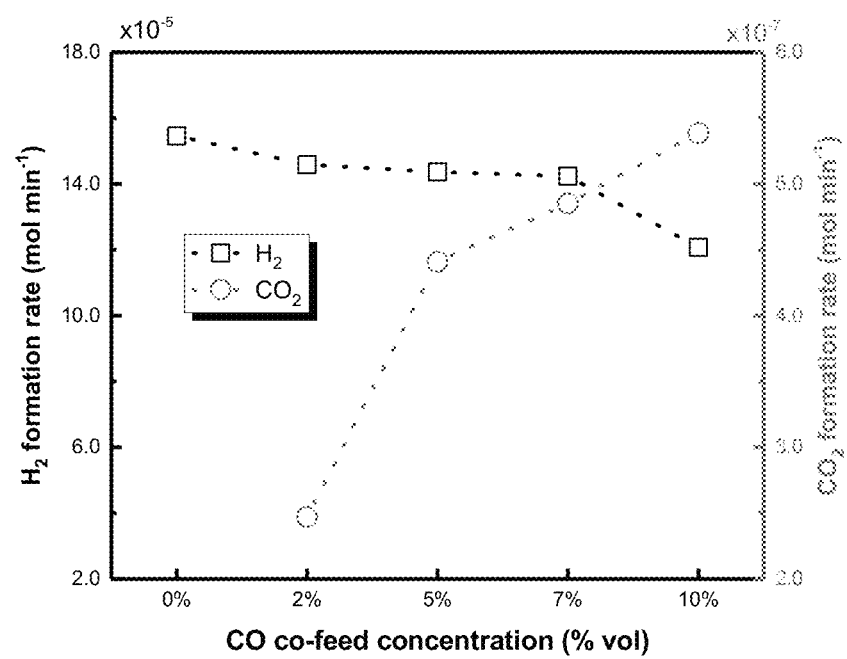
FIG. 18D shows $H_2$ and $CO_2$ formation rates for CO co-feed volume concentrations of 2 vol %, 5 vol %, 7 vol % and 10 vol % in DNMC.

Since CO is one of the dominant by-products in the O$_2$ co-fed DNMC reaction, we purposely examined the effect of CO addition in the methane stream on the DNMC over the Fe/SiO$_2$(Q) catalyst. FIGS. 18A-D show the methane conversion, product selectivity and hydrocarbon product yield, and H$_2$ and CO$_2$ formation rates at the CO concentrations of 0 vol %, 2 vol %, 5 vol %, 7 vol % and 10 vol %, respectively. In the tested CO concentration range, the methane conversion (FIG. 18A) and product selectivity (FIG. 18B) were kept nearly constant, which led to comparable hydrocarbon product yields across the tested CO concentration range (FIG. 18C). FIG. 18D shows that the formation rate of H$_2$ did not change obviously with the CO co-feed. The CO$_2$ formation rate was increased with an increase in CO concentration in the methane stream, but its rate was low, more than 200-fold lower than that of H$_2$ by-product. The CO co-feed showed trivial impact on performance of the DNMC reaction.

The CO co-feed primarily interacts with the Fe/SiO$_2$(Q) and CH$_4$ reactant in the DNMC reaction. The low oxidation status of Fe-species in the catalyst hints that CO is not necessary to reduce active sites to activate methane reactant. The thermodynamics of CO interaction with CH$_4$ or higher hydrocarbons or H$_2$ by-product in the DNMC reaction determines that these reactions are not favorable. As noted by in previous studies on effects of CO co-feed on DNMC over the Mo/ZSM-5 catalyst, the O atom in CO can only be used to produce another CO or to form water. The water formed would react with the predominant CH$_4$ reactant to re-form CO and H$_2$. Overall, there is no reasonable reaction stoichiometry or pathway for CO involvement in the DNMC chemistry, and thus we did not observe consistent and obvious impact of CO co-feed on the DNMC over the Fe/SiO$_2$(Q) catalyst. The slight increase in CO$_2$ formation could be due to the Boudouard reaction (2 CO→CO$_2$+C) at the tested DNMC conditions.

DNMC Reactions on Fe/SiO$_2$(Q) with CO$_2$ Co-Feed

Figure 19A:
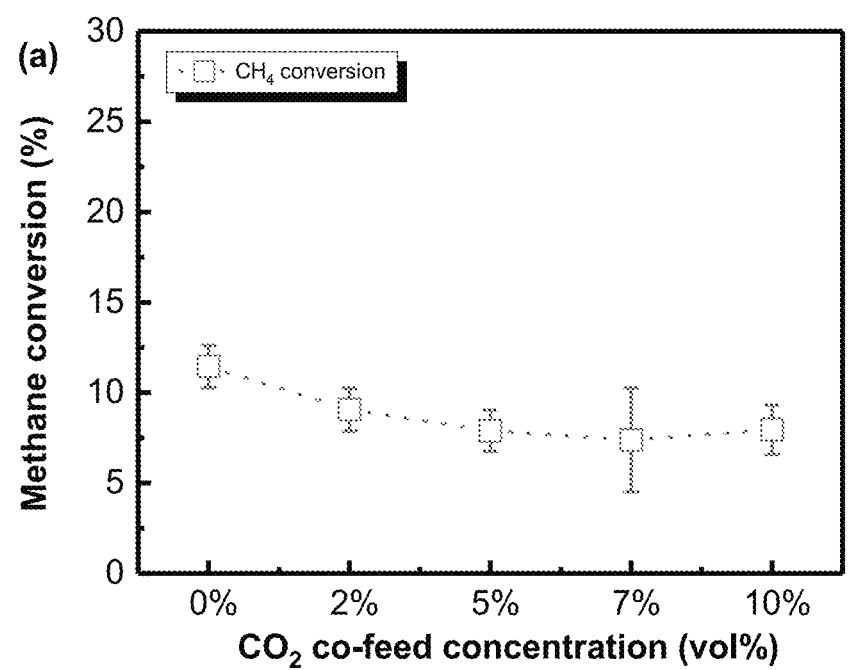
FIG. 19A shows methane conversion for $CO_2$ co-feed volume concentrations of 2 vol %, 5 vol %, 7 vol % and 10 vol % in DNMC. Error bars are standard deviation values of methane conversion from multiple (>3 times) repeating experiments.
Figure 19B:
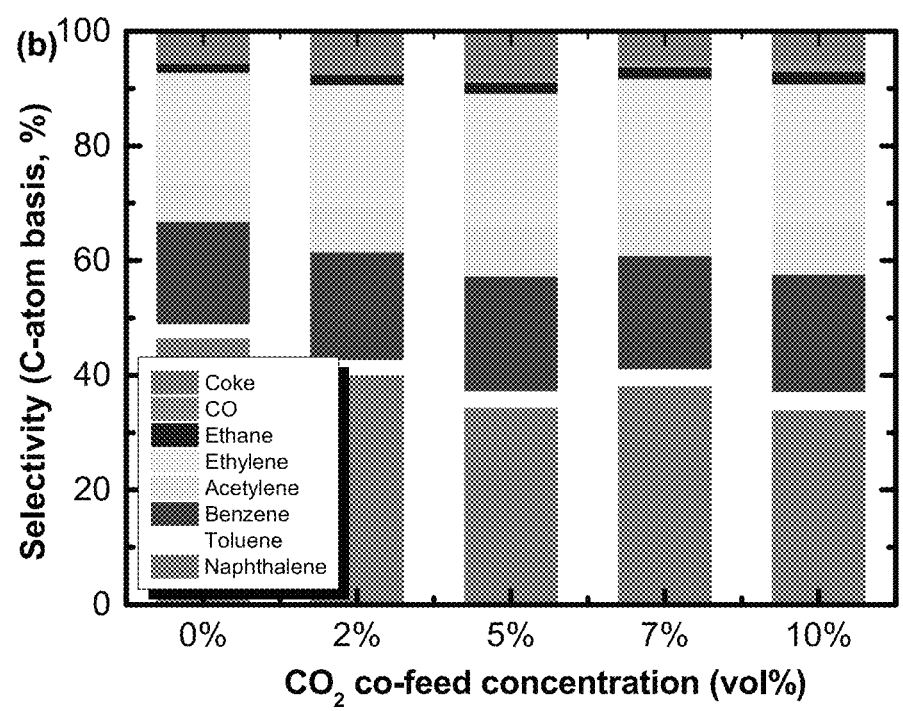
FIG. 19B shows product selectivity for $CO_2$ co-feed volume concentrations of 2 vol %, 5 vol %, 7 vol % and 10 vol % in DNMC.
Figure 19C:
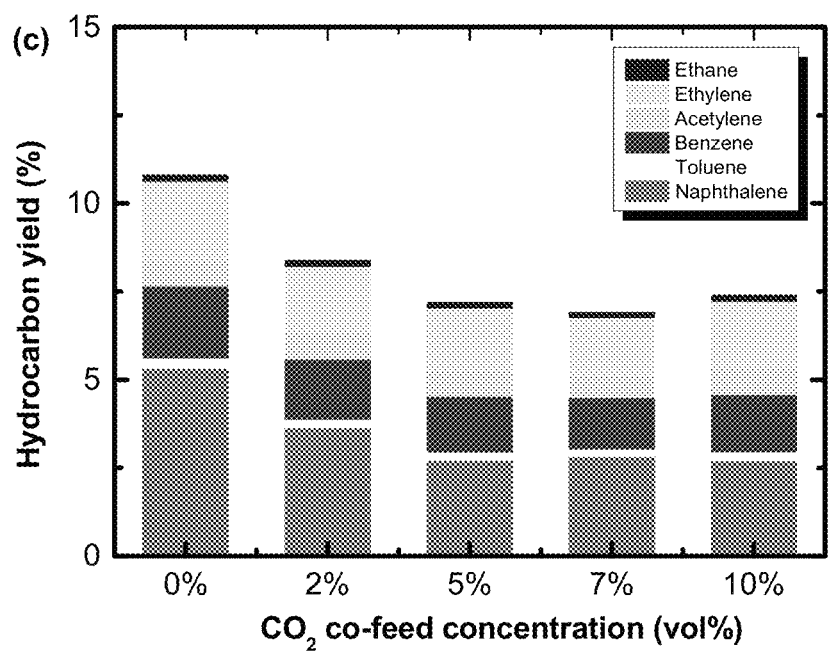
FIG. 19C shows hydrocarbon product yield for $CO_2$ co-feed volume concentrations of 2 vol %, 5 vol %, 7 vol % and 10 vol % in DNMC.

Carbon dioxide was co-fed into the methane feed stream at varying concentrations and had an overall negative impact on methane conversion and product yield. As shown in FIG. 19A, a decline in methane conversion with increasing CO$_2$ concentration in the feed was observed. The selectivity of ethylene and benzene shows slight increases accompanied with slight reduction in naphthalene selectivity with higher CO$_2$ concentrations. Coke selectivity was increased and then decreased with increasing CO$_2$ co-feed. The CO formation was kept increasing with increasing CO$_2$ in the feed stream. The ethane and acetylene selectivities are hard to determine due to their small numbers in FIG. 19C. Although there was an improvement in ethylene and benzene selectivity with the introduction of CO$_2$ into the feed stream, this was offset by the significant drop in methane conversion as is demonstrated by the hydrocarbon yield data presented in FIG. 19C. This effect was also noted by Rodrigues and Monteiro[7] when co-feeding $CO_2$ into the DNMC reaction using Mo/ZSM-5 catalyst.

Figure 19D:
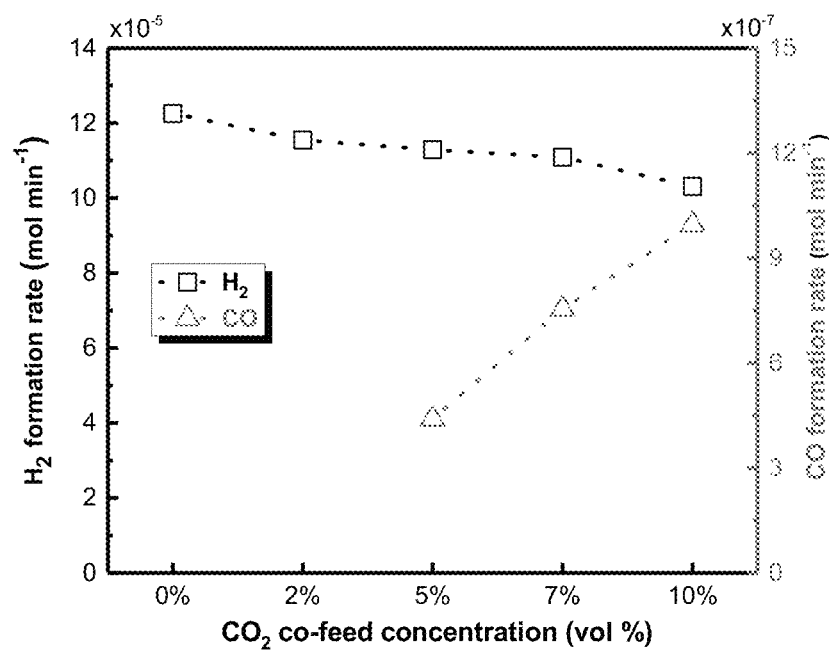
FIG. 19D shows $H_2$ and CO formation rates for $CO_2$ co-feed volume concentrations of 2 vol %, 5 vol %, 7 vol % and 10 vol % in DNMC.

The primary reaction between $CO_2$ co-feed in the DNMC should be dry reforming of methane ($CO_2+CH_4\rightarrow 2$ $CO+2H_2$), which produces syngas and is thermodynamically feasible at 1273 K. The CO product is not expected to impair the DNMC performance, as indicated by the CO co-feed study above. The $H_2$ product, however, could decrease the methane conversion significantly, as indicated by the $H_2$ co-feed study in our previous work. The dry reforming of $CO_2$ with any other hydrocarbon products would lead to similar effects to that of methane reactant. In addition, the reverse Boudouard reaction ($CO_2+C\rightarrow 2$ CO) could contribute to the CO formation. Therefore, the CO product rate increased with $CO_2$ co-feed concentrations. The decrease in methane conversion lowered the $H_2$ formation rate, as shown in FIG. 19D. Hydrogen and oxygen balances were performed on the system, and closed balances were obtained for both elements, indicating that there was no net production of water. The production of methane and carbon dioxide via this pathway is a possible explanation for the decreasing methane conversion and low CO production under $CO_2$ co-feed conditions.

Reaction Autothermality of DNMC on Fe/SiO$_2$(Q) with O$_2$ Co-Feed

Figure 20:
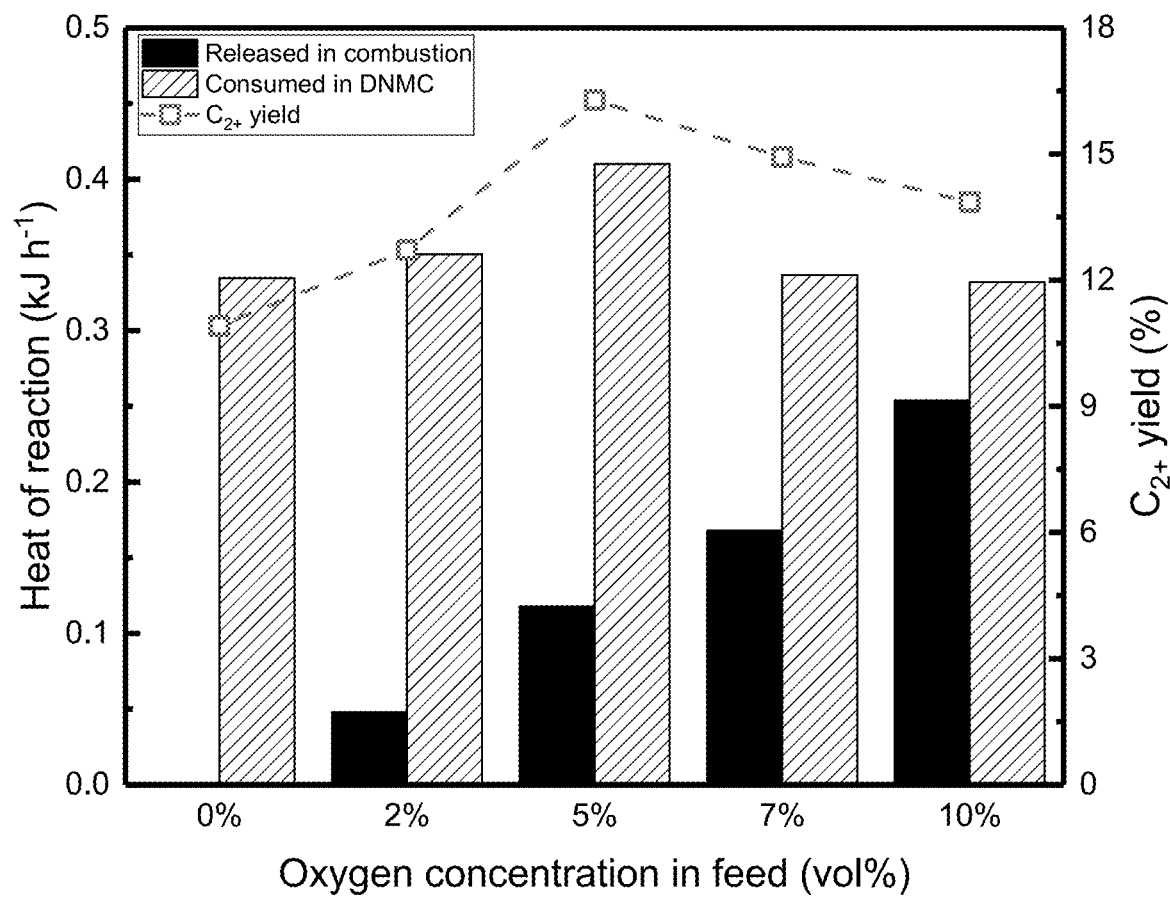
FIG. 20 shows heat of reaction for formation of hydrocarbon products in DNMC and heat of release for formation of CO, $CO_2$ and $H_2O$ in oxidative reactions due to $O_2$ co-feed.

The formation of CO and $CO_2$ in the product stream suggests the methane oxidation reaction accompanied the DNMC reaction when $O_2$ was introduced into the methane feed. The formation of CO and $CO_2$ from methane are exothermic reactions, while DNMC is a highly endothermic reaction. A thermodynamics calculation was conducted to examine the endothermicity and exothermicity of the entire reaction process. As shown in FIG. 20, the heat required for the DNMC reaction increases and then decreases with increasing $O_2$ co-feed concentration, whereas the heat released from the combustion of methane follows the monotonically increasing trend, increasing with the higher $O_2$ co-feed concentrations. The heat required and produced during the simultaneous reactions could be balanced when $O_2$ is kept increasing to a concentration of ~15 vol %.

Overall, introduction of an $O_2$-cofeed demonstrated a direct relationship between higher co-feed concentrations and increased methane conversion as well as yields of CO, $CO_2$, ethylene and benzene products. The inverse trend for coke and naphthalene yields were observed with increasing $O_2$ concentration in the methane feed. The formation of hydrocarbon products is due to the DNMC reaction, although the detailed mechanism remains unclear. The formation of CO and $CO_2$ are apparently from oxidation reactions between the $O_2$ oxidant and hydrocarbons involved in the DNMC reaction network. Many species could contribute to the oxidation reactions, but the mitigation of heavy compounds such as coke and naphthalene products seems to be dominant. Although the formation of CO and $CO_2$ was observed in this study, the increase in $C_2$ and benzene yield in the DNMC reaction offsets this negative effect. By controlling $O_2$ concentration, maximization of $C_{2+}$ yield was achievable compared to the pure methane feed in DNMC.

Coke Composition Analysis on Spent Fe/SiO$_2$(Q) Catalysts

Figure 21:
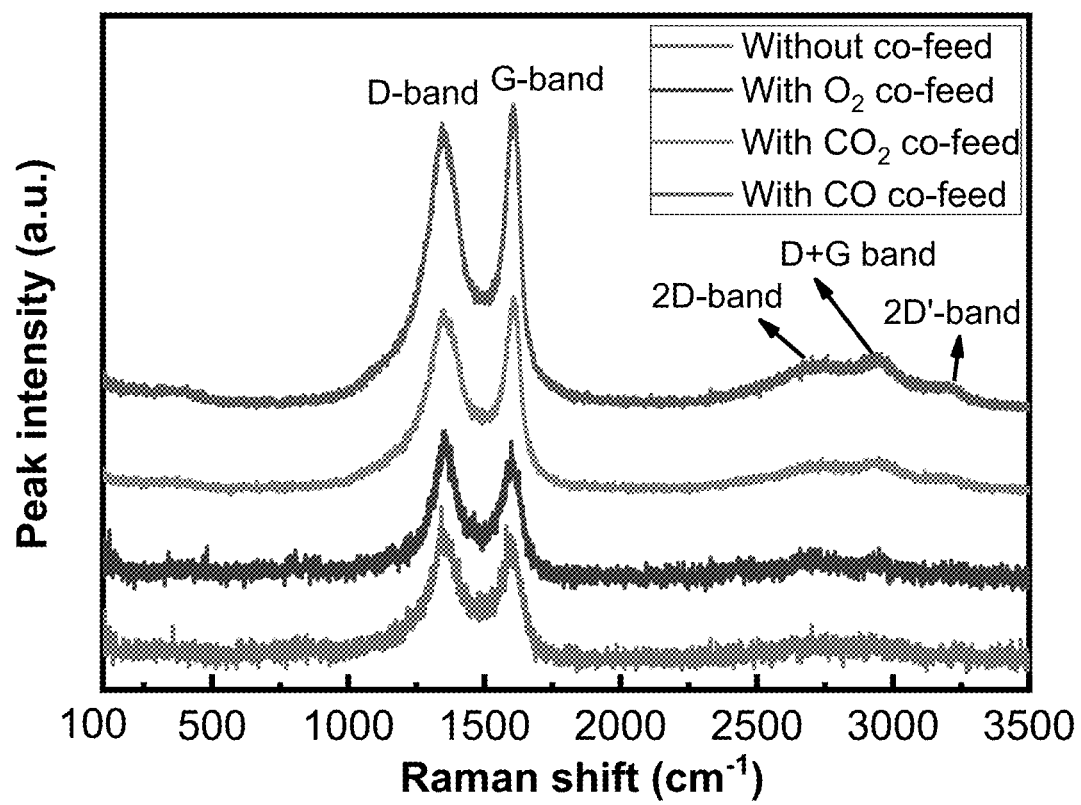
FIG. 21 shows Raman spectroscopy of spent $Fe/SiO_2(Q)$ catalyst in methane-only and 5 vol % co-feed DNMC reactions.
Figure 22A:
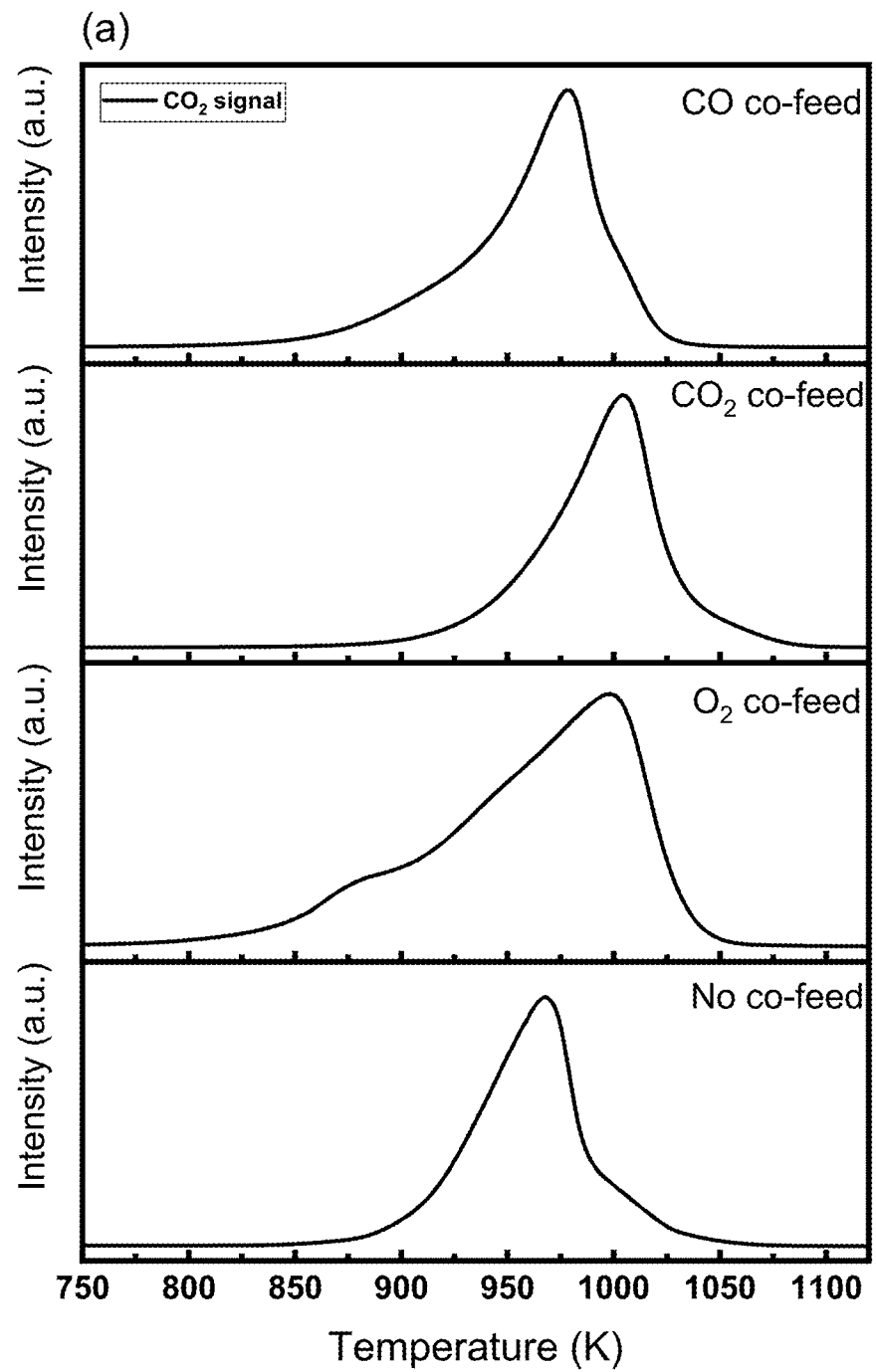
FIG. 22A shows temperature-programmed oxidation (TPO) results ($CO_2$ product profile) for spent $Fe/SiO_2(Q)$ catalysts following reactions under conditions of (i) no co-feed, (ii) 5 vol % $O_2$ co-feed, (iii) 5 vol % $CO_2$ co-feed, and (iv) 5 vol % CO co-feed. TPO test conditions: 10 vol % $O_2$/He, 30 mL/min, 10K/min ramp to 1123K with 30 minutes hold.
Figure 22B:
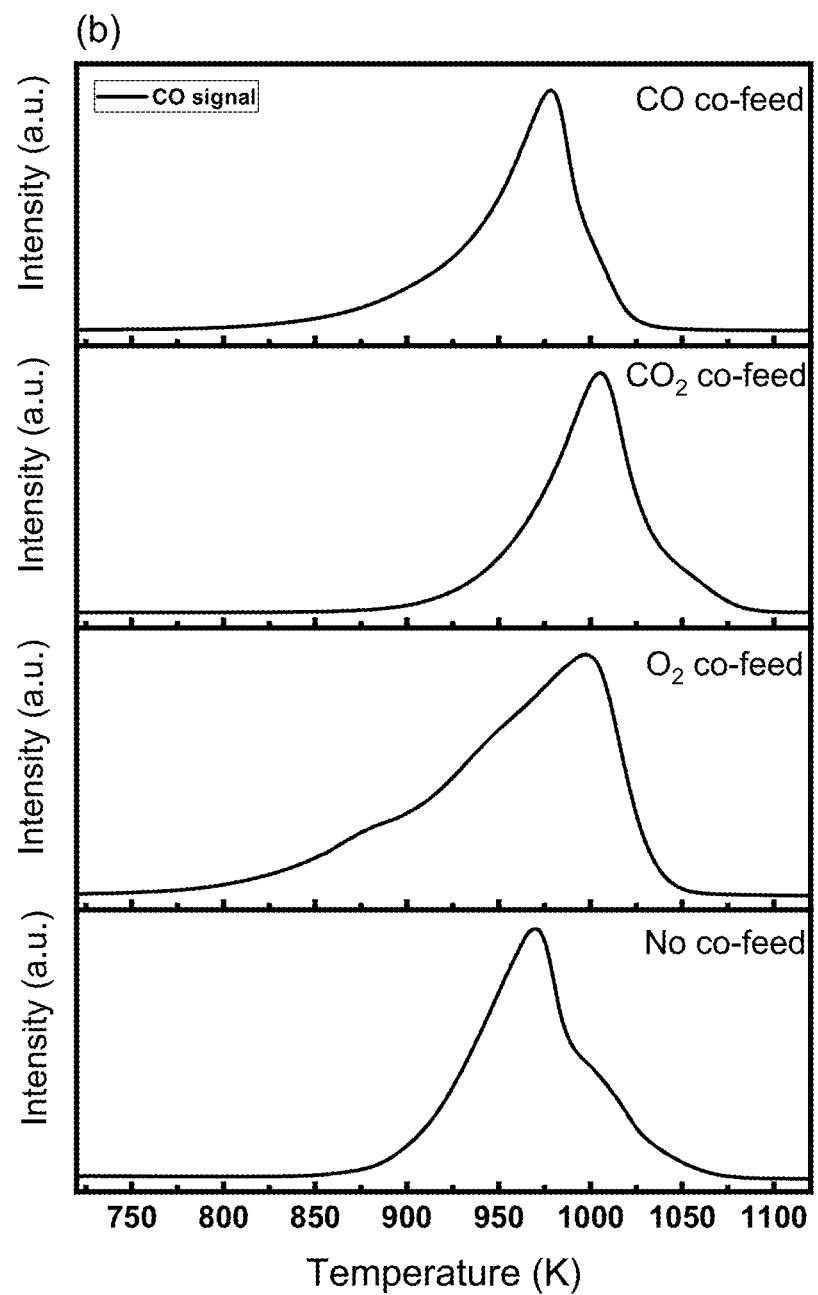
FIG. 22B shows Temperature-programmed oxidation (TPO) results (CO product profile) for spent $Fe/SiO_2(Q)$ catalysts following reactions under conditions of (i) no co-feed, (ii) 5 vol % $O_2$ co-feed, (iii) 5 vol % $CO_2$ co-feed, and (iv) 5 vol % CO co-feed. WO test conditions: 10 vol % $O_2$/He, 30 mL/min, 10K/min ramp to 1123 K with 30 minutes hold.

The type of coke on the catalyst samples was first measured by the Raman spectroscopy (FIG. 21). The presence of both D- and G-band in all samples indicates both amorphous and graphitic carbon exist in the coke. The composition of coke species on the spent catalyst was studied by the temperature-programmed oxidation (TPO) experiments, where oxygen was used to combust the coke present on the spent catalysts. The coke is assumed to be primarily carbonaceous, as the products from the TPO experiment mainly consisted of oxidized carbon species, and no water was detected in the measurement. The black, solid lines in FIGS. 22A and 22B illustrate the $CO_2$ and CO profiles resulting from $O_2$-induced coke combustion. The asymmetrical, broadened peaks resulted from multiple instances of coke combustion at different temperatures. The $CO_2$ and CO spectra obtained from the catalyst used in the $O_2$ co-fed DNMC reaction displayed the widest range of combustion temperatures, with an onset of 775 K and completion occurring at 1075 K, a span of 300 K. Spent catalysts following reactions with no co-feed, $CO_2$ co-feed, and CO co-feed exhibited combustion activity in smaller ranges of 850 K to 1075 K, 875 K to 1100 K, and 825 K to 1050 K, respectively, all of which occur across a 225 K temperature span. The shifting combustion temperatures and relative peak areas within the deconvoluted $CO_2$ and CO spectra among the four samples (FIGS. 22A and 22B) indicate a variation in coke morphologies and bonding environments between the carbon species and catalysts.

Figure 23:
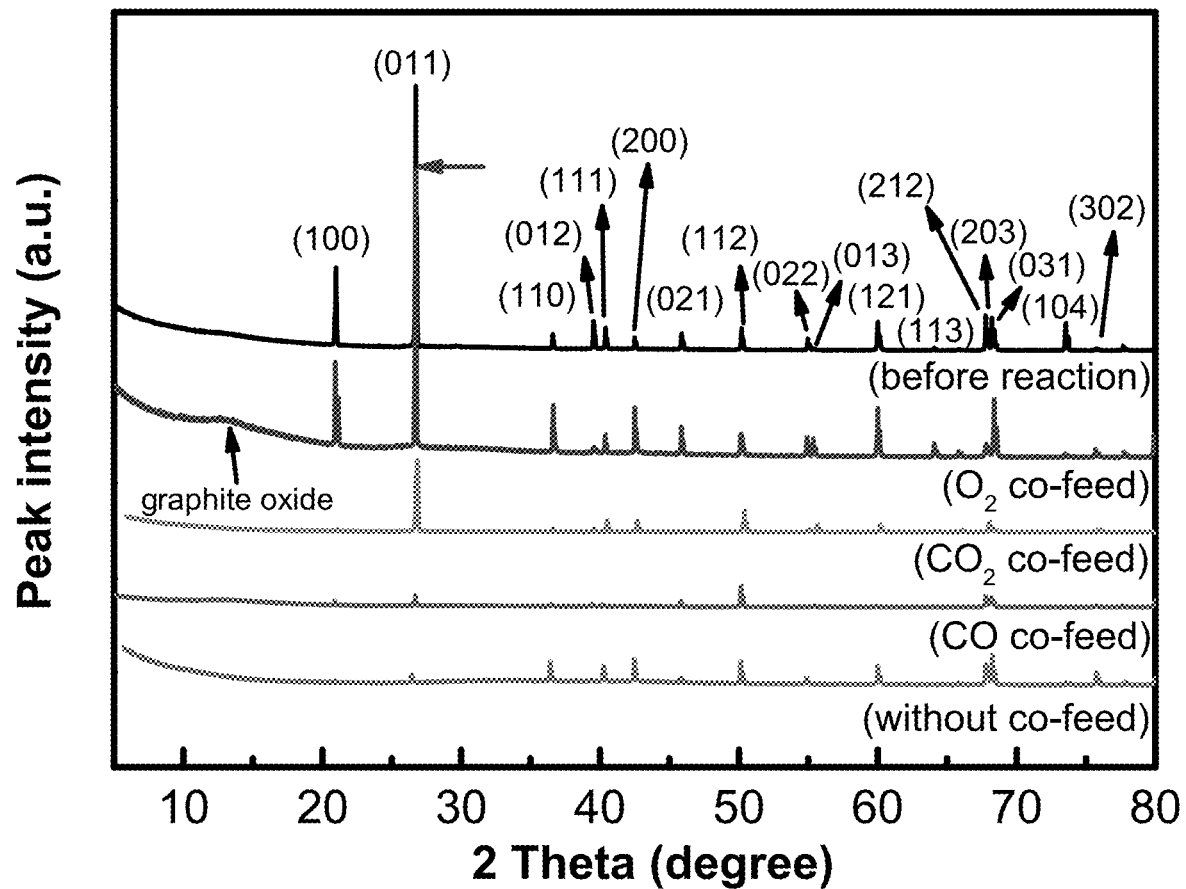
FIG. 23 shows powder XRD patterns for fresh $Fe/SiO_2$ (Q) catalyst and of spent catalysts run with no co-feed and at 7 vol % co-feeds for $O_2$, $CO_2$, and CO. The broad graphite oxide peak is shown with a dotted line at the peak maxima. All other XRD peaks can be attributed to quartz.

Structural Analysis of Spent Fe/SiO$_2$(Q) Catalysts in Different Oxidative Co-Feeds To probe the effects of oxidative co-feed on the crystalline structure change of the Fe/SiO$_2$(Q) catalyst, we firstly measured XRD patterns of the spent Fe/SiO$_2$(Q) catalysts following the DNMC reaction under no co-feed and 7 vol % oxidative co-feed conditions for each oxidant. FIG. 23 compares the XRD results of these spent catalysts both to each other and to the fresh (i.e. before reaction) Fe/SiO$_2$(Q) material. The Fe/SiO$_2$(Q) catalyst after the DNMC test without any co-feed showed the same XRD pattern to that of fresh Fe/SiO$_2$(Q). This indicates that the DNMC reaction condition did not change the crystalline structure of the quartz material. The (100) and (011) peaks of the quartz in the Fe/SiO$_2$(Q) catalyst decreased significantly, which could be attributed to the uneven coke deposition on the catalyst responsible for obscuring certain faces of the crystalline quartz material. The Fe/SiO$_2$(Q) catalyst after the DNMC reaction with $O_2$ co-feed still kept the quartz crystalline phase. Different from the spent Fe/SiO$_2$(Q) without any co-feed in the reaction, the (100) and (011) peaks had high intensity. In addition, a broad peak is visible at $2\theta \sim 13°$ which is associated with the graphite oxide. The existence of (100) and (011) peaks suggest that coke on the Fe/SiO$_2$(Q) was less than that of Fe/SiO$_2$(Q) catalyst in the absence of $O_2$ co-feed. The appearance of graphite oxide peak indicate that the coking species has different composition from the one without $O_2$ co-feed. The Fe/SiO$_2$(Q) catalyst in the CO co-feed reaction condition showed the same XRD pattern as that of Fe/SiO$_2$(Q) in the absence of any co-feed, while the one in the $CO_2$ co-feed showed a relatively strong (001) peak. CO did not impact the DNMC reaction, but $CO_2$ suppressed the reaction due to steam reforming and/or reverse Boudouard reactions. The latter reaction could impact the coking species on the Fe/SiO$_2$(Q) catalyst. The XRD peak associated with graphite overlaps with the quartz peak at ~26°, so insight into the presence of graphite in each sample is unavailable. However, the $O_2$ and $CO_2$ co-fed samples demonstrate a higher intensity for the peak at 26° relative to the other peaks in the spectra, which could indicate a potential contribution from graphitic carbon in the XRD spectra.

Figure 24A:
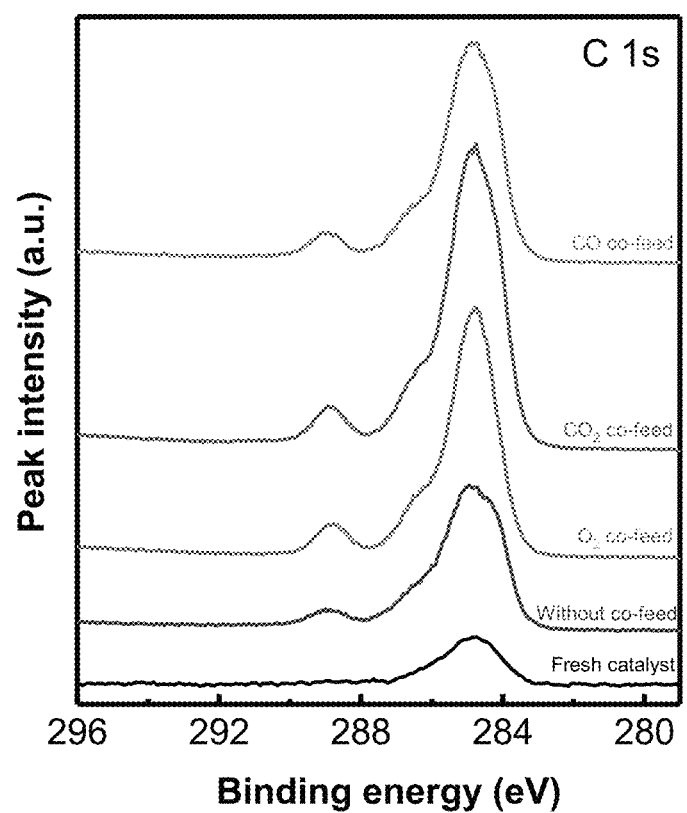
FIG. 24A shows elemental XPS spectra for C 1s photoelectron lines for fresh, as-is $Fe/SiO_2(Q)$ material and for $Fe/SiO_2(Q)$ samples following DNMC testing without co-feed and with $O_2$, $CO_2$ and CO co-feed, respectively.
Figure 24B:
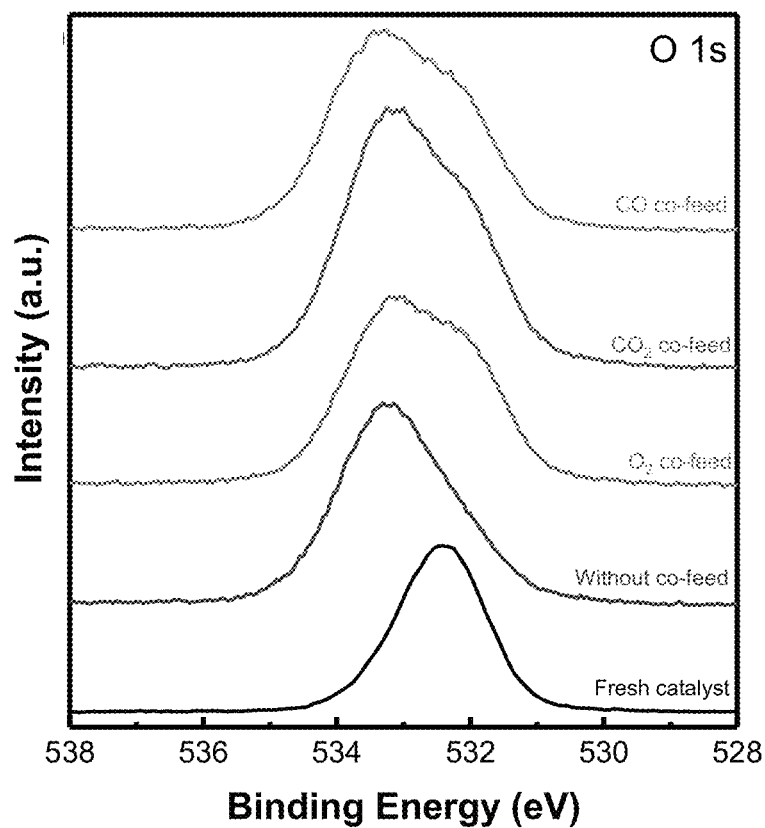
FIG. 24B shows O 1s photoelectron lines for fresh, as-is $Fe/SiO_2(Q)$ material and for $Fe/SiO_2(Q)$ samples following DNMC testing without co-feed and with $O_2$, $CO_2$ and CO co-feed, respectively.
Figure 24C:
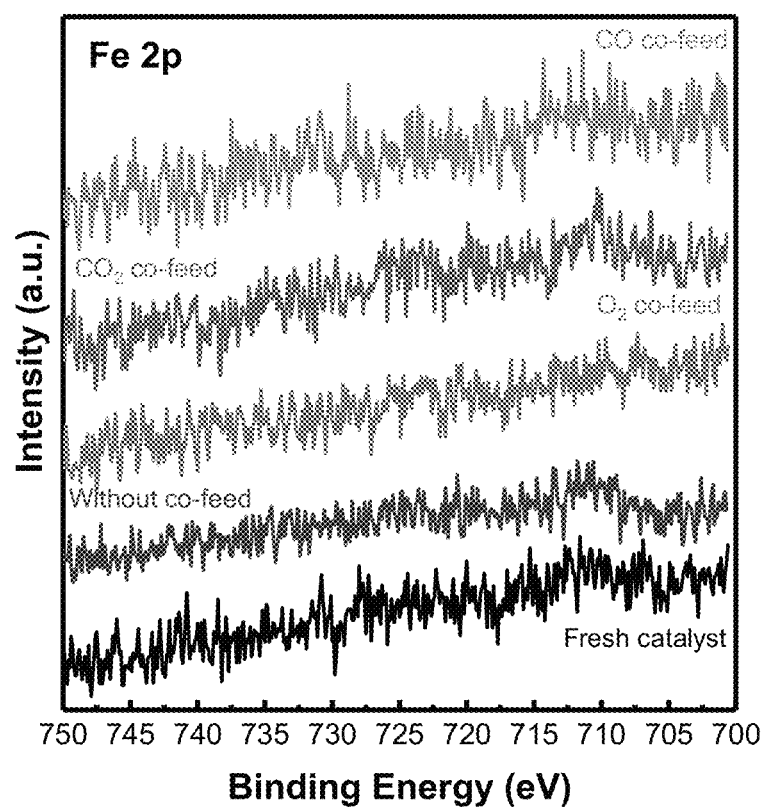
FIG. 24C shows elemental XPS spectra for Fe 2p photoelectron lines for fresh, as-is $Fe/SiO_2(Q)$ material and for $Fe/SiO_2(Q)$ samples following DNMC testing without co-feed and with $O_2$, $CO_2$ and CO co-feed, respectively.

FIGS. 24A-C show the XPS spectra of C 1s, O 1s, and Fe 2p on the spent Fe/SiO$_2$(Q) catalyst in the DNMC tests. Due to the low concentration of iron in the catalyst (0.075 wt %), the peaks correlating to iron binding energies, which appear at ~710 eV and ~730 eV, are poorly resolved and show a low signal-to-noise ratio (FIG. 24C). In FIG. 24A, the fresh $Fe/SiO_2(Q)$ sample has the peak centered at 284.7 eV, which is attributed to adventitious carbon present on the surface of the as-prepared catalyst. The spectrum of $Fe/SiO_2(Q)$ catalyst after the DNMC tests without any co-feed can be deconvoluted into four peaks, located at 284.1, 284.7, 286.4, 288.8 eV in sequence. In comparison to fresh $Fe/SiO_2(Q)$, the peak at 284.7 is much stronger, which is caused by the deposition of graphite-like carbon (C—C or C=C). The peaks centered at 284.1, 286.4, 288.8 eV can be assigned to carbon in the carbitic (e.g. Si—C or Fe—C), C—O—C and O—C—O structures, respectively. The presence of carbitic carbon in the catalyst is supported by the increase in peak intensity at 284.1 eV in the absence of any oxidative co-feed, and decrease in peak intensity when oxidative co-feed changed from CO to $CO_2$ and then $O_2$. The more oxidative co-feed such as $O_2$ apparently inhibits the formation of carbitic carbon species in the $Fe/SiO_2(Q)$ catalyst. In contrast to the trend of this peak, the peaks at 286.4 and 288.8 eV increase with increasing oxidation capability of co-feed. This suggests that more oxidized carbon species such as C—O—C and O—C—O structures exists in spent $Fe/SiO_2$ (Q) catalysts in the presence of oxidative co-feed in the DNMC reaction.

The O 1S XPS spectra in FIG. 24B further confirmed the variation in composition of coking species in the spent $Fe/SiO_2(Q)$ catalysts under different DNMC reaction conditions. The fresh $Fe/SiO_2(Q)$ has the XPS peak located at 532.6 eV that can be assigned to the Si—O—Si structure in the quartz support. The spent $Fe/SiO_2(Q)$ in the absence of any oxidative co-feed shifted the peak to higher binding energy region and the peak can be deconvoluted into two peaks at 534.0 eV and 532.6 eV, respectively. The appearance of the 534.0 eV peak is attributed to the formation of Si—O—H bond due to reductive reaction atmosphere in the DNMC tests. In the presence of oxidant in the reaction, a new peak at 532.0 eV appears. This peak is assigned to the oxygen bonded in the organic C—O structures. Consistent with the conclusion drawn from the XPS peaks of C 1s in FIG. 24a, the presence of oxidative co-feed oxidized partially the coking species and thus forms less graphitic carbon species on the $Fe/SiO_2(Q)$ catalyst.

Conclusions

An oxidative co-feed addition method was employed to concurrently realizing high methane conversion, high larger hydrocarbon yield, low coke formation, and reaction autothermality of the highly endothermic DNMC reaction. The catalyst was a quartz-supported Fe-species ($Fe/SiO_2(Q)$, "Q" denotes for quartz), prepared by a flame-fusing method. The oxidative co-feeds, including $O_2$, $CO_2$, and CO, in methane feed were tested for the DNMC. The $CO_2$ and CO brought adverse effects regarding improvement in either methane conversion or hydrocarbon product yield; while the $O_2$ co-feed demonstrated improvement in methane conversion (>200%), hydrocarbon product yield (>50%) and lighter hydrocarbon ($C_2$ and benzene) selectivity (up to 60%) compared to the DNMC in the absence of $O_2$ co-feed. Moreover, the oxidation reaction caused by $O_2$ co-feed can be used as the source of heat to maintain an autothermal reactor operating temperature, and thus realize the self-sustainability of heat requirement by the DNMC reaction. The composition and structural analyses of the spent $Fe/SiO_2(Q)$ confirmed the catalyst stability in the oxidative co-feed environment. The study forms a guidance for selecting reaction conditions towards upgrading of natural gas that often contains oxidative components into value-added larger hydrocarbons via the DNMC process.

References for Example 2

1. Wood, D. A.; Nwaoha, C.; Towler, B. F., Gas-to-liquids (GTL): A review of an industry offering several routes for monetizing natural gas. *J Nat Gas Sci Eng* 2012, 9, 196-208.
2. Borry, R. W.; Lu, E. C.; Kim, Y. H.; Iglesia, E., Non-oxidative catalytic conversion of methane with continuous hydrogen removal. *Stud Surf Sci Catal* 1998, 119, 403-410.
3. Wang, D. J.; Lunsford, J. H.; Rosynek, M. P., Characterization of a Mo/ZSM-5 catalyst for the conversion of methane to benzene. *J Catal* 1997, 169 (1), 347-358.
4. DeAngelis, M. T.; Rondinone, A. J.; Pawel, M. D.; Labotka, T. C.; Anovitz, L. M., Sol-gel synthesis of nanocrystalline fayalite (Fe2SiO4). *Am Mineral* 2012, 97 (4), 653-656.
5. Tan, P. L.; Leung, Y. L.; Lai, S. Y.; Au, C. T., Methane aromatization over 2 wt % Mo/HZSM-5 in the presence of O-2 and NO. *Catal Lett* 2002, 78 (1-4), 251-258.
6. Kosinov, N.; Coumans, F. J. A. G.; Uslamin, E.; Kapteijn, F.; Hensen, E. J. M., Selective Coke Combustion by Oxygen Pulsing During Mo/ZSM-5-Catalyzed Methane Dehydroaromatization. *Angew Chem Int Edit* 2016, 55 (48), 15086-15090.
7. Rodrigues, A. C. C.; Monteiro, J. L. F., CO2 addition on the non-oxidative dehydro-aromatization of methane over MoMCM-22. *Catal Lett* 2007, 117 (3-4), 166-170.
8. Mirzaei, A. A.; Vahid, S.; Feyzi, M., Fischer-Tropsch Synthesis over Iron Manganese Catalysts: Effect of Preparation and Operating Conditions on Catalyst Performance. *Res Progr Chem* 2011, 55-79.
9. Wang, Y.; Alsmeyer, D. C.; Mccreery, R. L., Raman-Spectroscopy of Carbon Materials—Structural Basis of Observed Spectra. *Chem Mater* 1990, 2 (5), 557-563.
10. Park, E.; Zhang, J. Q.; Thomson, S.; Ostrovski, O.; Howe, R., Characterization of phases formed in the iron carbide process by X-ray diffraction, Mossbauer, X-ray photoelectron spectroscopy, and Raman spectroscopy analyses. *Metall Mater Trans B* 2001, 32 (5), 839-845.
11. Ferrari, A. C.; Robertson, J., Interpretation of Raman spectra of disordered and amorphous carbon. *Phys Rev B* 2000, 61 (20), 14095-14107.
12. Ferrari, A. C.; Basko, D. M., Raman spectroscopy as a versatile tool for studying the properties of graphene. *Nat Nanotechnol* 2013, 8 (4), 235-246.
13. Heller, E. J.; Yang, Y.; Kocia, L.; Chen, W.; Fang, S. A.; Borunda, M.; Kaxiras, E., Theory of Graphene Raman Scattering. *Acs Nano* 2016, 10 (2), 2803-2818.
14. Rao, A. M.; Richter, E.; Bandow, S.; Chase, B.; Eklund, P. C.; Williams, K. A.; Fang, S.; Subbaswamy, K. R.; Menon, M.; Thess, A.; Smalley, R. E.; Dresselhaus, G.; Dresselhaus, M. S., Diameter-selective Raman scattering from vibrational modes in carbon nanotubes. *Science* 1997, 275 (5297), 187-191.

The citation of any document is not to be construed as an admission that it is prior art with respect to the present invention.

Although the present invention has been described in detailed with reference to certain embodiments, one skilled in the art will appreciate that the present invention can be practiced by other than the described embodiments, which have been presented for purposes of illustration and not of limitation. Therefore, the scope of the appended claims should not be limited to the embodiments contained herein.

What is claimed is:

1. A methane conversion device comprising:
a source of methane;
a source of gas including oxygen or oxygen containing compound;
a reactor having a first reaction zone and a second reaction zone;
a first valve in fluid communication with the source of methane, the first reaction zone, and the second reaction zone, the first valve having a first position in which the first reaction zone is placed in fluid communication with the source of methane, the first valve having a second position in which the second reaction zone is placed in fluid communication with the source of methane;
a second valve in fluid communication with the source of gas, the first reaction zone, and the second reaction zone, the second valve having a first position in which the second reaction zone is placed in fluid communication with the source of gas, the second valve having a second position in which the first reaction zone is placed in fluid communication with the source of gas;
a first catalyst having a surface exposed to the first reaction zone;
a second catalyst having a surface exposed to the second reaction zone; and
a controller for controlling a flow rate of methane and for controlling a flow rate of gas, wherein the controller is configured to execute a program stored in the controller to control the flow rate of methane and control the flow rate of gas such that the methane conversion device operates autothermally.

2. The methane conversion device of claim 1, wherein the first catalyst is fused to a first side of a wall and the second catalyst is fused to an opposite second side of the wall.

3. The methane conversion device of claim 2, wherein the wall is tube-shaped.

4. The methane conversion device of claim 1, wherein the first catalyst and the second catalyst comprise $Fe/SiO_2(Q)$.

5. The methane conversion device of claim 2, wherein the wall comprises quartz.

6. The methane conversion device of claim 2, wherein the first catalyst at least partially defines the first reaction zone and the second catalyst at least partially defines the second reaction zone.

7. The methane conversion device of claim 1, wherein the controller is configured to execute a program stored in the controller to:
(i) move the first valve from the first position to the second position and move the second valve from the first position to the second position, when the first catalyst has a pre-determined level of surface deposits including coke,
(ii) move the first valve from the second position to the first position and move the second valve from the second position to the first position, when the second catalyst has a pre-determined level of surface deposits including coke,
wherein the methane conversion device further comprises a first flow controller positioned upstream or downstream of the first valve for controlling the flow rate of methane, and a second flow controller positioned upstream or downstream of the second valve for controlling the flow rate of the gas, wherein the controller is configured to execute the program stored in the controller to:
(iii) control the flow rate of methane such that residence time of methane in the first reaction zone or the second reaction zone is in a range of 1-200 milliseconds.

8. A method for autothermal operation of a direct non-oxidative methane conversion (DNMC) device, the method comprising:
(a) providing a catalytic reactor, wherein the reactor comprises a catalyst fused to a first side of a wall and fused to an opposite second side of the wall;
(b) converting methane (MC) by flowing methane into the first side of the wall;
(c) obtaining products resulting from the methane conversion (MC) reaction;
(d) swapping the MC reaction to the second side of the wall;
(e) supplying to the first side of the wall a gas including oxygen resulting in a combustion reaction with one of the products;
(f) swapping the combustion reaction from the first side of the wall to the second side of the wall; and
(g) swapping the MC reaction from the side of the second wall to the first side of the wall.

9. The method of claim 8, wherein the products of step (b) comprise coke, $C_{2+}$ hydrocarbons, $H_2$, or a combination thereof.

10. The method of claim 9, wherein the $C_{2+}$ hydrocarbons comprise acetylene, ethylene, ethane, benzene, toluene, naphthalene, or a combination thereof.

11. The method of claim 8, wherein one of the products of step (e) is coke.

12. The method of claim 8, further comprising heating the catalytic reactor.

13. The method of claim 12, wherein the catalytic reactor is heated to about 1170K to about 1370K.

14. The method of claim 8, wherein a flow rate of methane in step (b) is about 5 ml/min to about 500 mL/min.

15. The method of claim 8, further comprising:
heating the catalytic reactor, wherein the catalytic reactor is heated to about 1170K to about 1370K, and wherein the flow rate of methane in step (b) is about 5 ml/min to about 500 mL/min,
adjusting the flow rate of methane and the gas to regulate a percentage of methane converted and/or a selectivity of the methane conversion to one or more of the products, and
adjusting the temperature of the catalytic reactor to regulate a percentage of methane converted and/or a selectivity of the methane conversion to one or more of the products,
wherein the percentage of methane converted is greater than 10%, and a yield $C_{2+}$ hydrocarbons is greater than 10%.

16. A method for producing a millisecond catalytic wall reactor, the method comprising:
(a) loading $Fe/SiO_2(Q)$ into a tube;
(b) heating the $Fe/SiO_2(Q)$ and the tube; and
(c) discharging the $Fe/SiO_2(Q)$ residue.

17. The method of claim 16, wherein the tube has an inner and an outer wall.

18. The method of claim 16, wherein step (b) is repeated multiple times,
wherein the heating is done by a $H_2/O_2$ flame, and
wherein the $Fe/SiO_2(Q)$ is uniformly dispersed and fully embedded in the tube wall, resulting in a catalyst embedded in the tube wall.

19. The method of claim 17, wherein the inner and outer wall comprise a quartz phase.

20. The method of claim 16, wherein the $Fe/SiO_2(Q)$ has a BET surface area of 0.1 to 0.5 $m^2/g$.

* * * * *